(12) United States Patent
Dickerson et al.

(10) Patent No.: US 7,213,400 B2
(45) Date of Patent: May 8, 2007

(54) LIQUEFYING AND STORING A GAS

(75) Inventors: Brian E. Dickerson, Littleton, CO (US); Steve W. Delve, Denver, CO (US)

(73) Assignee: Respironics In-X, Inc., Murrysville, PA (US)

( * ) Notice: Subject to any disclaimer, the term of this patent is extended or adjusted under 35 U.S.C. 154(b) by 0 days.

(21) Appl. No.: 11/131,071

(22) Filed: May 16, 2005

(65) Prior Publication Data

US 2006/0086099 A1    Apr. 27, 2006

Related U.S. Application Data

(60) Provisional application No. 60/677,661, filed on May 2, 2005, provisional application No. 60/622,483, filed on Oct. 26, 2004.

(51) Int. Cl.
| | |
|---|---|
| *F25B 9/00* | (2006.01) |
| *F17C 5/02* | (2006.01) |
| *F17C 3/10* | (2006.01) |
| *F25J 1/00* | (2006.01) |
| *A62B 7/06* | (2006.01) |

(52) U.S. Cl. .............................. 62/6; 62/606; 62/47.1; 62/48.2; 128/201.21

(58) Field of Classification Search ............ 62/6, 62/606, 47.1, 48.2, 50.2; 128/201.21
See application file for complete search history.

(56) References Cited

U.S. PATENT DOCUMENTS

| | | | |
|---|---|---|---|
| 2,854,826 A | 10/1958 | Johnston | |
| 2,909,903 A | 10/1959 | Zimmermann | |
| 2,951,348 A | 9/1960 | Loveday et al. | |
| 2,964,918 A | 12/1960 | Hansen et al. | |
| 3,098,362 A | * 7/1963 | Sohda et al. | ............... 62/48.2 |
| 3,199,303 A | 8/1965 | Haumann et al. | |

(Continued)

FOREIGN PATENT DOCUMENTS

EP    0221887    10/1987

(Continued)

OTHER PUBLICATIONS

Author Unkown, "Air Liquide- Bulk Gases." www.airliquide.com, date unknown.

(Continued)

*Primary Examiner*—William C. Doerrler
(74) *Attorney, Agent, or Firm*—Faegre & Benson LLP

(57) ABSTRACT

Apparatus and methods for improving the safety and efficiency and decreasing the cost of producing liquid gas, such as liquid oxygen, with a small-scale use liquefaction device, according to various embodiments of the present invention. In one embodiment, liquid oxygen barrier may be added to interface between a cryocooler and a dewar to control rate of liquid oxygen escape upon a tipping of the dewar. A boiloff vessel in fluid communication with the dewar allows expanding gas from a tipped dewar to escape while allowing the liquid to safely settle in the boiloff vessel. A temperature sensing circuit, in proximity with a heat dissipator or cold finger of the cryocooler, is operable to break an electrical power circuit of the cryocooler or cooling fan when a sensed temperature exceeds a predetermined temperature. Oxygen purity of a feed stream of gas may be sensed and/or displayed.

38 Claims, 36 Drawing Sheets

U.S. PATENT DOCUMENTS

| | | | |
|---|---|---|---|
| 3,797,262 A | | 3/1974 | Eigenbrod |
| 3,807,396 A | * | 4/1974 | Fischel .................. 128/201.21 |
| 3,941,124 A | | 3/1976 | Rodewald et al. |
| 3,946,572 A | | 3/1976 | Bragg |
| 4,018,582 A | | 4/1977 | Hinds et al. |
| 4,211,086 A | | 7/1980 | Leonard et al. |
| 4,216,819 A | | 8/1980 | Notaro |
| 4,253,519 A | | 3/1981 | Kun et al. |
| 4,279,127 A | | 7/1981 | Longsworth |
| 4,388,809 A | | 6/1983 | Sarcia |
| 4,510,760 A | | 4/1985 | Wieland |
| 4,529,411 A | | 7/1985 | Goddin, Jr. et al. |
| 4,542,010 A | | 9/1985 | Roman et al. |
| 4,570,819 A | | 2/1986 | Perkins et al. |
| 4,575,386 A | | 3/1986 | Hamers |
| 4,591,365 A | | 5/1986 | Burr |
| 4,627,860 A | | 12/1986 | Rowland |
| 4,701,187 A | | 10/1987 | Choe et al. |
| 4,826,510 A | | 5/1989 | McCombs |
| 4,841,732 A | | 6/1989 | Sarcia |
| 4,870,960 A | | 10/1989 | Hradek |
| 4,918,312 A | * | 4/1990 | Wellman et al. ............. 250/352 |
| 4,971,609 A | | 11/1990 | Pawlos |
| 5,163,297 A | | 11/1992 | Yani et al. |
| 5,295,355 A | | 3/1994 | Zhou et al. |
| 5,327,729 A | | 7/1994 | Yanai et al. |
| 5,379,601 A | * | 1/1995 | Gillett ........................ 62/51.1 |
| 5,406,843 A | | 4/1995 | Hannan et al. |
| 5,579,646 A | | 12/1996 | Lee |
| 5,584,194 A | | 12/1996 | Gardner |
| 5,709,203 A | | 1/1998 | Gier |
| 5,893,275 A | | 4/1999 | Henry |
| 5,908,053 A | | 6/1999 | Byrd |
| 5,979,440 A | | 11/1999 | Honkonen et al. |
| 5,988,165 A | | 11/1999 | Richey, II et al. |
| 6,212,904 B1 | | 4/2001 | Arkharov et al. |
| 6,314,957 B1 | | 11/2001 | Boissin et al. |
| 6,327,862 B1 | | 12/2001 | Hanes |
| 6,651,653 B1 | | 11/2003 | Honkonen et al. |
| 6,651,658 B1 | | 11/2003 | Hill et al. |
| 6,681,764 B1 | | 1/2004 | Honkonen et al. |
| 6,691,702 B2 | * | 2/2004 | Appel et al. ............ 128/202.26 |
| 6,698,423 B1 | | 3/2004 | Honkonen et al. |
| 2004/0045315 A1 | | 3/2004 | Kamoshita et al. |
| 2005/0274142 A1 | * | 12/2005 | Corey ......................... 62/643 |
| 2006/0026988 A1 | * | 2/2006 | Unger ......................... 62/640 |

FOREIGN PATENT DOCUMENTS

| | | |
|---|---|---|
| GB | 1416163 | 12/1975 |
| GB | 2045413 A * | 10/1980 |
| JP | 11153672 A | 6/1999 |
| JP | 2004085167 | 3/2004 |
| WO | WO98/58219 | 12/1998 |

OTHER PUBLICATIONS

Author Unkown, "Praxair, Inc.—Oxygen Therapy for Infants, Children and Adults." www.praxair.com, date unknown.

Author Unknown, "Praxair, Inc.—Cyrogenic On-site Air Separation Plants." www.praxair.com, date unknown.

\* cited by examiner

LIQUEFYING AND STORING A GAS

CROSS-REFERENCE TO RELATED APPLICATIONS

The present application claims the benefit of U.S. Provisional Patent Application No. 60/622,483, entitled "Liquefying and Storing a Gas" and filed on Oct. 26, 2004. The present application also claims the benefit of U.S. Provisional Patent Application No. 60/677,661, entitled "Liquefying and Storing a Gas" and filed on May 2, 2005. The aforementioned applications are hereby incorporated by reference herein in their entirety for all purposes.

The present application is further related to U.S. patent application Ser. No. 11/130,646 entitled "Liquefying and Storing a Gas," filed on a date even herewith and assigned to an entity common hereto, the contents of which are herein incorporated by reference in their entirety for all purposes.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever. Copyright © In-X Corporation 2004, 2005.

FIELD

The present application relates to the production and storage of liquefied gases at the site where at least some of the liquefied gas is to be used. In particular, the present invention relates to the production and storage of liquid oxygen in an oxygen patient's residence, and the improvement of cost, safety, and/or efficiency thereof.

BACKGROUND

The liquefaction of low boiling point gases, such as air and the components of air, such as oxygen, nitrogen and argon, has been practiced for over 100 years, and the liquefaction of such gases on an industrial scale has been practiced since the beginning of the 20th century. Typically, commercial liquefiers are designed to produce hundreds of tons of liquid cryogens per day. Such industrial liquefiers are reliable, and are capable of producing liquefied gas with relatively high energy efficiency. For consumers of liquefied gas requiring relatively small quantities, small insulated containers, known as dewars, are filled with liquefied gas produced by commercial facilities and transported to the consumer. Consumers of small quantities of liquefied gas include hospitals, which require oxygen for delivery to patients and nitrogen for use as a refrigerant. Also, people suffering from chronic respiratory insufficiency that have been prescribed home oxygen by their physicians may have liquefied oxygen delivered to their residences.

Initially, attempts to provide such a liquefier involved efforts to miniaturize large scale liquefying plants. However, due to the complexity of such systems, which are typically based on the Claude cycle or its variants, these attempts failed. Also, the extremely small mechanical components resulting from the miniaturization of such liquefiers were expensive to produce and unreliable in operation. Current liquefiers often involve complex and/or expensive liquefaction components, and often lack safety features to make a liquefaction system safer for residential, small-scale, and/or portable use.

For the above-stated reasons, it would be advantageous to provide a method and apparatus for improving the safety, efficiency, and/or cost of producing and storing relatively small quantities of liquefied gas at the location where the liquefied gas is to be used, such as at an oxygen therapy patient's residence.

SUMMARY

Apparatus and methods for improving the safety and efficiency and decreasing the cost of producing liquid oxygen with a small-scale use liquefaction device are described. In one embodiment, a liquid oxygen barrier may be added to an interface between a cryocooler and a dewar to control the rate of liquid oxygen escape upon a tipping of the dewar. A boiloff tube may be fluidly connected to the dewar to allow expanding gas from a tipped dewar to escape while allowing the liquid to safely settle in the boiloff tube. A tilt switch may be used to identify whether a liquefaction device has been tipped or tilted, and to cut electrical power to the system upon such a condition. The tilt switch may be a mercury switch, which may be operative to cut electrical power upon at least a forty-five degree tip or tilt.

In one embodiment, a cold finger of the cryocooler extends within the dewar and may prevent overfilling of the dewar. The cold finger has a temperature gradient with one end having a temperature higher than the boiling point of oxygen and the other end having a temperature lower than the boiling point of oxygen. As the gas liquefies and fills the dewar, the liquid level rises only to a level on the cold finger at which the temperature exceeds the boiling point of oxygen. At this level, no exposed part of the cold finger is cold enough to liquefy oxygen, so the liquid level does not rise further; this may prevent overfilling of the dewar by mechanical, rather than electrical, means. Alternatively, a liquid level sensor may be used to trigger a system shutdown when the liquid level exceeds a predetermined limit.

In one embodiment, the liquefaction device controls a feed flow of oxygen using a regulator and orifice to maintain a steady feed flow from an oxygen concentrator. Use of a fixed configuration regulator and orifice allows for the production of USP93 approved liquid oxygen by receiving USP93 gaseous oxygen from a concentrator and passing it to the rest of the system at a steady flow rate. A regulator and orifice combination in a liquefaction device may also be less expensive and easier to manufacture than a variable flow rate valve, or a variable flow rate valve controlled with a controller in a control loop.

In one embodiment, a compressor in fluid communication with the dewar may pressurize the dewar to push liquid oxygen out of a transfill tube and into a portable stroller. This pressurization may be accomplished using ambient air. A portable liquid oxygen stroller, with a valve adapted to interface with a transfill valve on the liquefaction device, may be pushed down onto the transfill valve. The portable liquid oxygen stroller may be especially adapted or approved for use with USP93 oxygen. This action of placing a portable stroller onto a transfill valve may activate a transfill switch, which may act to close any fluid outlets from the dewar except for the transfill tube. The closing of the fluid outlets of the dewar may involve activating a solenoid valve to close a vent line from the dewar. The transfill switch may also connect to a programmable logic device that terminates the transfill process after a preset time limit.

Pressure relief valves, which may be placed in a feed line and a vent line, may prevent over-pressurization of the dewar or the plumbing of the liquefaction device during a transfill process.

In one embodiment, a feed gas flow from a concentrator is separated into two flows: one for use by a patient and one for liquefaction. The patient flow may be controlled with a patient flowmeter and set to a prescribed limit. The patient flow output may also allow for the connection of a canula line and a humidifier element.

In one embodiment, a liquefaction device may be held together with a mounting shroud. The mounting shroud may include two halves. The two halves may include a clamping element configured to encompass both a cryocooler flange and a dewar flange, with an O-ring placed between the cryocooler flange and the dewar flange. When the mounting shroud, and thus the clamping element, is closed, the clamping element provides opposing axial forces to push the cryocooler flange and dewar flange together to compress the O-ring. This creates a seal between the cryocooler flange and the dewar flange, preventing leakage of gaseous or liquid oxygen even when the liquefaction device is tipped over. The mounting shroud may also secure the dewar and cryocooler into a chassis assembly. Vibration dampeners may be mounted between the mounting shroud and chassis to ameliorate noise and vibration. A cooling fan may be secured to the mounting shroud to allow cooling of a cryocooler fin and of electrical components. The mounting shroud design itself may provide an enclosed air path to route air through a cooling fin of the cryocooler, reducing the likelihood that the cryocooler overheats or suffers a seized displacer.

In one embodiment, a liquefaction device employs a stainless steel dewar with a bellows neck. A metal dewar with a metal neck tube may be more durable than either a glass dewar or metal dewar with a composite neck tube. A metal neck tube reduces flammability concerns due to the high oxygen environment. An all-metal dewar construction allows for the welding of a mounting flange directly to the top of the dewar, which, in turn, allows for a better seal between the dewar and a cryocooler flange. A bellows neck design reduces thermal conductivity and further reduces heat loss from inside the dewar. Such a dewar design provides ease of manufacture and a reduction in the number of necessary assembly parts.

An apparatus for enhancing safety in gas liquefaction or liquid gas storage is provided, according to various embodiments of the present invention. Such embodiments of an apparatus include a container operable to contain liquid gas for portable medical gas therapy, a boiloff vessel having two openings, one opening in fluid communication with the container and configured to receive a rapidly expanding mixture of gas and liquid gas when the container is tipped or tilted. The boiloff vessel may be configured to permit the liquid gas within the rapidly expanding mixture to fall to a bottom of the boiloff vessel while permitting the gas within the rapidly expanding mixture to exit the boiloff vessel via the other opening. Such embodiments may further include a gas vent line, such that the boiloff vessel is in fluid communication with the container via the gas vent line and the gas vent line vents gas from the container. The boiloff vessel may be further configured to contain the liquid gas fallen from the rapidly expanding mixture until the liquid gas has evaporated and exited the boiloff vessel via the second opening. In some cases, the boiloff vessel may be a cylindrical vessel having two ends, the first end having the one opening, and the second end having the other opening. In some alternative instances, the boiloff vessel may be a cylindrical vessel having two ends, the first end having one opening, with the other opening located closer to the first end than to the other end.

Embodiments of the apparatus may further include a vent line in fluid communication with the first opening, such that the vent line extends away from a cryocooler in one direction. In such cases, the cryocooler may be in communication with the container, and the second opening may open in a direction substantially opposite to the direction in which the vent line extends away from the cryocooler. Other embodiments of the apparatus may further include a cryocooler with a cold finger, the cold finger extending within the container and operable to liquefy gas for containment in the container.

Various other embodiments of the apparatus may further include an accelerometer configured to break an electrical power circuit of the cryocooler when the container experiences an acceleration greater than a predetermined acceleration. In some cases, embodiments of the apparatus may include a means for decreasing a rate at which the rapidly expanding mixture travels from the container to the boiloff vessel upon a tipping of the container. In yet other cases, embodiments of the apparatus may further include an oxygen concentrator operable to supply a feed stream of oxygen gas, a feed tube configured to carry the feed stream from the oxygen concentrator to the cryocooler, and a one-way check valve situated in the feed tube. In such cases, the one-way check valve may be configured to permit the feed stream to flow from the oxygen concentrator to the cryocooler in one direction, and to prevent a back pressure from the cryocooler to the oxygen concentrator in an opposite direction.

According to yet other instances of the embodiments, the apparatus may further include a first pressure relief line having a first end and a second end, the first end of the first pressure relief line in fluid communication with the feed tube at a location between the one-way check valve and the cryocooler, the second end of the first pressure relief line in fluid communication with the boiloff vessel, the first pressure relief line comprising a first pressure relief valve configured to permit fluid flow through the first pressure relief line from the feed tube to the boiloff vessel when a first pressure within the feed tube exceeds a predetermined pressure. In such instances, the embodiments of the apparatus may further include a vent tube having a first end and a second end, the first end of the vent tube in fluid communication with the container, the second end of the vent tube in fluid communication with the boiloff vessel, the vent tube configured to permit gases to exit the container, and a second pressure relief line in fluid communication with the vent tube, the second pressure relief line comprising a second pressure relief valve configured to permit fluid flow through the second pressure relief line from the vent tube when a second pressure within the vent tube exceeds the predetermined pressure. According to such instances of the embodiments, the vent tube may include a solenoid valve operable to stop flow through the vent tube, and the second pressure relief line may bypass the solenoid valve.

An apparatus for enhancing safety in gas liquefaction or liquid gas storage is provided, according to various other embodiments of the present invention. Such embodiments may include a dewar operable to contain liquid oxygen gas, a cryocooler including a cold finger, the cold finger extending within the dewar and operable to liquefy oxygen gas for containment in the dewar, and a switch configured to break an electrical power circuit of the cryocooler when the dewar tips through a predetermined angle. In some cases, the switch may be a mercury switch and the predetermined angle may be at least approximately forty-five degrees.

An apparatus for decreasing escape rate of liquid oxygen in a tipping event is provided, according to various embodiments of the present invention. Such embodiments may include a container operable to contain liquid oxygen for oxygen therapy, a cryocooler with a cold finger, the cold finger extending within the container and operable to liquefy oxygen gas for containment in the container, an annular channel defined by the cryocooler and the container on an outer side and the cold finger on an inner side, the oxygen gas flowing through the annular channel, and a barrier situated in the annular channel and configured to reduce a cross-sectional area of the annular channel to decrease an escape rate of a rapidly expanding combination of the liquid oxygen and the oxygen gas upon a tipping of the container. In some instances of the embodiments, the embodiments may further include a first flange formed on the cryocooler encircling the cold finger and a second flange formed on the container, the second flange releasably coupled to the first flange to form the annular channel through which the oxygen gas flows between the cryocooler and the container without escaping between the first flange and the second flange. In other instances of the embodiments, the first flange has an outer diameter that increases as it approaches the second flange forming a first sloped surface, the second flange has an outer diameter that increases as it approaches the first flange forming a second sloped surface. In such instances, embodiments of the apparatus may further include a clamp configured to conform to the first sloped surface and the second sloped surface and to apply a normal force to each of the first and second sloped surfaces to create a corresponding axial force that pushes the first flange and the second flange together. In yet other instances of the embodiments, the barrier may be situated at least partially between the first flange and the second flange, or, alternatively, interposed between the first flange and the second flange. In some cases, the barrier may be integral with the cryocooler and/or the dewar.

Some embodiments of apparatus according to the present invention may further include a boiloff vessel comprising a first opening and a second opening, the first opening in fluid communication with the container and configured to receive the rapidly expanding combination of the liquid oxygen and the oxygen gas upon a tipping of the container, the boiloff vessel configured to permit the liquid oxygen within the rapidly expanding combination to fall to a bottom of the boiloff vessel while permitting the oxygen gas within the rapidly expanding combination to exit the boiloff vessel via the second opening. According to other embodiments of the apparatus, the barrier reduces a cross-sectional width of the annular channel to approximately ten thousandths to fifteen thousandths of an inch. According to yet other embodiments of the apparatus, the annular channel is a first annular channel, the inner side is a first inner side, the outer side is a first outer side, and the barrier may include a flow director portion configured to encircle at least a portion of the cold finger, the flow director portion separating at least a portion of the first annular channel into a second annular channel and a third annular channel. According to such embodiments, the second annular channel is defined by the flow director portion on a second outer side and the cold finger on the first inner side, the third annular channel is defined by the cryocooler and the container on the first outer side and the flow director portion on a second inner side, and the feed stream of gas flows through the second annular channel and vent gas flows through the third annular channel.

An apparatus for enhancing safety in oxygen gas liquefaction is provided, according to various other embodiments of the present invention. Such embodiments may include a container operable to contain liquid oxygen for portable oxygen therapy, a cryocooler with a cold finger and a heat dissipator, the cold finger extending within the container and operable to liquefy oxygen gas for containment in the container, and a temperature sensing circuit with a temperature sensor in proximity with the heat dissipator. According to such embodiments, the temperature sensing circuit may break an electrical power circuit of the cryocooler when a sensed temperature exceeds a predetermined temperature incompatible with proper cryocooler operation.

An apparatus for enhancing safety in oxygen gas liquefaction is provided, according to various other embodiments of the present invention. Such embodiments may include a container operable to contain liquid oxygen for portable oxygen therapy, a cryocooler comprising a cold finger, the cold finger extending within the container and operable to liquefy oxygen gas for containment in the container, and a temperature sensing circuit with a temperature sensor in proximity with the cold finger. According to such embodiments, the temperature sensing circuit may break an electrical power circuit of the cryocooler when a sensed temperature exceeds a predetermined temperature incompatible with proper cryocooler operation.

An apparatus for enhancing safety in gas liquefaction, according to various alternative embodiments of the present invention. Such embodiments may include a container operable to contain liquid oxygen for portable oxygen therapy, a cryocooler with a cold finger, the cold finger extending within the container and operable to liquefy oxygen gas for containment in the container, and an oxygen concentrator to supply a feed stream of the oxygen gas. Such embodiments may further include a feed tube configured to carry the feed stream from the oxygen concentrator to the cryocooler, an oxygen purity sensor in fluid communication with the feed tube, the oxygen purity sensor configured to observe oxygen purity of the feed stream and to transmit a signal indicating the oxygen purity, and an oxygen purity indicator configured to receive the signal and to display a graphical representation of the oxygen purity. For example, the graphical representation may be green if the oxygen purity exceeds a predetermined level for oxygen therapy use, and may be red if the oxygen purity is less than the predetermined level. As another possible example, the graphical representation may be a digital numerical representation indicating a percentage of the oxygen gas by volume in the feed stream. In some cases, the predetermined level may be ninety percent by volume.

Other features of embodiments of the present invention will be apparent from the accompanying drawings and from the detailed description that follows.

DETAILED DESCRIPTION

Figure 1:
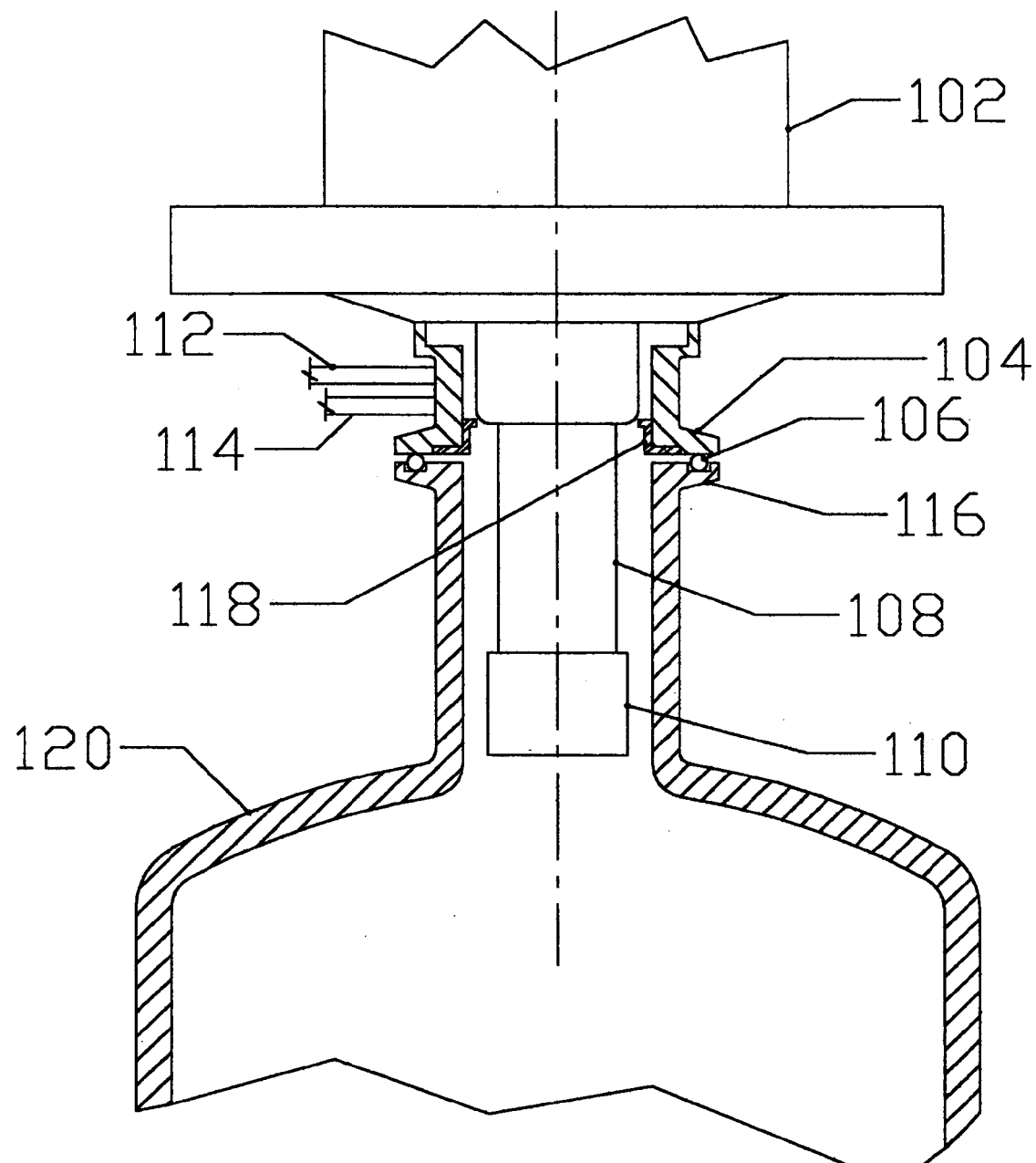
FIG. 1 depicts a cross-section, cut-away view of the cryocooler and dewar interface of one embodiment of the present invention.

In recent years, cryocoolers have been intensively developed. Initially, cryocoolers were developed for the military for use in such applications as cooling infrared sensors, semiconductor chips, microwave electronics, high temperature superconductivity applications, fiber optic amplifiers, etc. The cryocoolers developed for these applications operated in a temperature range of from about 20K to 150K, and their cooling capacity ranged from less than a watt to over 100 watts. In addition, the cryocoolers developed for the above-described military applications provided their heat input at or near the lowest temperature point of the cryocooler. For instance, the component to be cooled was typically attached to the cold point (the "cold finger") of the cryocooler, transferring heat directly to that component, with minimal conduction losses. However, for use in small scale gas liquefiers, features such as precise control of each parameter of liquefaction and quick cool down are not necessary, and serve only to increase the cost of the device.

With respect to the need for relatively small but steady quantities of oxygen by patients on oxygen therapy, there have been several ways in which the needs of such patients have been met. The most common method for oxygen therapy patients to receive oxygen is through regular deliveries of oxygen produced at a commercial plant. The oxygen may be delivered as either a pressurized gas or as a liquid. When delivered as a pressurized gas, the oxygen presents a hazard because of the high pressure under which it is stored and because oxygen is highly reactive. Oxygen delivered as a liquid is subject to losses resulting from boil-off, which occurs due to the inevitable warming of the liquefied gas over time. Because such losses occur even when specially insulated containers, or dewars, are used, deliveries of fresh liquid oxygen must be made on a weekly basis.

It is also known to provide devices which extract or concentrate oxygen found in the ambient air. These devices obviate the need to store a potentially hazardous material. However, these devices are typically not portable, and therefore a person on continuous oxygen therapy must often rely on oxygen that has been "bottled" commercially in order to leave his or her residence.

In recent years, some advances have been made toward producing home-use oxygen liquefaction devices. Examples of such devices may be found in U.S. Pat. No. 5,893,275, entitled "Compact Small Volume Liquid Oxygen Production System," filed on Sep. 4, 1997, and U.S. Pat. No. 6,212,904, entitled "Liquid Oxygen Production," filed on Nov. 1, 1999, of which the content of each is herein incorporated by reference in its entirety.

Some prior gas liquefaction devices have typically employed complex and/or expensive condenser structures. It has previously been thought advantageous to force a feed gas stream across a cold surface in order to improve liquefaction efficiency. It has also previously been thought advantageous to employ a cooled structure, such as a double-walled condenser structure attached to a cold surface of the cryocooler, and to direct the feed gas through the condenser structure to increase surface area over which liquefaction occurs.

Additionally, home-use oxygen liquefaction devices often lack safety mechanisms to prevent injury or damage when the device is tipped onto its side or overheats. Liquid oxygen escaping from a tipped storage dewar can expand and boil rapidly as it encounters warm surfaces, causing vast amounts of liquid oxygen to spray or shoot rapidly through an exhaust vent. If the liquefaction device's electrical power remains on during a tip, escaping oxygen can also cause a fire hazard if it encounters spark or flame. Overheating components may also damage a liquefaction device. In liquefaction devices employing cryocoolers, the cryocooler can overheat or suffer a seized displacer. Overfilling a liquid oxygen storage dewar may also be hazardous; some oxygen liquefaction devices rely on an electronic controller to stop liquid oxygen production. Other safety concerns involve the transfilling of a portable liquid oxygen stroller from another dewar; this process may sometimes cause portions of a portable liquid oxygen stroller to freeze onto a connection to another dewar, resulting in an overfill of the portable stroller or an over-emptying of the dewar.

Because medical oxygen may be considered a prescription drug, it may be regulated by a government agency. For instance, the Federal Drug Administration (FDA) in the United States regulates oxygen liquefaction devices. Resources have been expended for United States Pharmacopeia (USP) approved oxygen liquefaction devices. USP approved devices produce oxygen that is approximately 99.0% pure; USP93 approved devices produce oxygen that is 93% pure, within a ±3% tolerance. USP approved devices often seek, at higher cost, to optimize the oxygen liquefaction process to achieve an approximate 99.0% purity. This may be done through the use of an advanced feedback and control loop that varies the flow rate of a feed gas containing oxygen. However, the necessary sensors and controllers used for such an optimization process can be expensive.

In the present application, apparatus and methods for improving the safety and efficiency and decreasing the cost of producing liquid oxygen with a small-scale use liquefaction device are described. Various terminology is used herein to refer to one or more aspects of embodiments of the present invention. A "residential," "small-scale use," or "portable" liquefaction device refers to a liquefaction device operable to produce as much as twenty-five liters of liquid gas per day; typically, such devices produce small-scale amounts of liquid gas in the range of approximately 1.5 liters of liquid gas in a twenty-four hour period. As used herein, the terms "boiloff vessel" and "phase separator" are used interchangeably, and are used in their broadest sense to refer to any container able to receive a rapidly-expanding mixture of gas and liquid gas to separate the gas and liquid phases by allowing the liquid gas to fall to the bottom of the container and boil off gradually while permitting the gas to exit the container. "Boiloff tube" refers to one particular embodiment of a boiloff vessel configuration. As used herein, the term "dewar" is used in its broadest sense to refer to a container, for example a cryogenically-insulated container, operable to receive and/or store a liquid gas, for example liquid oxygen. As used herein, the terms "portable dewar," "stroller," and "portable stroller" are used interchangeably, and are used in their broadest sense to refer to a container, for example a cryogenically-insulated container, operable to receive and/or store a liquid gas, for example liquid oxygen, in a way that permits the container to be carried, carted, or the like for ambulatory medical gas therapy.

As used herein, the term "in fluid communication" is used in its broadest sense to refer to elements related in a way that permits fluid to flow between them, either indirectly via another element, or directly. As used herein, the terms "feed tube" and "feed line" and "feed hose" are used interchangeably, and are used in their broadest sense to refer to any fluid flow mechanism operable to convey gas from a concentrator to a cryocooler and/or dewar. As used herein, the terms "vent tube" and "vent line" and "vent hose" are used interchangeably, and are used in their broadest sense to refer to any fluid flow mechanism operable to convey gas away from a cryocooler and/or dewar. As used herein, the term "heat dissipator" is used in its broadest sense to refer to a thermal mechanism operable to receive heat from one area and release it in another area. One example of an embodiment of a heat dissipator is a cryocooler cooling fin. As used herein, the indefinite articles "a" or "an" are used in their traditional senses to refer to one or more of an element. As used herein, the phrases "in one embodiment," "according to one embodiment," and the like generally mean that the particular feature, structure, or characteristic following the phrase is included in at least one embodiment of the present invention, and may be included in more than one embodiment of the present invention. Importantly, such phases do not necessarily refer to the same embodiment.

Figure 5:
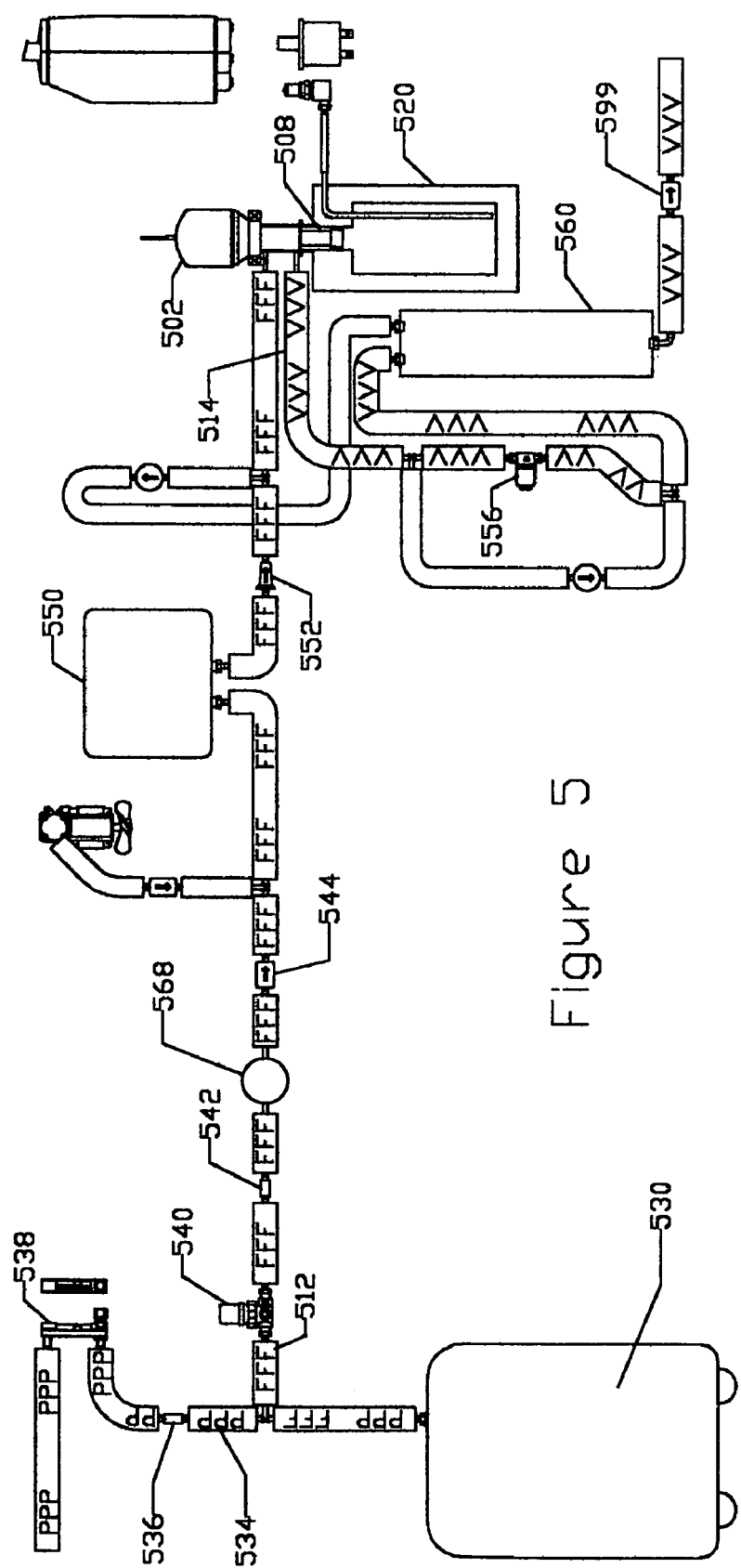
FIG. 5 depicts a conceptual system diagram of one embodiment of the present invention coupled to an oxygen concentrator, illustrating liquid flow during a liquefaction cycle.

With reference to FIG. 5, a conceptual system diagram of one embodiment of the present invention coupled to an oxygen concentrator, illustrating liquid flow during a liquefaction cycle, is depicted. Oxygen concentrator 530 outputs a flow of concentrated oxygen. In FIG. 5, "FFF" refers to the presence of oxygen feed flow, "PPP" refers to the presence of patient gaseous oxygen flow, and "VVV" refers to the presence of vent gas flow. A typical concentrator 530 may output between approximately five and ten liters of oxygen per minute. In one embodiment, oxygen concentrator outputs a flow of USP93 approved oxygen. According to some embodiments of the present invention, the output flow rate of oxygen concentrator 530 may be set to its maximum value. From the oxygen concentrator 530, the output flow branches into a feed flow line 512 "FFF" and a patient flow line 534 "PPP." The patient flow passes through a patient orifice 536. The patient orifice 536 may be configured to prevent the patient flow line 534 from "robbing" the feed flow line 512, or in other words allowing too much of the concentrator's 530 output flow to pass through the patient flow line 534 and not enough to pass through the feed flow line 512. After passing through the patient orifice 536, the patient flow passes through a patient flowmeter 538, which allows the patient to adjust the flow rate of oxygen received from the patient flow line 534. In one embodiment, the patient flowmeter 538 comprises a variable orifice in the form of a needle valve. The patient flow line 534 may provide a connection port similar to those found on an oxygen concentrator, allowing for the connection of a canula line or a humidifier bottle if desired.

In one embodiment, the feed gas flow rate in the feed flow line 512 is maintained at a constant rate by pressure regulator 540 and orifice 542. The oxygen concentrator 530 typically has an outlet pressure of about six to eight pounds per square inch gauge (PSIG). The pressure regulator 540 operates to reduce the pressure of the feed flow. In one embodiment, the pressure of the feed flow is reduced to 3.8 PSIG. After passing through regulator 540, the feed flow passes through an orifice 542. In one embodiment, the orifice 542 has a diameter of 0.016 inches. An oxygen feed flow at a pressure of 3.8 PSIG will pass through an orifice of 0.016 inch diameter at a rate of approximately 1.25 liters per minute. According to some embodiments of the present invention, a pressure regulator 540 and orifice 542 combination permit a constant feed flow rate of oxygen gas to be supplied for liquefaction. Alternatively, various other fixed flow rates may be achieved through the selection of different pressure regulators 540 and/or orifices 542 of different sizes.

A liquefaction device employing a fixed pressure regulator 540 and a fixed diameter orifice 542 has advantages over a system employing a variable flow control feedback loop, such as those employing a variable valve with a controller. For instance, a regulator 540 and orifice 542 combination may cost less and may be easier to manufacture than a variable flow system. In one embodiment using a regulator 540 and orifice 542 combination, concentrated USP93 oxygen from an oxygen concentrator 530 may simply be regulated to a fixed pressure and sent through a fixed diameter orifice that sends a steady flow of USP93 oxygen gas to be liquefied as USP93 oxygen.

Next, the feed flow passes through a one-way check valve 544 and into desiccant cartridge 550. According to some embodiments of the present invention, desiccant cartridge 550 is an optional element. In one embodiment, desiccant cartridge 550 is a removably attachable desiccant cartridge for dehumidifying a gas feedstream in a portable gas liquefying apparatus. Preferably, the desiccant cartridge 550 is compact and portable. The desiccant cartridge 550 may reduce or prevent rime formation and reduce moisture content to increase overall efficiency of the liquefaction apparatus.

In one embodiment, the desiccant cartridge comprises a gas feedstream inlet, a dehumidifying zone in communication with the gas feedstream inlet, and a dehumidified gas feedstream outlet in communication with the dehumidifying zone. The gas feedstream inlet may be adapted to receive a gas feedstream from a gas feedstream generating device, such as oxygen concentrator 530. The dehumidified gas feedstream outlet may be adapted to allow transfer of the dehumidified gas feedstream to a cryogenic unit. Various embodiments of desiccant cartridge 550 are described in greater detail in U.S. patent application Ser. No. 10/884,318 entitled "Desiccant Cartridge," filed on Jul. 1, 2004, the contents of which are hereby incorporated by reference in their entirety.

After passing through desiccant cartridge 550, the feed flow may optionally pass through a filter 552. In one embodiment, filter 552 is a ten micron filter. The feed flow may then enter the cryocooler 502 near the cryocooler 502/dewar 520 interface, through the feed flow tube 512. The feed flow passes by cold finger 508 and is liquefied, thereafter falling into dewar 520. Boiloff gas and/or a portion of the feed flow that has not been liquefied may create a vent flow (VVV) that may leave the dewar 520 and flow out of vent tube 514. The vent flow may next pass through a normally-open solenoid valve 556 and into a boiloff tube 560. From the boiloff tube 560, the gas exits the system to the atmosphere.

In one embodiment, boiloff tube 560 increases the safety of a liquefaction device. Even with use of a liquid oxygen barrier 118, liquid oxygen may still flow out of a dewar 520 if the dewar 520 is tipped over. The boiloff tube 560 may work in conjunction with the liquid oxygen barrier 118 to prevent liquid oxygen from spraying out of the vent port of a liquefaction apparatus upon tipping of the apparatus. Upon tipping, as liquid oxygen flows through the feed line 512 and vent line 514, its volume may expand by a ratio of about 800 times as it boils into gas which, in turn, may push the remaining liquid forward as pressure builds. Boiloff tube 560 may provide a volume in which the remaining liquid may drop out of the way to allow the gas to vent from the liquefaction apparatus without pushing liquid through the vent port and out of the system. This may, in turn, minimize potential human contact with a rapidly-expanding mixture of oxygen gas and liquid oxygen. In one embodiment, the boiloff tube 560 comprises a wide section of tubing that, when laying on its side, provides a section in which liquid may pool. Liquid pooled inside the boiloff tube 560 will boil off to gas and safely vent from the boiloff tube 560. In one embodiment, boiloff tube 560 is constructed with PVC pipe.

Figure 23:
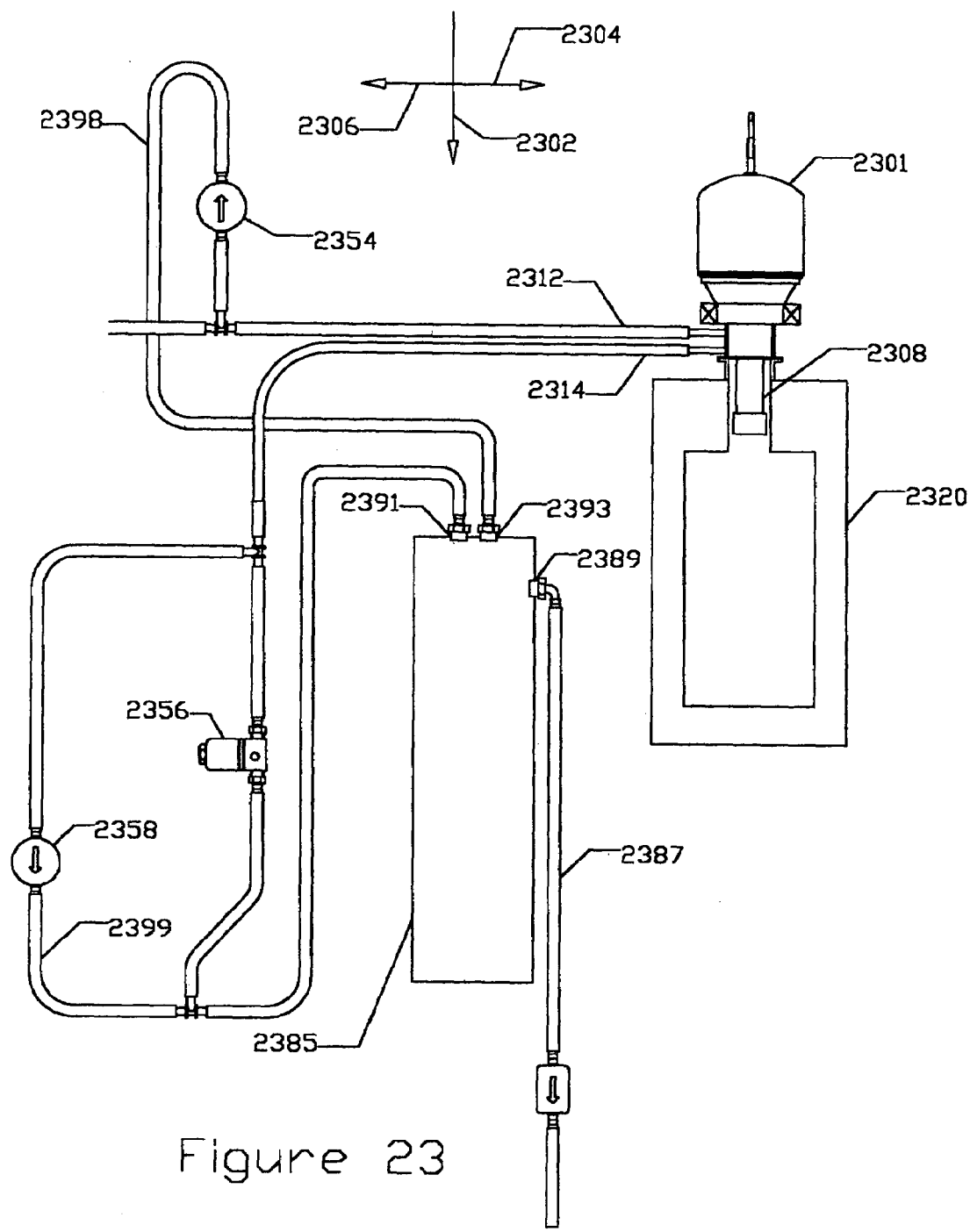
FIG. 23 depicts a partial view of a conceptual system diagram similar to the conceptual system diagram of FIG. 5, according to some embodiments of the present invention.

FIG. 23 depicts a partial view of a conceptual system diagram similar to the conceptual system diagram of FIG. 5, according to some embodiments of the present invention. As with FIGS. 5 and 6, although the configuration of elements in FIG. 23 does not necessarily depict the spatial relationship between elements such as scale or distance, FIG. 23 represents the directional orientation relationship between dewar 2320, cold finger 2308, cryocooler 2301, and boiloff vessel 2385. Boiloff vessel 2385 is an alternative embodiment. The "bottom" of boiloff vessel 2385 is the surface of boiloff vessel 2385 toward which liquid would be pulled by gravity; the location of the "bottom" may vary according to the orientation of boiloff vessel 2385. When dewar 2320 and boiloff vessel 2385 are in an upright position, the force of gravity acts in a direction similar to the direction of arrow 2302. In the upright position, liquid gas is contained at the bottom of dewar 2320, and vent gas (such as boiloff gas and/or non-liquefied feed flow gas) passes out of dewar 2320 and/or cryocooler 2301 through vent line 2314, through normally-open solenoid valve 2356, into boiloff vessel 2385, and out through boiloff vent 2387. According to some embodiments of the present invention, atmospheric gases, such as ambient air, may be prevented from entering boiloff vessel 2385, cryocooler 2301, and/or dewar 2320 through an open vent line, such as boiloff vent 2387, by maintaining a positive flow of feedstream gas through feed line 2312 to cold finger 2308.

Dewar 2320, cryocooler 2301, and boiloff vessel 2385 may be tipped and/or tilted into a least favorable position, in which gravity acts in a direction similar to the direction of arrow 2306. In such cases, liquid gas within dewar 2320 may contact parts of dewar 2320, cryocooler 2301, and/or cold finger 2308 that are at or warmer than the boiling point of the liquid gas, causing the liquid gas to evaporate and/or expand. This rapidly-expanding mixture of gas and liquid gas may pressurize the dewar, causing the rapidly-expanding mixture to quickly flow out of the dewar 2320/cryocooler 2301 interface through feed line 2312 and/or vent line 2314. In the least favorable position in which gravity acts in the direction 2306, gravity further pulls the liquid gas through the warm feed line 2312 and/or vent line 2314. The rapidly-expanding mixture that passes through feed line 2312 may be prevented from flowing back to concentrator 530 with a one-way check valve 544 or to compressor 646 with one-way check valve 648. Instead, the rapidly-expanding mixture that passes through feed line 2312 may flow through relief line 2395 through pressure relief valve 2354 and into boiloff vessel 2385 via opening 2393. The rapidly-expanding mixture that passes through vent line 2314 may pass through solenoid valve 2356 and into boiloff vessel 2385 via opening 2391. Alternatively, if solenoid valve 2356 is closed or if solenoid valve 2356 does not permit enough of the rapidly-expanding mixture to pass through, then the mixture may pass through relief line 2399 through pressure relief valve 2358 and into boiloff vessel 2385 via opening 2391. Opening 2389 opens to atmosphere; for example, opening 2389 opens from boiloff vessel 2385 to atmosphere via boiloff vent 2387.

As the rapidly-expanding mixture of gas and liquid gas enters boiloff vessel 2385 via opening 2391 and/or 2393, the liquid phase of the mixture of gas and liquid gas may settle to the bottom of boiloff vessel 2385, and the gas phase of the mixture of gas and liquid gas may exit boiloff vessel 2385 via opening 2389. According to some embodiments of the present invention, the mixture of gas and liquid gas may spray into boiloff vessel 2385 toward the side of boiloff vessel 2385 that opposes opening 2391 and/or 2393. According to some embodiments of the present invention, boiloff vessel 2385 has an elongated cylindrical shape, and opening 2389 may be placed in proximity to or near the end closest to hole 2391 and/or 2393. Such a configuration may permit boiloff vessel 2385 and/or dewar 2320 to be uprighted shortly after a tipping event without permitting the liquid within boiloff vessel 2385 to spray out of boiloff vent 2387 and/or hole 2389. According to some embodiments of the present invention, having opening 2389 near the end of boiloff vessel 2385 and near opening 2391 and/or opening 2393 may permit the greatest liquid capacity while keeping boiloff vessel 2385 size as small as possible. Depending on the shape and configuration of boiloff vessel 2385, and the positioning of holes 2391, 2393, and/or 2389, the size of boiloff vessel 2385 should be selected to accommodate the proper amount of liquid. For example, according to one embodiment of the present invention, the volume of boiloff vessel 2385 is approximately equal to one-third of the volume of liquid in the dewar corresponding to a full liquid level. As another example, if a liquid gas dewar holds approximately 1.5 liters of liquid gas, a boiloff vessel 2385 with a volume of approximately 0.5 liters may be used. Alternatively, the volume of boiloff vessel 2385 may be approximately equal to one-half of the volume of liquid in the dewar corresponding to a full liquid level, according to some embodiments of the present invention.

Dewar 2320, cryocooler 2301, and boiloff vessel 2385 may be tipped and/or tilted into a position in which gravity acts in a direction similar to the direction of arrow 2304. According to some embodiments of the present invention, in such cases the length of vent tube 2314 and/or vent tube 2387 may permit the liquid gas to boil off before any of it exits opening 2389 and/or boiloff vent 2387 in the liquid phase, particularly because gravity does not act in such cases to pull liquid gas down into feed flow line 2312 and/or vent line 2314. Dewar 2320, cryocooler 2301, and boiloff vessel 2385 may also be tipped and/or tilted into a position in which gravity acts in a direction perpendicular to the directions indicated by arrows 2302, 2304, 2306. In such cases, feed tube 2312 and flow tube 2314 may extend to the side and may permit a moderate volume of liquid gas to escape dewar 2320 with approximately half the volume of boiloff vessel 2387 available to contain the liquid gas while it boils off, while leaving a fluid path for vent gas to escape through opening 2389.

Although boiloff vessel 2385 is shown with openings 2391, 2393, and 2389, boiloff vessel 2385 may alternatively be configured with opening 2389 and either opening 2391 or opening 2393, according to various embodiments. Alternatively locating opening 2389 on an end of boiloff vessel 2385 opposite from opening 2391 and/or opening 2393 (such as depicted with boiloff vessel 560) may permit boiloff vessel 2385 to contain the liquid gas uniformly in any direction of tipover; however, locating opening 2389 on an end of boiloff vessel 2385 opposite from opening 2391 and/or opening 2393 may result in liquid gas traveling out of boiloff vent 2387 when boiloff vessel 2385 is uprighted directly following a tipover event.

Although openings 2391, 2393, and 2389 are depicted as small holes sized to accommodate flow through a tube, openings 2391, 2393, and/or 2389 may be varied in size and shape. According to some embodiments of the present invention, multiple boiloff vessels may be used. Although boiloff vessels 560, 660, 2385 are depicted as cylinders, boiloff vessels according to embodiments of the present invention may be any shape that permits holding or enclosure of a volume of cryogenic liquid; for example, boiloff vessels according to embodiments of the present invention may be, but are not limited to, spheres, cubes, boxes, U-shaped volumes, cylinders, semi-spheres, semi-cylinders, pyramids, cones, semi-pyramids, semi-cones, and/or toroids. According to some embodiments of the present invention, a boiloff vessel surrounds a portion or all of dewar 2320; such a boiloff vessel configuration may save space in some cases. Based on the disclosure provided herein, one of ordinary skill in the art will appreciate a number of different possible shapes, sizes, and configurations of boiloff vessels according to various embodiments of the present invention.

Figure 6:
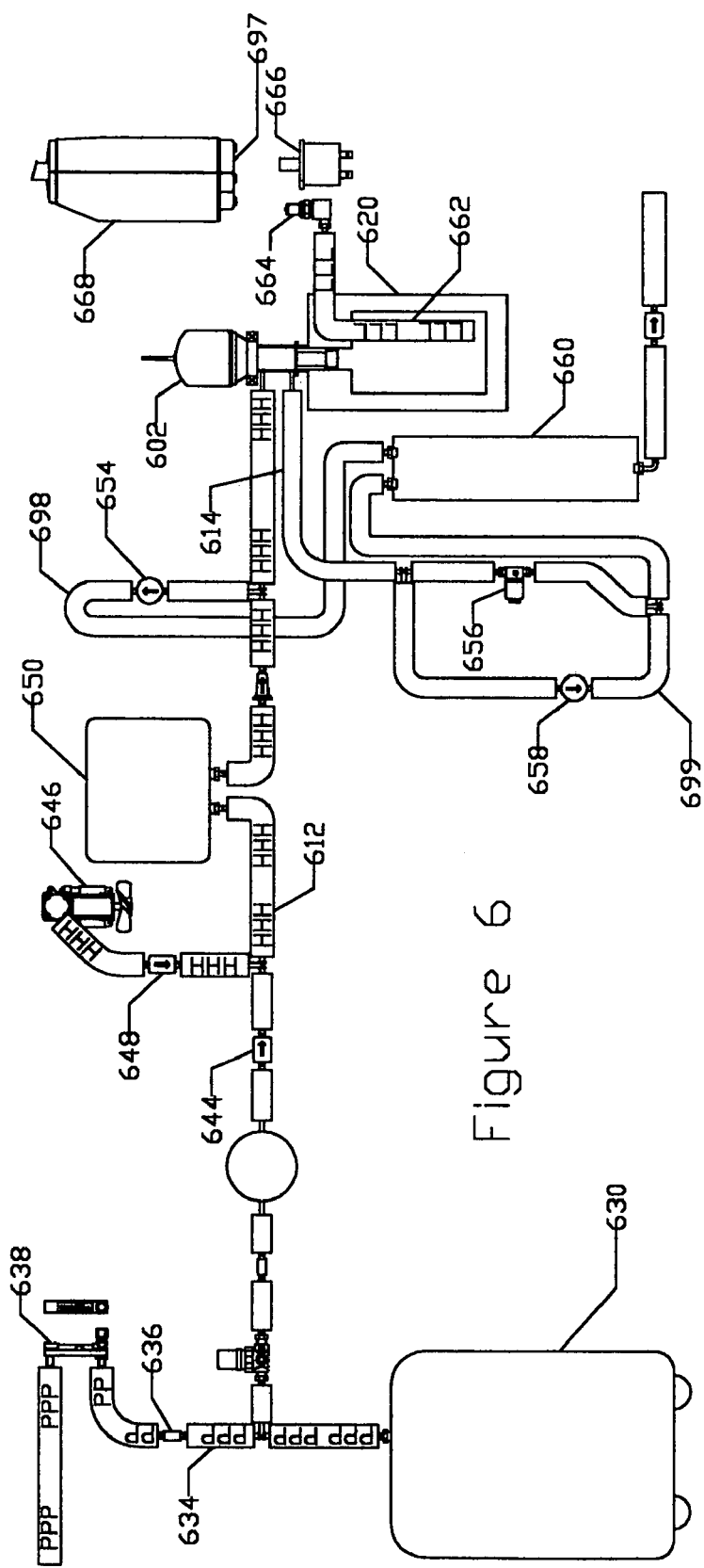
FIG. 6 depicts a conceptual system diagram of one embodiment of the present invention coupled to an oxygen concentrator, illustrating liquid flow during a transfill cycle.

FIG. 6 illustrates a system similar to the system of FIG. 5, during a transfill cycle according to embodiments of the present invention. In one embodiment, a compressor 646 is used to pressurize the dewar 620 and thus the feed line 612 in order to perform a transfill of liquid oxygen from dewar 620 to portable stroller 668. To commence transfill, compressor 646 is turned on. In FIG. 6, "PPP" refers to the presence of patient gaseous oxygen flow, "HHH" refers to the presence of gas flow, such as ambient air flow, from compressor 646, and "LLL" refers to the presence of liquid gas flow, such as liquid oxygen flow.

In order to keep the system pressure low in the dewar 620 during liquid oxygen production, the vent line 614 is open to atmosphere. Backflow of ambient air into the dewar 620 is avoided by maintaining a slightly positive flow of gaseous oxygen to the cryocooler 602, and by including a one-way check valve 599 in the vent line 614. However, transfill of liquid oxygen requires an elevated pressure in the dewar 620. Therefore, a normally-open solenoid valve 656 is closed during transfill in order to permit a pressure buildup inside dewar 620. A transfill tube 662 connects a transfill valve 664 outside the dewar 620 to the inside of the dewar 620; one end of transfill tube 662 extends within dewar 620, another end extends outside of dewar 620. In one embodiment, transfill tube 662 is made of metal and passes through the two walls and vacuum space of an insulated dewar 620.

Compressor 646 draws in ambient air, compresses it, and sends it through one-way check valve 648. Check valves 644, 648 substantially prevent compressed air from backing up into the compressor 646, into the concentrator 630, or into the patient flow. For example, check valve 644 may not only prevent a backflow into the concentrator 630 during liquefaction or transfill, but may also prevent an over-feed of the patient supply 634. Check valve 544 may perform similar functions. During transfill, flow of gaseous oxygen from the concentrator 630 continues to pass through patient flow line 634, through patient orifice 636, and through patient flowmeter 638. As compressor 646 continues to draw ambient air into the feed line 612, a space above the liquid in the dewar becomes pressurized, creating a downward force on the top of the liquid that pushes liquid out of the dewar 620 and into the transfill tube 662. The liquid then passes through transfill valve 664 into a portable oxygen stroller 668.

In addition to compressor 646, other means may be used to pressurize dewar 620 for a transfill process. For example, a heater may be placed within dewar 620 to boil oxygen until enough pressure builds up in dewar 620 to push liquid from dewar 620 through transfill tube 662. As another example, a heat source may be situated near, but not inside, of dewar 620, such that enough heat may be supplied through the heat source to build pressure within dewar 620. As yet another example, a vaporizer loop or controllable heat leak may be used to raise the pressure within dewar 620 for a transfill process.

In one embodiment, the transfill process begins when the stroller 668 is aligned with the transfill valve 664 and pushed onto the transfill valve 664; a transfill switch 666 may be configured to activate when the stroller 668 is engaged with the transfill valve 664. According to some embodiments of the present invention, transfill switch 666 is a push-button switch that may be pushed or pressed by a valve interface surface 697 of portable stroller 668 when portable stroller 668 has been engaged with valve 664. According to other embodiments, transfill switch 666 is a proximity detection switch configured to trigger when the portable stroller 668 is close enough to valve 664 to be engaged with valve 664. Transfill switch 666 may activate compressor 646 and close solenoid valve 656. In one embodiment, the transfill of liquid oxygen to a portable stroller may be activated through a state change on the input of a programmable logic device, which may operate to activate the compressor 646, close the solenoid valve 656, monitor the time since transfill began, and terminate the transfill after a predetermined time. This may prevent an over-emptying of the dewar 620 and may minimize overfilling of the portable stroller 668 during transfills, in which the stroller 668 sometimes freezes to the transfill valve 664 and prevents a user from manually ending the transfill process by removing the stroller 668 from the transfill valve 664 and transfill switch 666.

In one embodiment, portable stroller 668 is a USP93 approved stroller. The stroller 668 is a device that a patient uses to carry liquid oxygen. Oxygen concentrators are currently approved for USP93 oxygen, but they produce gaseous oxygen. Oxygen in a liquid form may appeal most to a patient because liquid is the most convenient state of oxygen for portable use. A patient can carry a greater amount of oxygen in a smaller and lighter container than would exist for a comparable amount of gaseous oxygen. Portable stroller 668 may boil off liquid oxygen at a prescribed rate to provide a flow of breathable oxygen to a patient.

In one embodiment, pressure relief valves 654, 658 prevent an over-pressurization of the dewar 620. Relief valve 654 connects feed line 612 to boiloff tube 660, and relief valve 658 connects vent line 614 to boiloff tube 660. Alternatively, pressure relief valve 654 may be placed inline with a pressure relief line 698, the pressure relief line 698 having a first end in fluid communication with the feed line 612, and having a second end in fluid communication with boiloff tube 660. In one embodiment, pressure relief valve 654 can be configured to open when pressure in the feed line 612 equals a predetermined pressure, such as twelve PSIG, with a tolerance of 10%, thereby permitting the high pressure fluid to flow out of feed line 612, through pressure relief line 698, and into boiloff tube 660. In some embodiments, pressure relief valve 658 may be placed inline with a pressure relief line 699. Pressure relief line 699 may have a first end in fluid communication with vent line 614, and a second end in fluid communication with boiloff tube 660. Alternatively, the second end of pressure relief line 699 may also be in fluid communication with vent line 614. For example, in embodiments in which vent line 614 comprises solenoid valve 656, pressure relief line 699 may simply bypass solenoid valve 656 in vent line 614. In one embodiment, pressure relief valve 658 can be configured to open when pressure in the vent line 614 exceeds a predetermined pressure, such as twelve PSIG, with a tolerance of 10%, thereby permitting the high pressure fluid to flow out of vent line 614, through pressure relief line 699, and into boiloff tube 660.

Figure 29:
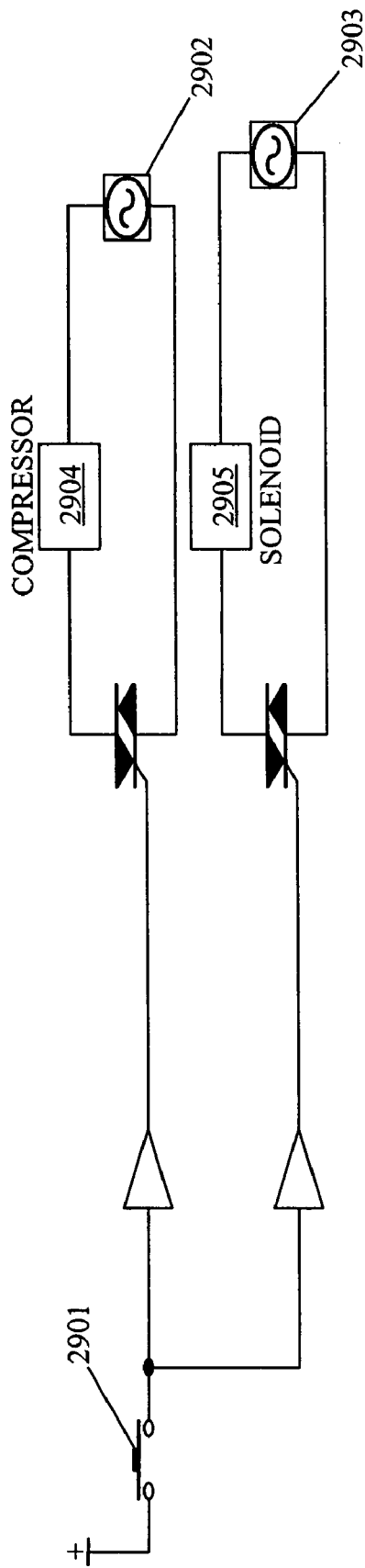
FIG. 29 depicts a conceptual wiring diagram for a transfill switch for completing a compressor power circuit and/or a solenoid power circuit, according to various embodiments of the present invention.

FIG. 29 depicts a conceptual wiring diagram for a transfill switch 2901 for completing a compressor 2904 power circuit supplied by source 2902 and/or a solenoid 2905 power circuit supplied by source 2903, according to various embodiments of the present invention. Compressor 2904 is normally off during liquefaction. Solenoid valve 656 is normally open, but may be closed during transfill in order to permit a pressure buildup inside dewar 620. Transfill switch 2901 may be depressed, for example, with the bottom of a portable stroller or portable dewar as it is engaged with a transfill valve; transfill switch may then complete the compressor 2904 circuit and/or the solenoid 2905 circuit.

Figure 30:
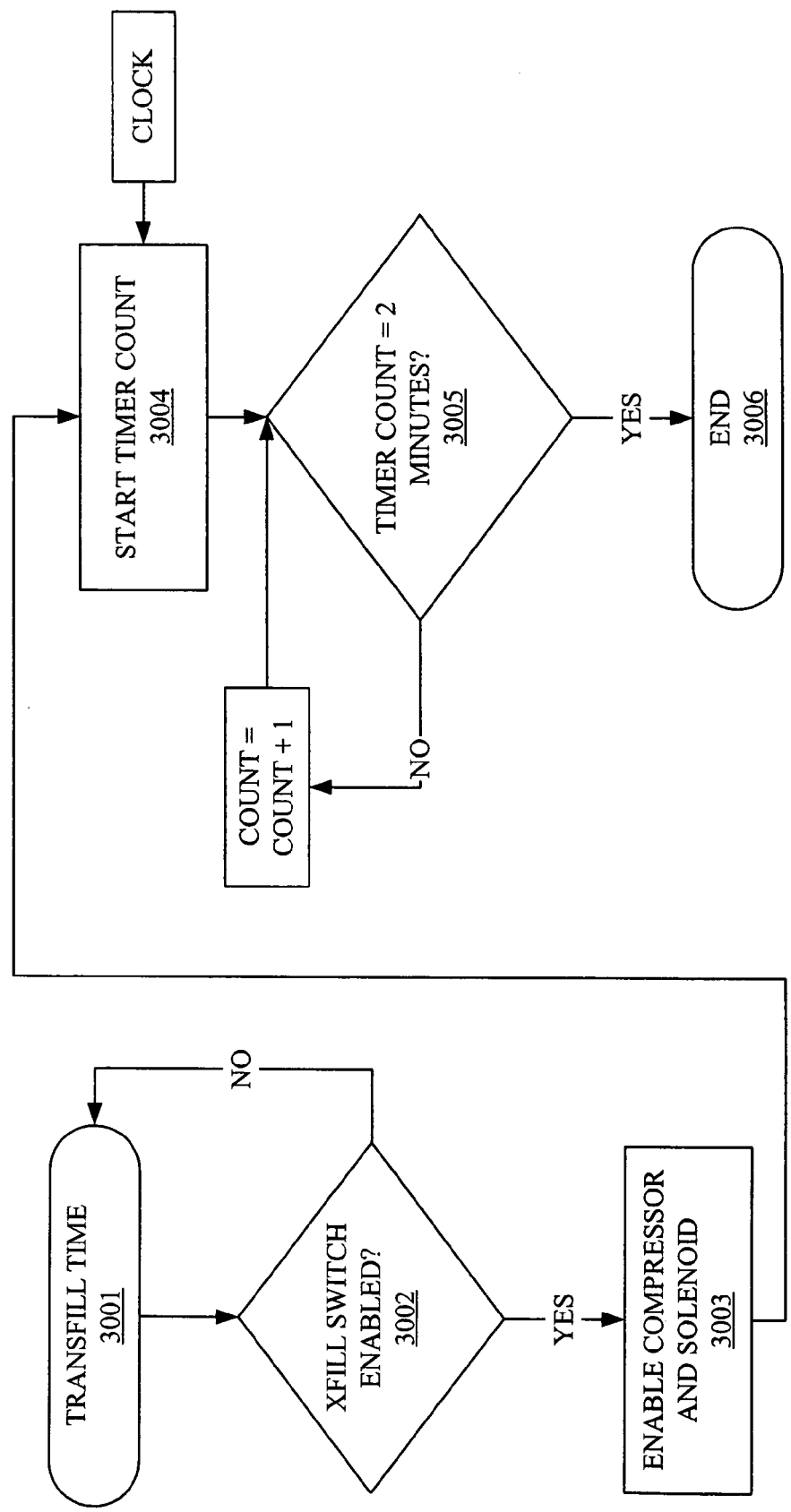
FIG. 30 depicts a transfill time-out flow chart, according to various embodiments of the present invention.

FIG. 30 depicts a transfill time-out flow chart, according to various embodiments of the present invention. In one embodiment mentioned above, the transfill of liquid oxygen to a portable stroller may be activated through a state change on the input of a programmable logic device, which may operate to activate the compressor 646, close the solenoid valve 656, monitor the time since transfill began, and terminate the transfill after a predetermined time. Various devices may be used to implement elements of the flow diagram of FIG. 30; for example, such devices include, but are not limited to, a microcontroller and/or processor, discrete hardware semiconductors, and/or programmable logic devices. According to some embodiments of the present invention, a method may be used to stop the transfill process after a predetermined time to prevent over-filling of a portable stroller or portable dewar. A transfill timing process begins at block 3001. A determination is made whether the transfill switch is enabled (block 3002). If the transfill switch is not enabled, the process continues just before block 3002. If the transfill switch is enabled, then the compressor and solenoid are enabled (block 3003), as described with reference to FIG. 29, above. A timer count is started (block 3004), using a clock in some embodiments. A determination is made whether the timer count equals a predetermined count (block 3005); for example, a determination is made whether the timer count equals two minutes. As another example, the predetermined count may equal one minute and forty seconds. The predetermined count or predetermined time may be any time based on the expected volume of container to be filled and/or the flow rate of liquid gas into the container. Any such predetermined time may also take into account the fact that during the beginning of a transfill process, no liquid gas is transferred between the dewar and the portable stroller because the liquid gas initially boils off in making the transfill apparatus cold enough to convey the liquid gas. If the timer count does not equal the predetermined count, then the timer count is positively incremented and the process returns to a point just before block 3005. If the timer count equals the predetermined count, then the transfill time process ends (block 3006).

Figure 13:
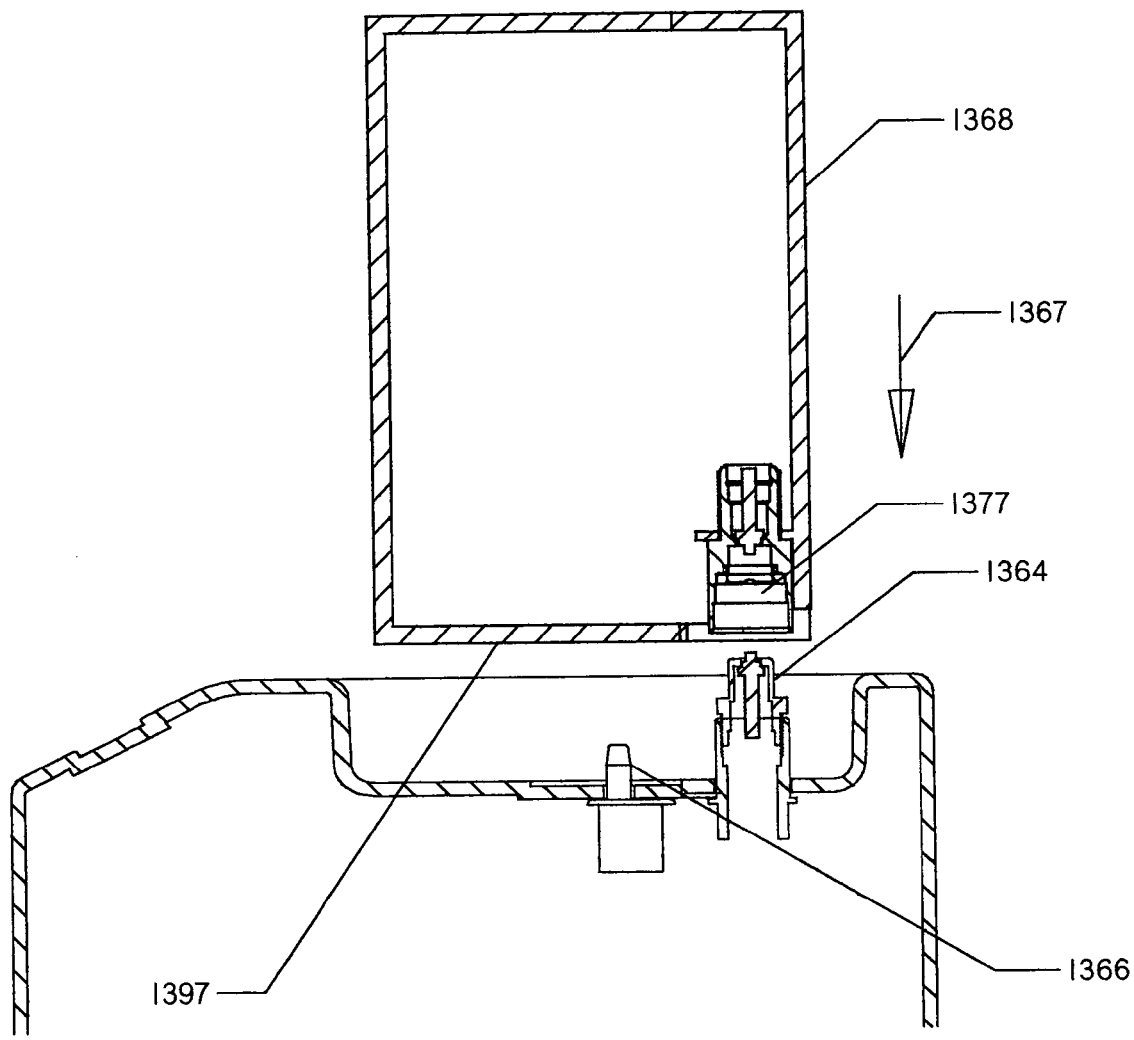
FIG. 13 depicts a partial cross-sectional view of the outer housing with a transfill valve and a transfill switch, and a portable stroller with a female valve, according to one embodiment of the present invention.

FIG. 13 illustrates a portable stroller 1368 interface according to some embodiments of the present invention. In one embodiment, the transfill process begins when female valve 1377 on stroller 1368 is aligned with the transfill valve 1364 and pushed onto the transfill valve 1364 in the direction indicated by arrow 1367; a transfill switch 1366 may be configured to activate when a female valve 1377 on the stroller 1368 is engaged with the transfill valve 1364. According to some embodiments of the present invention, transfill switch 1366 is a push-button switch that may be pushed or pressed by a valve interface surface 1397 of portable stroller 1368 when female valve 1377 of portable stroller 1368 has been engaged with valve 1364.

Figure 24:
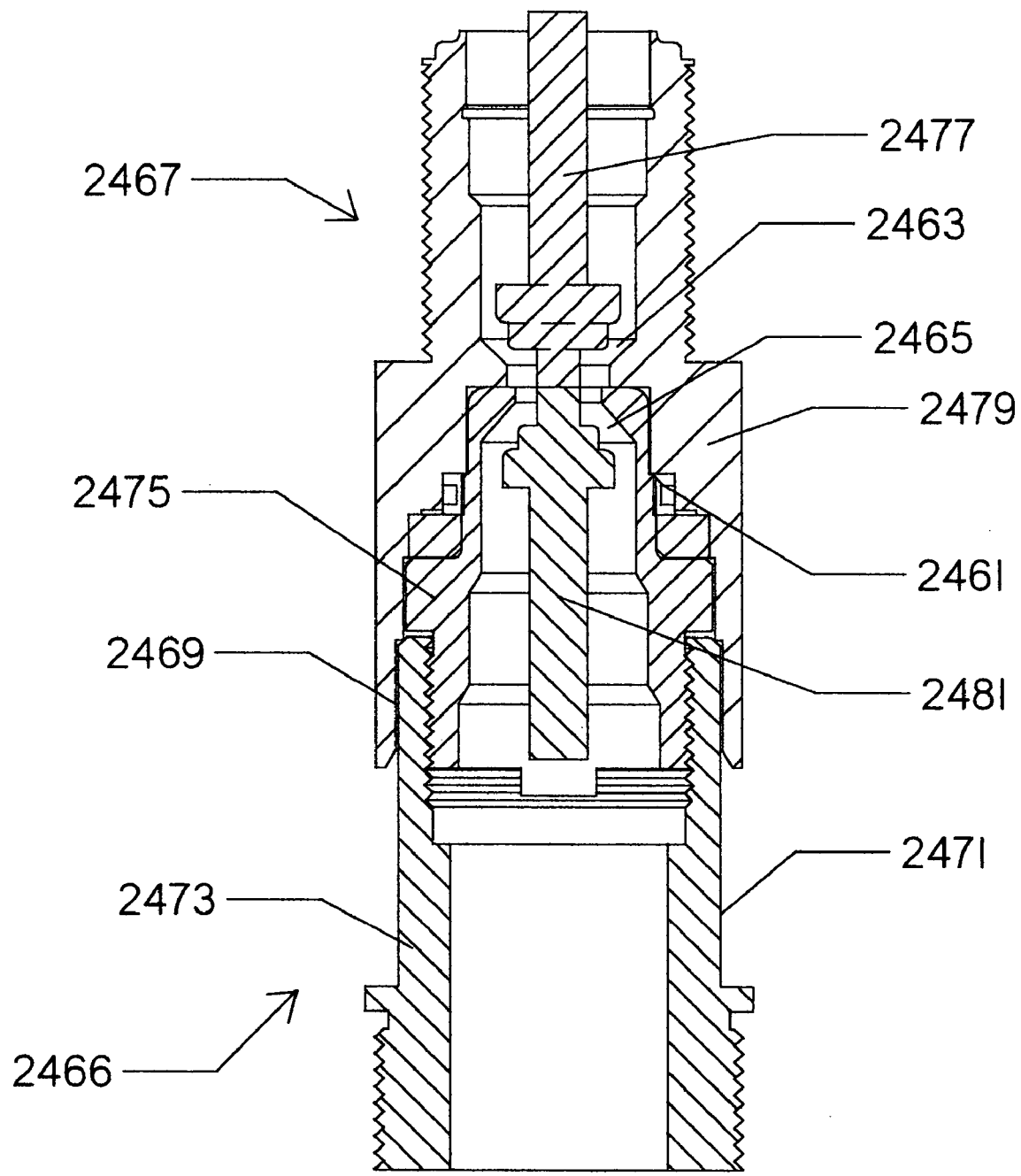
FIG. 24 illustrates a partial cross-sectional view of a male transfill valve and female valve interface, according to some embodiments of the present invention.

FIG. 24 illustrates a partial cross-sectional view of a male transfill valve 2466 and female valve 2467 interface, according to some embodiments of the present invention. A gas liquefaction device may have mounted therein a valve mount 2473 in fluid communication with a transfill tube, such as a tube extending between valve mount 2473 and a dewar operable to contain a liquid gas. According to some embodiments of the present invention, valve mount 2473 may have a threaded inner diameter onto which a valve body 2475 having a threaded outer diameter may be attached. Valve body 2475 may include a fluid passage 2465 through which fluids such as liquid oxygen may flow. A valve stem 2481 may be situated within fluid passage 2465 and configured to close fluid passage 2465 until depressed. One or more springs (not shown) may be used to bias valve stem 2481 in a closed position. Female valve 2467 may include a valve body 2479 having a threaded outer diameter, for example, in order to be attached to a portable stroller. Female valve 2467 may also include a fluid passage 2463 and a valve stem 2477, the valve stem 2477 being situated within fluid passage 2463 and configured to close fluid passage 2463 until depressed. Valve stem 2477 may also be biased in a closed position via one or more springs (not shown). When a portable stroller comprising female valve 2467 is interfaced with a portable use liquefaction device having a transfill valve 2466, female valve 2467 may be pressed onto transfill valve 2466 to press valve stem 2481 into valve stem 2477, thereby opening fluid passage 2465 and fluid passage 2463 as shown in FIG. 24 to allow liquid gas, such as liquid oxygen, to flow from a dewar into a portable stroller. According to some embodiments of the present invention, a Teflon ring 2461 may be used between female valve 2467 and transfill valve 2466 to temporarily seal the valve interface while valve 2467 is pressed onto valve 2466, to prevent leakage of liquid gas during a transfill process.

As an additional safety measure, transfill valve 2466 and/or female valve 2467 may be specially adapted to be incompatible with traditional USP transfill valves. USP transfill valves may be used to transfer USP 99% purity liquid oxygen from a dewar to a portable stroller; however, government regulatory entities may require that USP93 approved strollers be incompatible with USP transfill valves. One embodiment of a solution to such a problem is made possible by the existence of a de facto standard valve interface for USP portable strollers. Such a possible solution involves creating a valve mount 2473 having an outer diameter 2471 greater than an inner diameter of a standard USP valve interface, such that the standard USP valve interface of a USP portable stroller does not fit over the valve mount 2473 and cannot depress valve stem 2481 of a USP93 oxygen liquefaction device. A USP93 stroller may be configured with a female valve 2467 adapted with a larger inner diameter 2469 to fit over valve mount 2473 and/or valve body 2475. Another embodiment of a solution for making transfill valve 2466 incompatible with a USP portable stroller may involve making the protruding male portion of valve 2466, such as valve body 2475, shorter than a female cavity of a USP portable stroller valve, such that pushing a USP portable stroller valve onto transfill valve 2466 would not bring the valve stem of the USP portable stroller close enough to valve stem 2481 to open either fluid passage 2463 or fluid passage 2465. According to some embodiments of the present invention, although a portable stroller with a standard USP valve would not fit over transfill valve 2466, a portable stroller with female valve 2467 could be configured to fit over transfill valve 2466 and/or a standard USP transfill valve. Based on the disclosure provided herein, one of ordinary skill in the art will recognize a variety of ways in which transfill valve 2466 and/or female valve 2467 may be configured and/or modified to be incompatible with a corresponding USP (99% purity) approved valve.

With reference to FIG. 1, cryocooler 102 and dewar 120 interface at cryocooler flange 104 and dewar flange 116. An O-ring 106 may be placed between dewar flange 116 and cryocooler flange 104 to create a seal between dewar flange 116 and cryocooler flange 104. The O-ring 106 may be made with silicon. A cold finger 108 having a cold head 110 extends from cryocooler 102 down into the dewar 120. A feed flow of concentrated oxygen gas enters a feed tube 112 and is liquefied at the cold head 110, then falls into dewar 120. Boiloff gases from dewar 120 exit through vent tube 114. A liquid oxygen barrier 118 may be situated between dewar 120 and cryocooler 102 in order to control the flow of gas and expanding liquid when the dewar 120 is tipped onto its side.

Some prior gas liquefaction devices have typically employed complex and/or expensive condenser structures attached to a cold head of a cryocooler. It has previously been thought advantageous to force a feed gas stream across a cold surface enclosure in order to improve liquefaction efficiency. It has also previously been thought advantageous to employ a cooled structure, such as a double-walled condenser structure attached to a cold surface of the cryocooler, and to direct the feed gas through the condenser structure to increase surface area over which liquefaction occurs. However, embodiments of the present invention simply employ a cold finger 108 structure with a cold head 110, at which oxygen gas liquefies. Instead of forcing a feed stream of gas onto cold finger 108, or through a high-surface area condensing structure, embodiments of the present invention permit oxygen gas to be introduced in the vicinity of cold finger 108 through feed line 112. Due to the very cold temperatures produced by cold finger 108, a low pressure area is created at the surface of cold finger 108; this low pressure area, or "cold pressure," draws the feed stream of gas toward cold finger 108 for liquefaction. Utilizing this concept in embodiments of the present invention reduces cost and complexity by eliminating a condenser structure, particularly a complex or double-walled or spiraled condenser structure.

Although flow director portion 2065 of liquid oxygen barrier 2061 may surround cold head 110 of cold finger 108, or may stop short of cold head 110, as described below with reference to FIGS. 20 and 21, flow director portion 2065 merely directs the flow of gaseous oxygen and other gases, and is not a condenser, according to various embodiments of the present invention. Flow director portion 2065 may direct incoming gas through an inside of flow director portion 2065, causing it to remain in the vicinity of cold finger 108 and/or cold head 110. Outgoing gas, or vent gas, such as vent gas from dewar 120, may pass along an outside of flow director portion 2065 as it exits through vent line 114. A smaller opening between cold head 2110 and flow director portion 2065 may permit liquid oxygen to drip out after liquefaction, while a larger opening on the outside of flow director portion 2065 may permit gases, such as vent gases, to exit the dewar. Thus, flow director portion 2065 serves to direct gas flow according to some embodiments of the present invention. According to some embodiments of the present invention, flow director portion 2065 may also serve to prevent liquefaction of ambient air directly following a transfill process.

For many of the same reasons that embodiments of liquefaction systems depicted in FIG. 1 do not require complex and/or expensive condenser structures, so, too, embodiments of liquefaction devices depicted in FIG. 1 may also reduce liquefaction cost by seeking to maintain the oxygen purity of incoming gas, rather than seeking to maximize oxygen purity of incoming gas. Embodiments of the present invention depicted in FIG. 1 may produce liquid oxygen with an oxygen purity approximately at or just above the oxygen purity of the incoming feed stream supply of oxygen gas. This may be achieved, for example, by fixing the flow rate of the feed stream of oxygen from concentrator 530, using regulator 540 and orifice 542, and by maintaining the cold finger 108 at a substantially constant temperature at or below the liquefaction temperature of oxygen. Many oxygen concentrators output oxygen gas with a USP93 purity. Embodiments of the present invention therefore liquefy a feed flow of USP93 oxygen gas to maintain purity by creating liquid oxygen with a USP93 purity, rather than liquefying a feed stream of USP93 gas to maximize liquefaction purity. Such maximization often requires more complex controllers and hardware, often greatly increases the cost of oxygen liquefaction for small-scale home or office use, and therefore stands as a common drawback associated with prior art devices. The efficient and effective maintenance of oxygen purity achieved by various embodiments of the present invention is made possible at least in part by the particular designs, structures, operations, and placements of cryocooler 102, dewar 120, feed line 112, vent line 114, cold finger 108, and other liquefaction-related structures of embodiments of the present invention.

Once a liquefaction system according to embodiments of the present invention achieves equilibrium, there is a constant load on the cryocooler 102 due to the constant flow of gas to be liquefied, and constant thermal losses of the system. Because power to the cryocooler 102 also remains constant, the cold finger 108 may remain at a substantially constant temperature until the dewar 120 is full. If all of the feed stream of gas were liquefied, oxygen purity of the liquefied gas would remain the same as the oxygen purity of the feed stream of gas. However, such systems may maintain or slightly improve oxygen purity of the liquefied gas compared to the purity of the feed flow of gas for the following reasons: the three primary components of air have the following boiling points (liquefaction temperature): oxygen 90.2° K, argon 87.3° K, and nitrogen 77.4° K. Even at a cold finger 108 tip temperature colder than 77° K, if a positive feed flow is maintained, not all of the feed stream of gas will be liquefied and a slightly greater relative percentage of oxygen will liquefy versus argon and nitrogen. If the equilibrium temperature of such liquefaction systems is 87° K, then only oxygen and argon would liquefy. A similar phenomenon may also occur after liquefaction with preferential boiloff due to the different boiling point temperatures of these three gasses. Because oxygen has a higher boiling point temperature than argon or nitrogen, a slightly lower percentage of oxygen boils off due to dewar 120 thermal inefficiencies. Even though preferential boiloff continues to occur after the liquid gas is transferred from the storage dewar 120 in the liquefaction device to the portable dewar from which a patient may breathe, the product gas will still maintain a purity at or greater than the initial feed gas prior to liquefaction. This is due to the preferential liquefaction, and the preferential boiloff during storage and transfer that has already taken place increasing the liquid purity prior to a patient's breathing of the gas from the liquid portable stroller.

When a liquefaction device with an insulated dewar 120 tips over onto its side with a dewar 120 full of liquid oxygen, the liquid oxygen can flow out of the mouth of the dewar 120 into the cryocooler flange 104. This area may be very warm with a large mass of metal, and may provide direct access to the feed tube 112 and vent tube 114. The sudden warming of the liquid oxygen may cause the liquid to quickly boil resulting in a rapid volumetric expansion. This rapid expansion may force liquid oxygen along with gaseous oxygen through the feed tube 112 and vent tube 114 and may result in a spray of liquid oxygen out of a vent port of the liquefaction device.

A liquid oxygen barrier 118 may be configured to significantly slow down the rate at which liquid oxygen escapes from the insulated dewar 120 during a tipping event. The liquid oxygen barrier 118 reduces the size of the opening out of which liquid oxygen may escape during tipping. The liquid oxygen barrier 118 may have a diameter smaller than a diameter of the cryocooler flange 104, or the dewar flange 116, or both. The liquid oxygen barrier 118 may be a separate piece inserted between the cryocooler flange 104 and the dewar flange 116, or may be inserted into the cryocooler flange 104 only, or may be inserted into the dewar flange 116 only. Alternatively, the liquid oxygen barrier 118 may be integrated into either the cryocooler flange 104 or the dewar flange 116.

Figure 3:
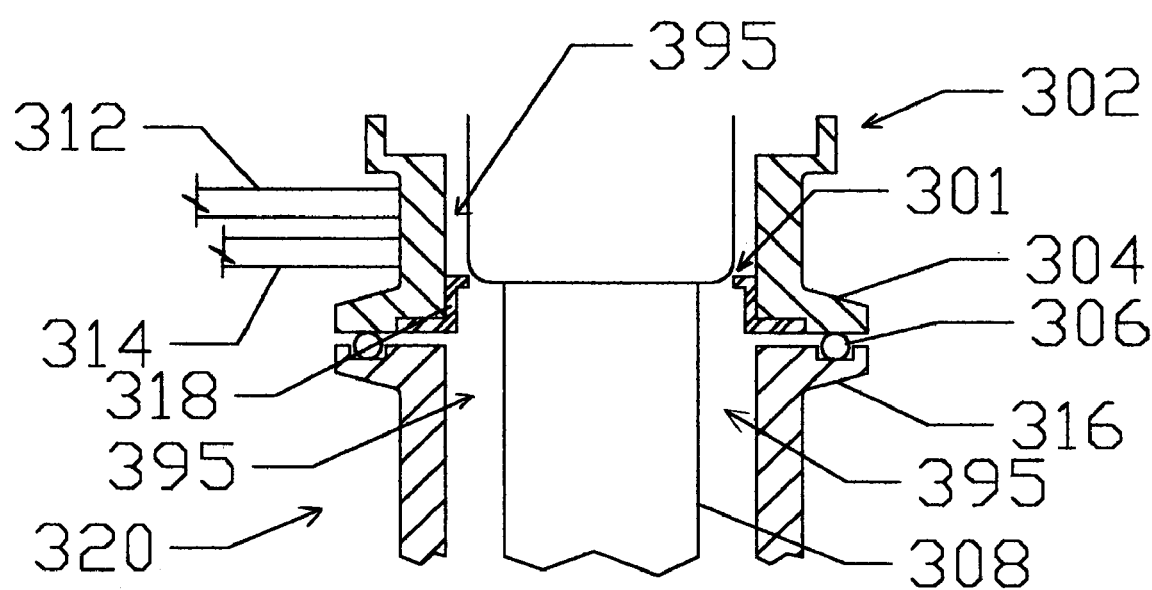
FIG. 3 depicts a cross-section, cut-away view of one embodiment of a liquid oxygen barrier situated within the cryocooler and dewar interface of one embodiment of the present invention.

FIG. 3 depicts a liquid oxygen barrier 318 inserted between cryocooler flange 304 and dewar flange 316. O-ring 306 helps to create a seal between cryocooler flange 304 and dewar flange 316. Concentrated gas enters feed tube 312 prior to liquefaction; boiloff gas from dewar 320 leaves through vent tube 314. Although the liquid oxygen barrier 318 may allow a building pressure to vent upon tipping of the dewar 320, the pressure is allowed to vent at a controlled and safe rate. In one embodiment, the liquid oxygen barrier 318 restricts an opening, around cold finger 308, between the dewar 320 and the cryocooler 302 to a smaller opening 301 of which the difference between an inner diameter and an outer diameter of the smaller opening 301 is approximately ten to fifteen thousandths of an inch. Smaller opening 301 may be located within an annular channel 395, the annular channel formed or defined by the cryocooler flange 304 and/or dewar flange 316 on an outer side, and by the cold finger 308 and/or cryocooler 302 on an inner side, as depicted in FIG. 3. Alternatively, annular channel 395 may be formed or defined by the cryocooler 302 and/or dewar 320 on an outer side, and by the cold finger 308 and/or cryocooler 302 on an inner side, as depicted in FIG. 3. Barrier 318 may serve to narrow the width of annular channel 395, and/or reduce the cross-sectional area of annular channel 395, such as at smaller opening 301. With barrier 318 in place, gas is still permitted to flow between the cryocooler 302 and the dewar 320; however, when the dewar 320 is tipped or tilted, barrier 318 may serve to decrease the rate at which a rapidly-expanding mixture of gas and liquid gas is permitted to exit the dewar 320 into the cryocooler 302. In a preferred embodiment, the liquid oxygen barrier 318 may be constructed with Teflon.

According to some embodiments of the present invention, barrier 318 may be positioned, inserted, or interposed between cryocooler flange 304 and dewar flange 316; in such embodiments, clamping element 1831, 1931 (see FIG. 18, for example) may secure barrier 318 in place while simultaneously clamping cryocooler flange 304 and dewar flange 316 together over O-ring 306. In other embodiments, barrier 318 may be integral with cryocooler 302, dewar 320, and/or cold finger 308. FIG. 19 also depicts a side perspective, cut-away view of an inside of a cryocooler and dewar interface of one embodiment of the present invention, showing one embodiment of a cold finger and a liquid oxygen barrier 1918.

Figure 20:
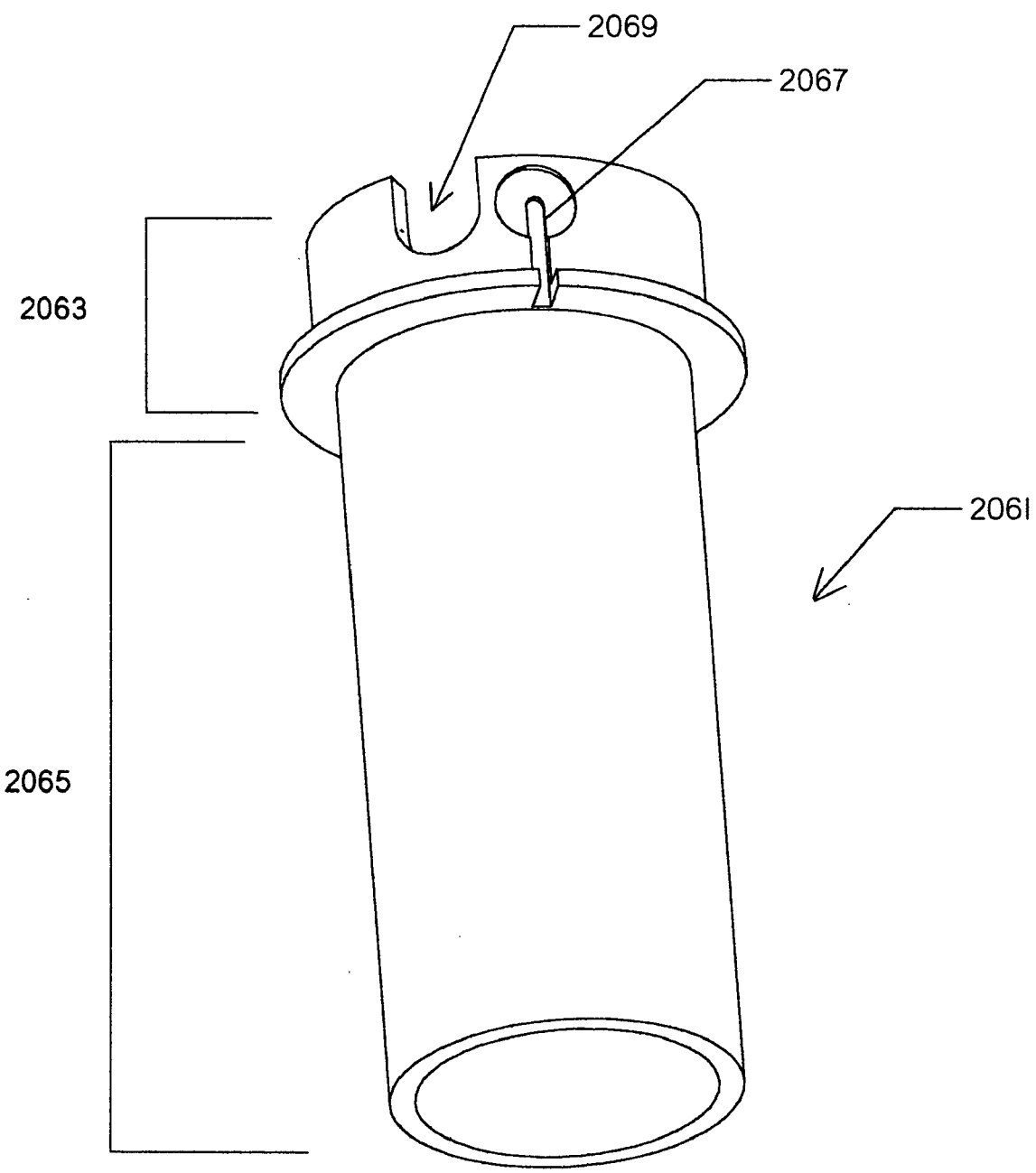
FIG. 20 depicts a side perspective view of a liquid oxygen barrier and flow director, according to one embodiment of the present invention.
Figure 21:
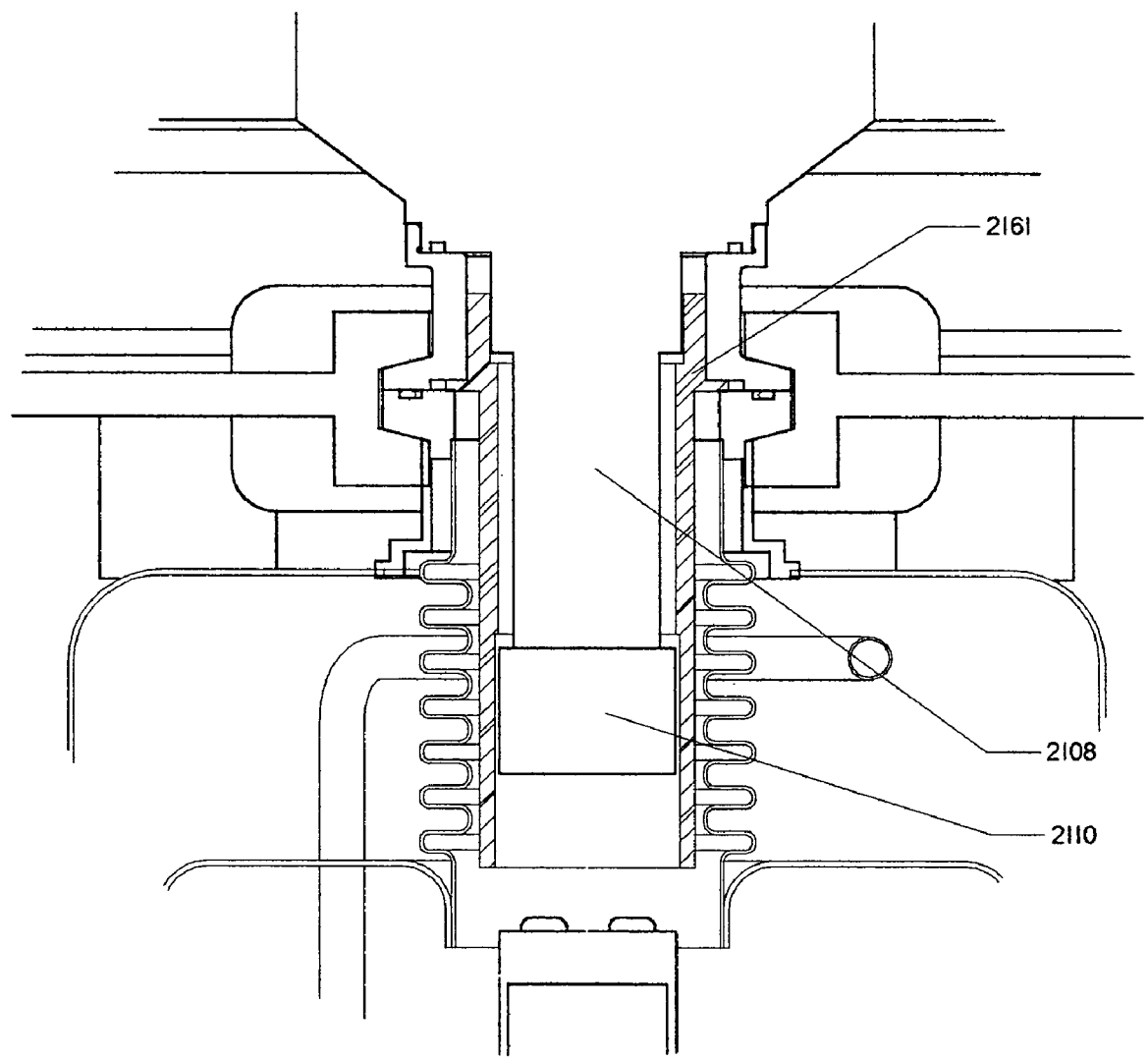
FIG. 21 depicts a side perspective, cut-away view of an inside of a cryocooler and dewar interface of one embodiment of the present invention, showing an embodiment of a cold finger and a liquid oxygen barrier and flow director.

Referring to FIGS. 20 and 21, an alternative embodiment of a liquid oxygen barrier 2061 is shown. Liquid oxygen barrier 2061, 2161 comprises a liquid oxygen barrier portion 2063 and a flow director portion 2065. Flow director portion 2065 extends the length of a cold finger 2108. Flow director portion 2065 may alternatively extend the length of a cold finger 2108 including a cold head 2110. Flow director portion 2065 may be tubular; alternatively, flow director portion 2065 may be of any shape that surrounds the cold finger 2108 and directs a feed gas flow from the feed line 512 towards the cold head 2110. In some embodiments, liquid oxygen barrier 2061, 2161 may be constructed with a Teflon material. Feed flow enters from a feed flow line 512 through opening 2069 and flows inside of the flow director portion 2065 toward the cold head 2110. Vent gas flows along the outside of the flow director portion 2065 and out to the vent line 514 through opening 2067. The liquid oxygen barrier portion 2063, though of a different configuration in order to allow feed gas to flow inside and vent gas to flow outside, performs the same function as the liquid oxygen barriers 118, 318, 1918 in preventing excessive leakage of liquid and gaseous oxygen during a tipping event.

Figure 9:
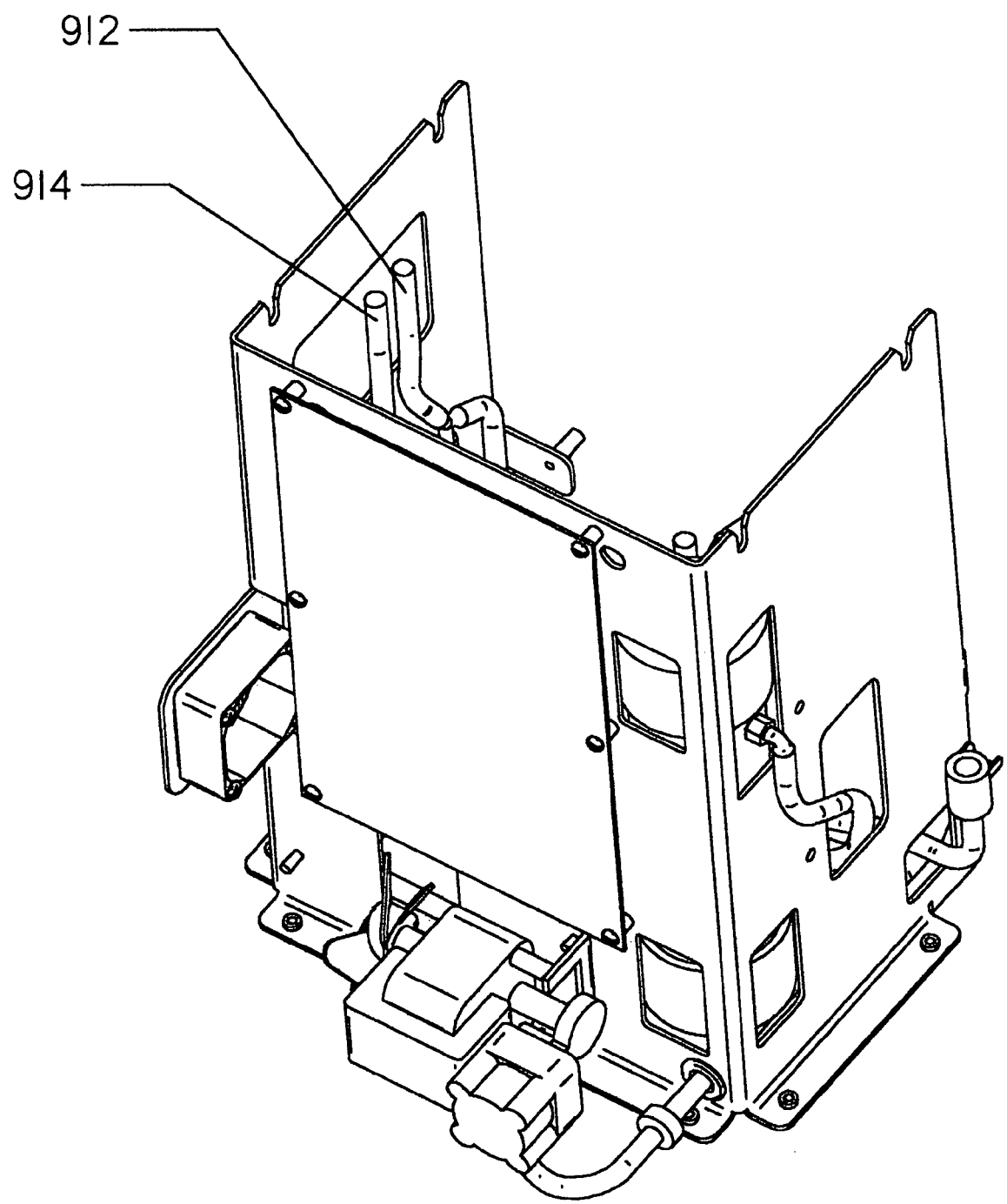
FIG. 9 depicts a perspective view of a lower chassis assembly of a liquefaction device according to one embodiment of the present invention.
Figure 10:
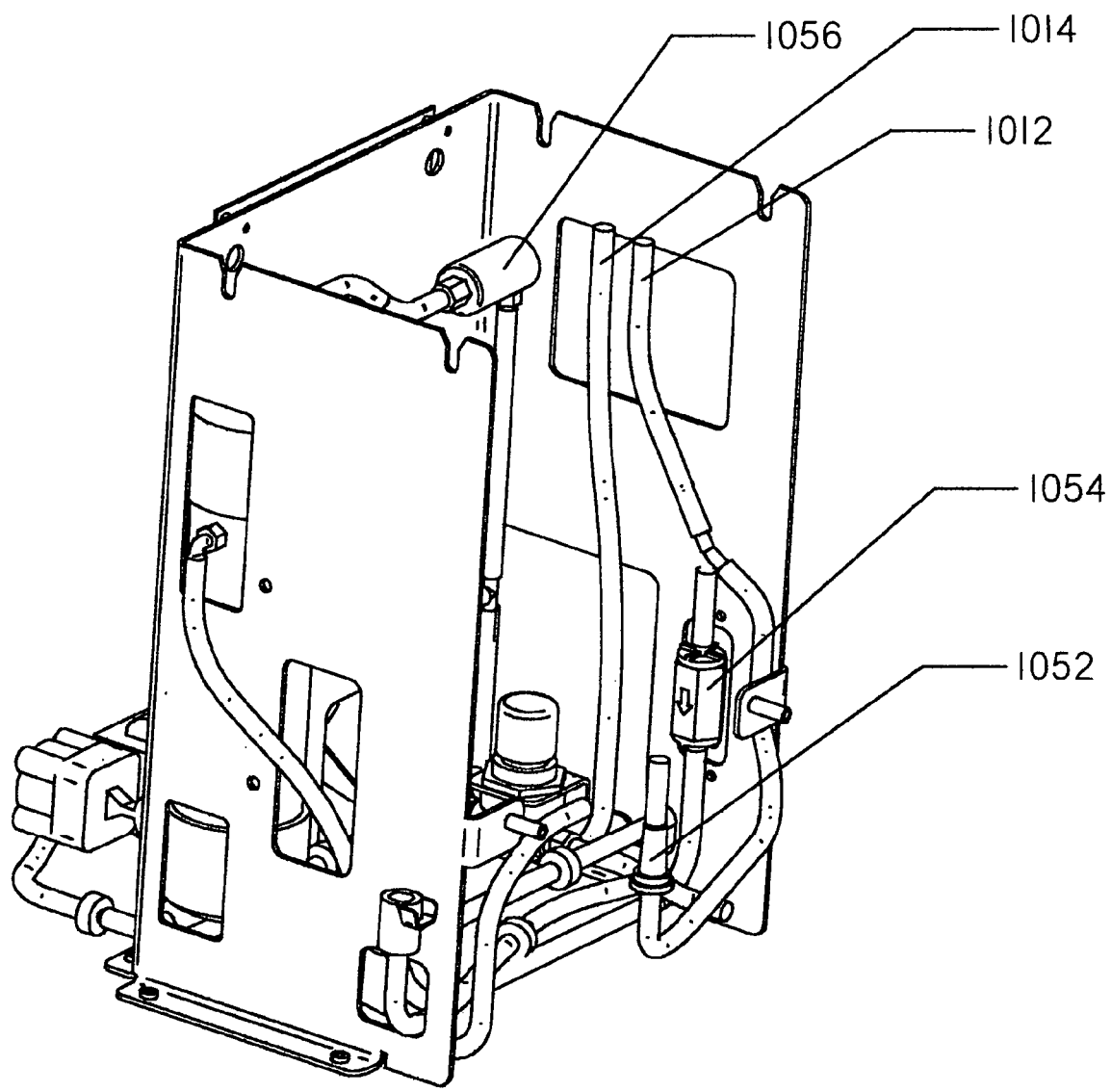
FIG. 10 depicts another perspective view of a lower chassis assembly of one embodiment of the present invention.
Figure 11:
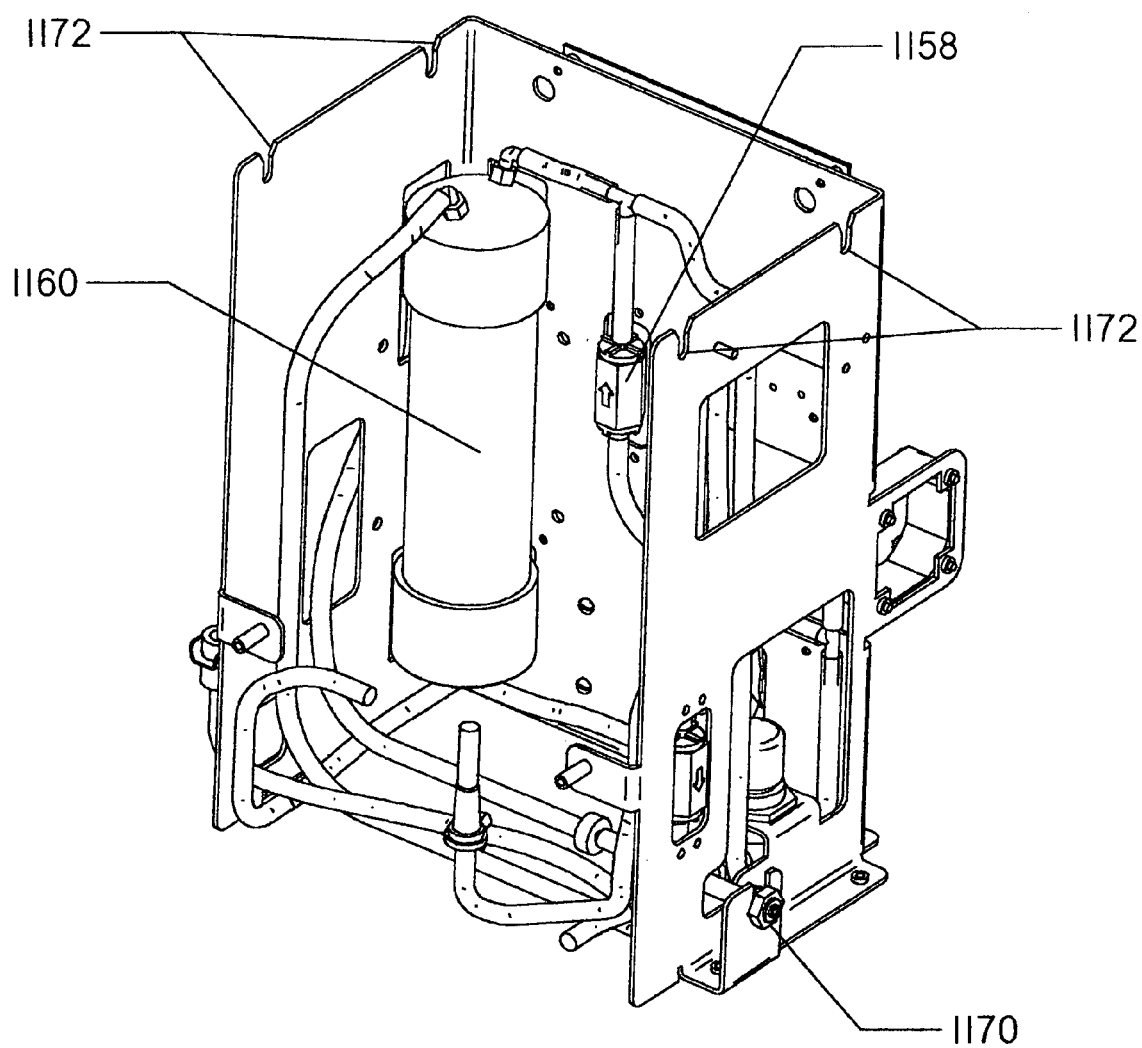
FIG. 11 depicts another perspective view of a lower chassis assembly of one embodiment of the present invention.

FIGS. 9–11 depict perspective views of a lower chassis assembly of a liquefaction device according to one embodiment of the present invention. Shown in FIGS. 9–11 are feed tube 912, 1012; vent tube 914, 1014; solenoid valve 1056; relief valve 1054 for the feed tube 1012; filter 1052; relief valve 1158 for the vent tube 1014; vent port 1170; and boiloff tube 1160. In one embodiment, feed tube 1012 and/or vent tube 1014 are one quarter inch inner diameter vinyl tubing. Also shown are mounting slots 1172 onto which an upper chassis assembly may be inserted.

Figure 12:
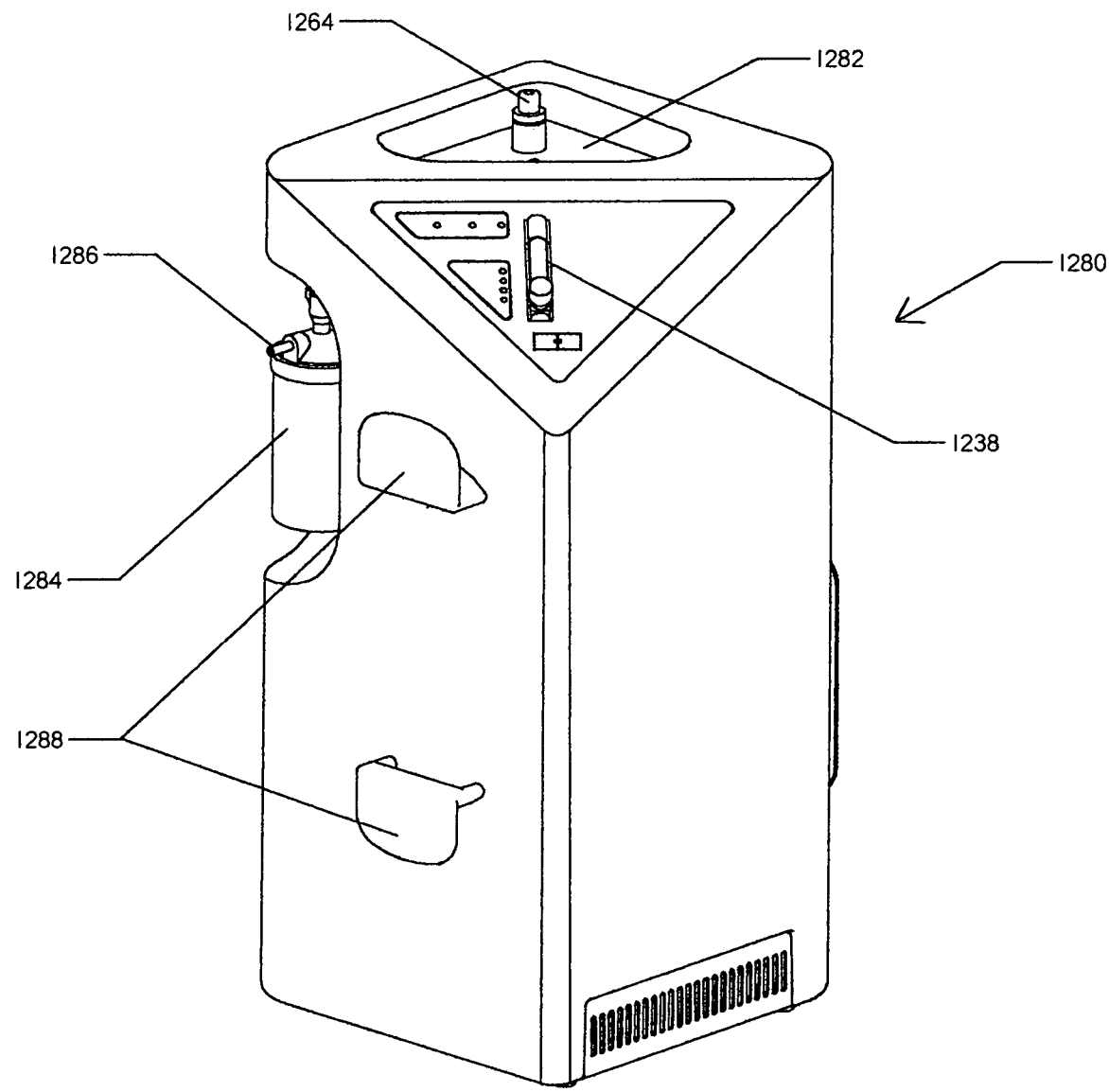
FIG. 12 depicts a perspective view of the outer housing of a liquefaction device according to one embodiment of the present invention, showing a possible placement of a detachable humidifier.

FIGS. 12 and 13 depict a perspective view of the outer housing 1280 of a liquefaction apparatus according to one embodiment of the present invention, showing a possible placement of a detachable humidifier 1284. Humidifier bottle 1284 is attached to patient flow tube 534. A humidifier may not be used at the outlet of the oxygen concentrator 530 because the liquefaction process cannot tolerate water vapor mixed with oxygen. In one embodiment, humidifier bottle features an attachment nozzle 1286 for attaching a canula. Patient flow meter 1238 allows a patient to adjust flow rate of oxygen received. The top of the outer housing 1280 features an indentation 1282 in the shape of the bottom of a portable stroller 668 to facilitate fitting the stroller 668 over transfill valve 1264. The indentation 1282 also accommodates the portable stroller 668 in order to allow the portable stroller 668 to depress a transfill switch 666. Indentation 1282 may be a depression formed on outer housing 1280, shaped to fit a valve interface surface 697 of portable stroller 668. The stroller 668 also has a valve that interfaces specifically with transfill valve 1264, such that when the stroller 668 is engaged onto the transfill valve 1264, a connection opens between the two valves allowing fluid to flow freely between them.

In one embodiment, outer housing 1280 has handles 1288. Handles 1288 may facilitate patient handling and movement of the liquefaction device. Handles 1288 may also be configured to allow a canula to be wrapped around them for storage while the canula is not in use. Alternatively, handles may be secured into the outer housing 1280 with fasteners that are also operable to hold wires in the correct place along the inside of the outer housing 1280. For example, if the handles 1288 are secured to the outer housing 1280 with screws, a wire on the inside of the outer housing 1288 may be laid under a strap secured to the inside of the outer housing 1288 between two screw heads, thus securing a placement of the wire. In one embodiment, the handles may be integral to the outer housing 1288.

Figure 14:
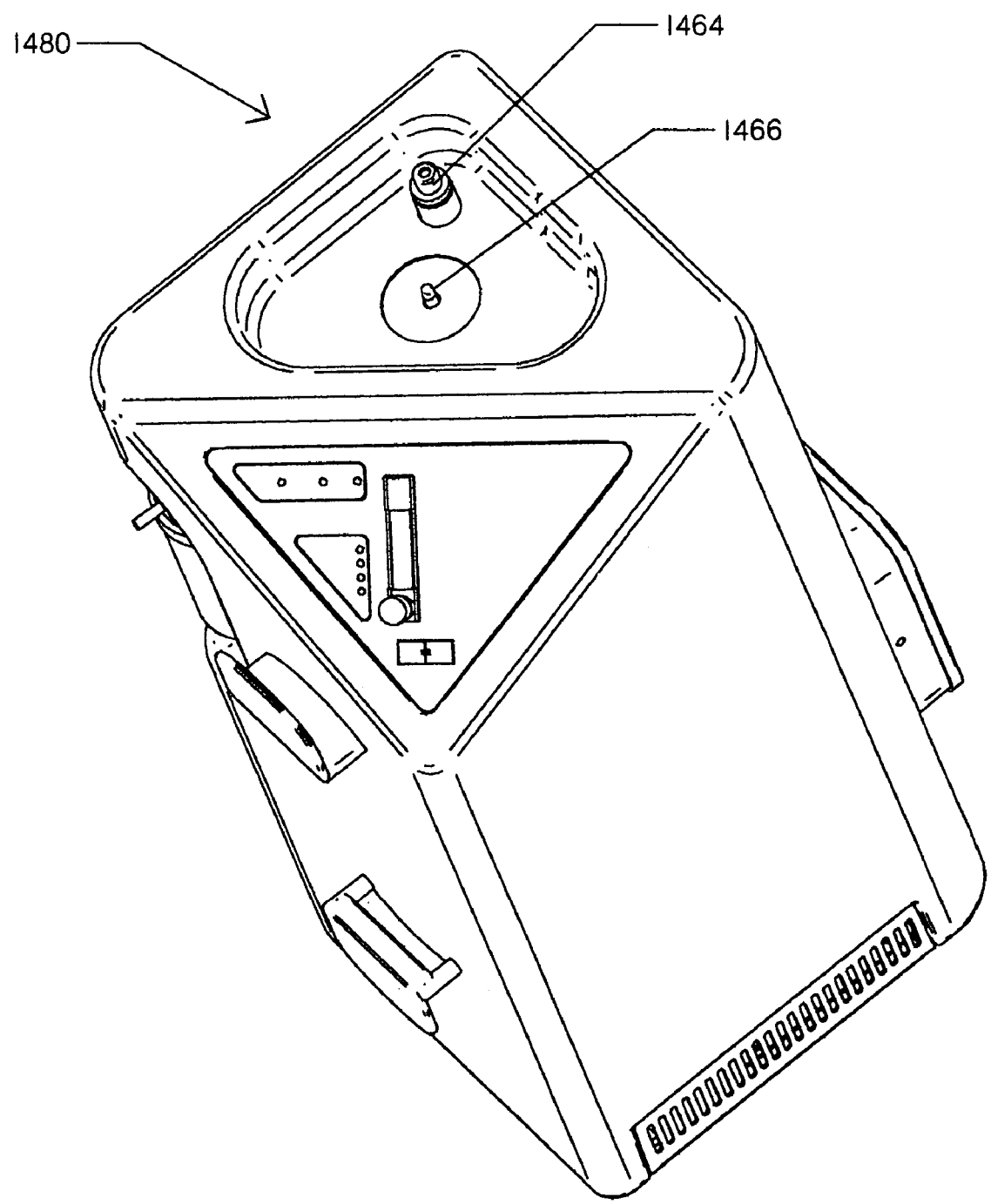
FIG. 14 depicts a top perspective view of the outer housing of a liquefaction device according to one embodiment of the present invention, showing one embodiment of a transfill valve and transfill switch.

FIG. 14 depicts a top perspective view of the outer housing 1480 of a liquefaction device according to one embodiment of the present invention, showing one embodiment of a transfill valve 1464 and transfill switch 1466.

Figure 15:
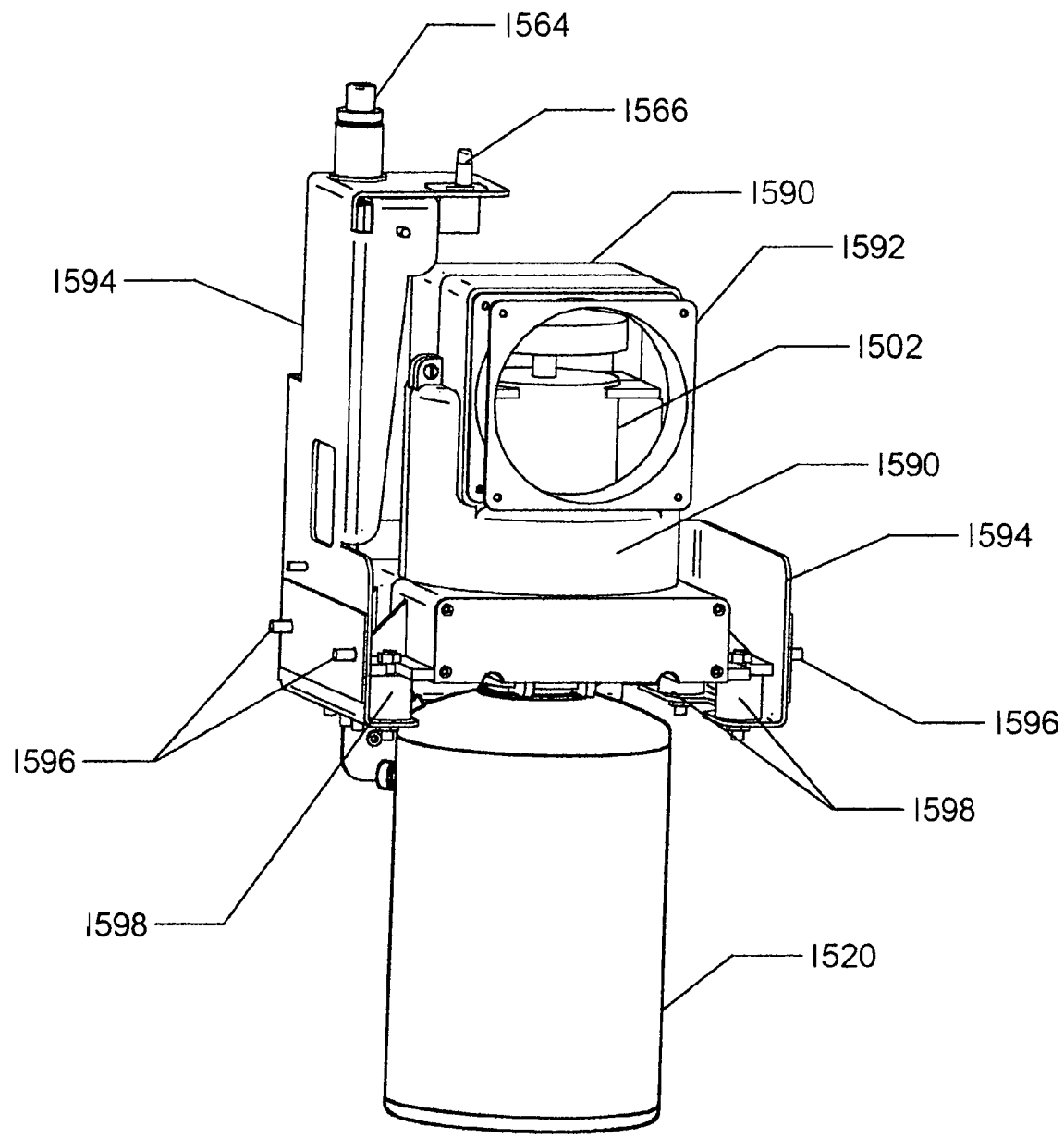
FIG. 15 depicts a side perspective view of a cryocooler and dewar secured by a mounting shroud to an upper chassis of a liquefaction device according to one embodiment of the present invention.

FIG. 15 depicts a side perspective view of a cryocooler 1502 and dewar 1520 secured by a mounting shroud 1590 to an upper chassis 1594 of a liquefaction device according to one embodiment of the present invention. The mounting shroud 1590 comprises a cooling fan mount 1592. In one embodiment, the upper chassis 1594 has mounting pegs 1596 that fit into mounting slots 1172 (see FIG. 11) on a lower chassis. In one embodiment, mounting shroud 1590 is secured to upper chassis 1594 via vibration dampeners 1598. The vibration dampeners 1598 greatly reduce noise due to vibration by isolating the cryocooler 1502 and mounting shroud 1590 from the upper chassis 1594 at the places where the mounting shroud 1590 contacts the upper chassis 1594: the four mounting bolts. Vibration dampeners 1598 may be made with rubber. For example, vibration dampeners 1598 may be made with Buna-N rubber. Alternatively, vibration dampeners 1598 may be made with any other vibration-dampening materials or devices. For example, vibration dampeners 1598 may comprise a spring dampener assembly.

Figure 16:
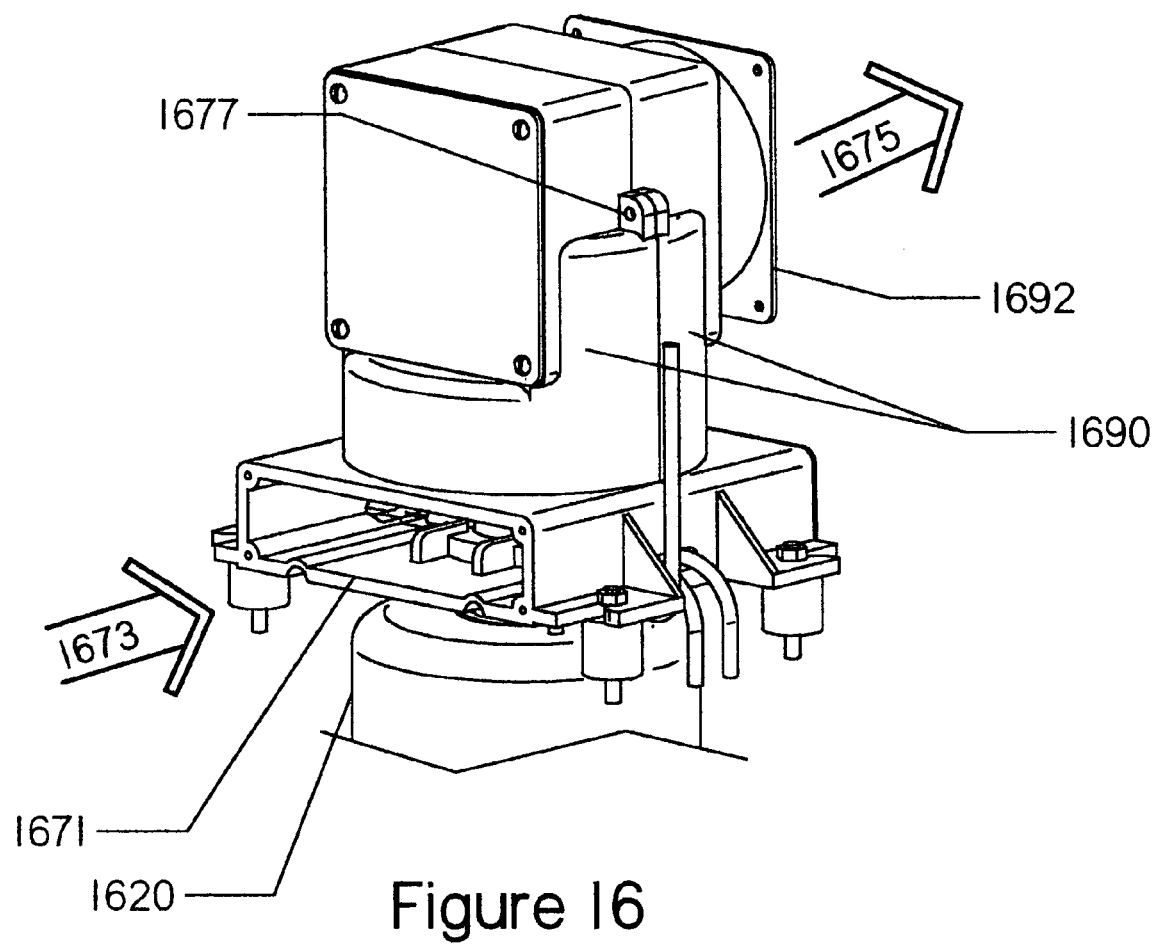
FIG. 16 depicts a perspective view of a mounting shroud and dewar according to one embodiment of the present invention.
Figure 17:
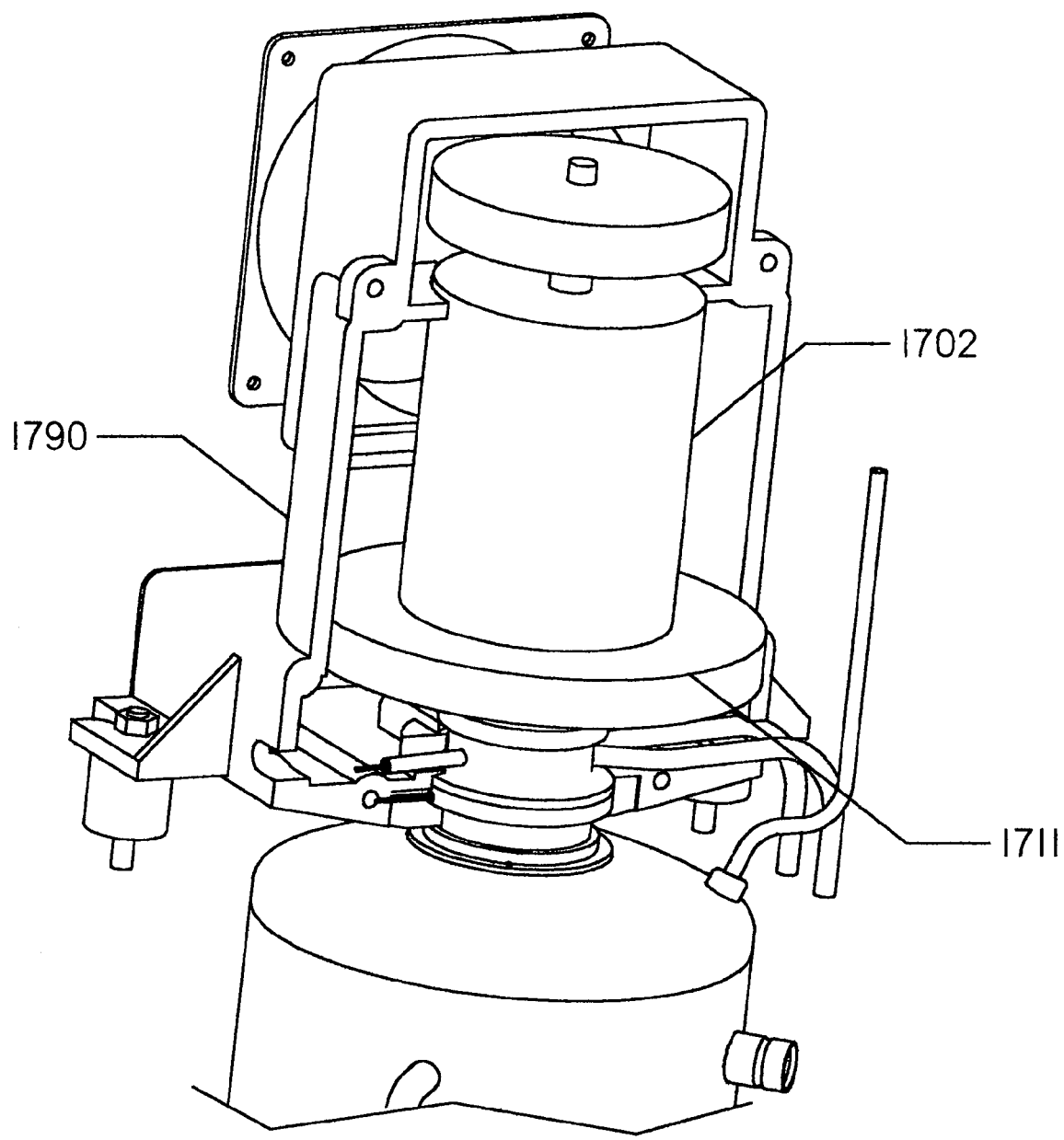
FIG. 17 depicts a side perspective view similar to FIG. 16, with the mounting shroud shown in cut-away view.

FIG. 16 depicts a perspective view of a back side of the mounting shroud 1690 and dewar 1620 according to one embodiment of the present invention. The shape of the inside of the mounting shroud 1690 may be such that it directs airflow over a cooling fin of a cryocooler. A fan may be mounted in fan housing 1692 to pull air in the direction indicated by arrow 1675. Consequently, air enters the air intake 1671 in the direction indicated by arrow 1673, blows over a cooling fin of the cryocooler, and exits the mounting shroud 1690 through fan housing 1692. FIG. 17 shows a partial cutaway view of the mounting shroud 1790, revealing cryocooler 1702 and cryocooler cooling fin 1711.

Figure 18:
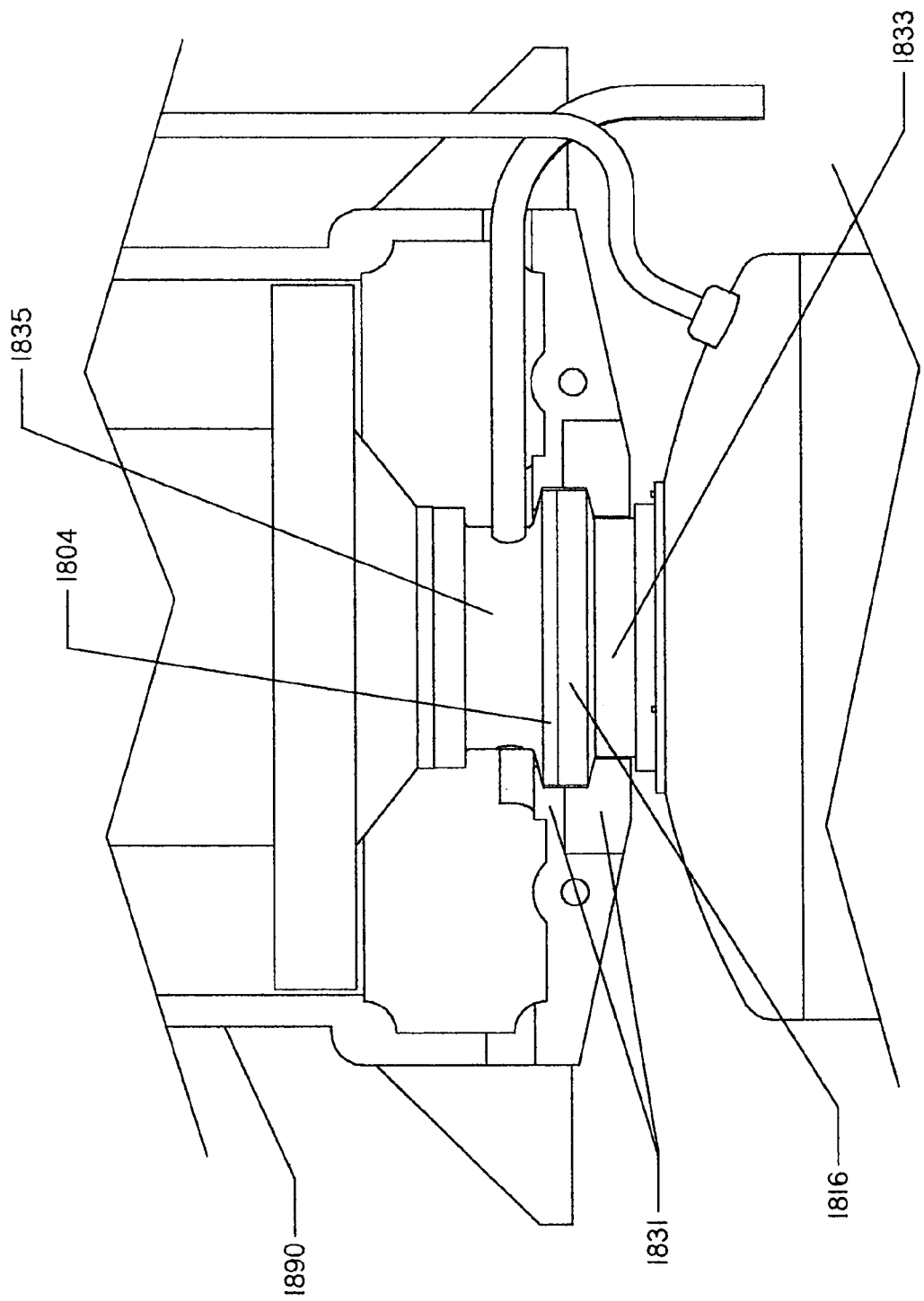
FIG. 18 depicts a side perspective view of a cryocooler/dewar flange interface with a cut-away view of a mounting shroud.
Figure 19:
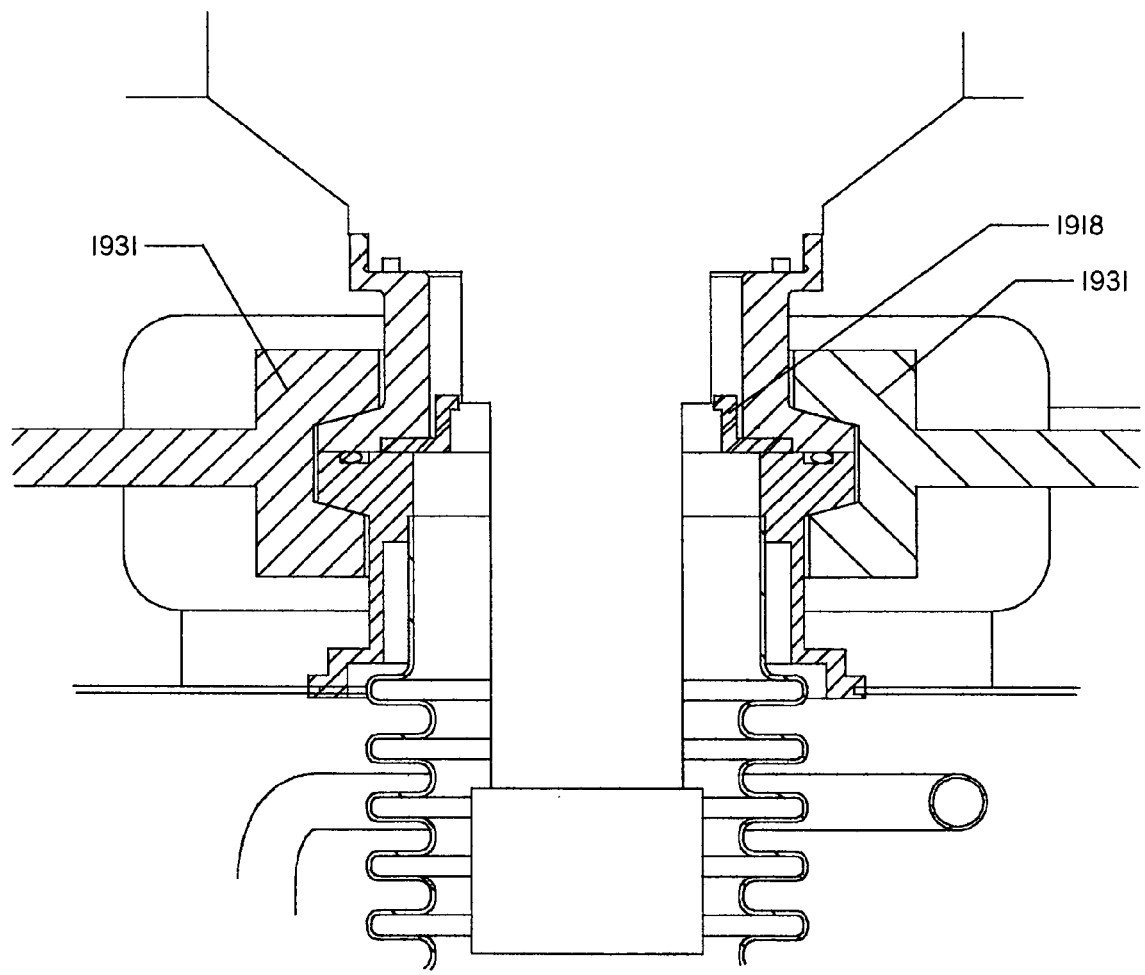
FIG. 19 depicts a side perspective, cut-away view of an inside of a cryocooler and dewar interface of one embodiment of the present invention, showing one embodiment of a cold finger and a liquid oxygen barrier.

FIG. 18 depicts an interface between a cryocooler flange 1804 and a dewar flange 1816 according to one embodiment of the present invention. The mounting shroud 1890 may comprise two separate pieces. The mounting shroud 1890 may alternatively comprise two halves. Two mounting shroud halves may be bolted together through bolt holes such as bolt hole 1677. In one embodiment, mounting shroud 1890 comprises a clamp, or clamping element, 1831, 1931. Clamping element 1831, 1931 encompasses at least a portion of both cryocooler flange 1804 and dewar flange 1816, as shown in FIG. 18. The cryocooler flange 1804 may include a sloped portion surface leading out from a neck portion 1835 of the cryocooler, as the outer diameter of cryocooler flange 1804 increases as it approaches dewar flange 1816. Dewar flange 1816 may also include a corresponding sloped portion surface leading out from a neck portion 1833 of the dewar, as the outer diameter of dewar flange 1816 increases as it approaches cryocooler flange 1804. Clamp 1831, 1931 may be configured to conform to the sloped portion surfaces of dewar flange 1816 and cryocooler flange 1804, in order to, for example, apply a normal force thereto. A normal force applied to the sloped portion surfaces of the cryocooler flange 1804 and the dewar flange 1816, as two halves of the clamping element 1831, 1931 are secured around the flanges 1804, 1816 and tightened, creates a corresponding axial force that pushes the two flanges 1804, 1816 together. The compression of the O-ring 106 that follows application of the clamping element 1831, 1931 serves to prevent the cryocooler flange 1804 and dewar flange 1816 interface from leaking either gaseous or liquid oxygen, even when tipped over.

Figure 4:
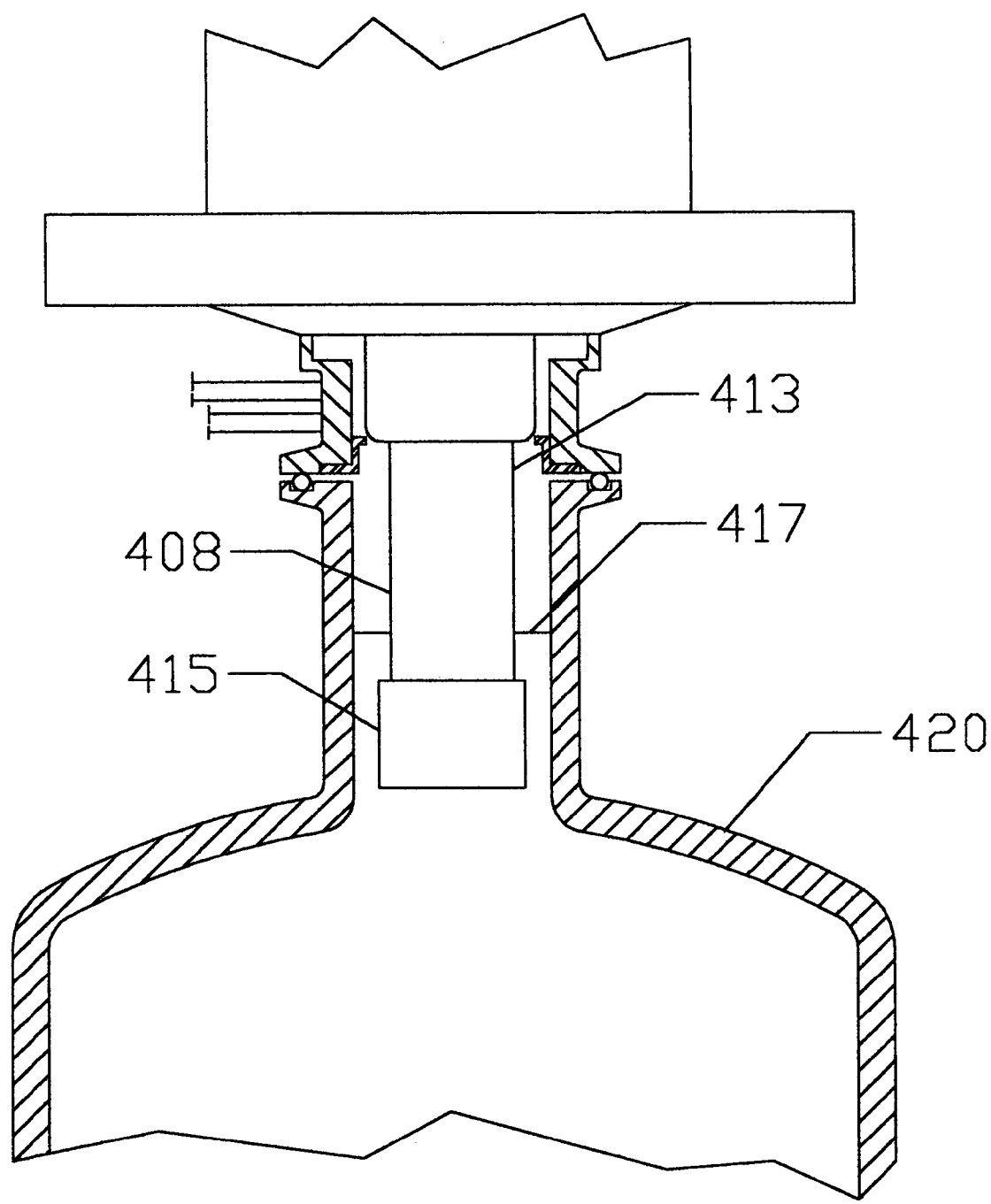
FIG. 4 depicts a cross-section, cut-away view of the cryocooler and dewar interface of one embodiment of the present invention, showing a maximum sustainable liquid oxygen level in the dewar.

With reference to FIG. 4, a mechanical, rather than electrical, means for stalling liquid oxygen production is shown according to one embodiment of the present invention. A cold finger 408 extends into dewar 420. Cold finger 408 has a temperature gradient. One end 413 of cold finger 408 has a temperature higher than the boiling point of oxygen, and another end 415 has a temperature lower than the boiling point of oxygen. As oxygen liquefies and fills the dewar 420, the liquid level 417 rises only to a level on the cold finger 408 at which the temperature exceeds the boiling point of oxygen. At this level 417, no exposed part of the cold finger 408 is cold enough to liquefy oxygen, so the liquid level 417 does not rise further; this prevents overfilling of the dewar 420.

Figure 7:
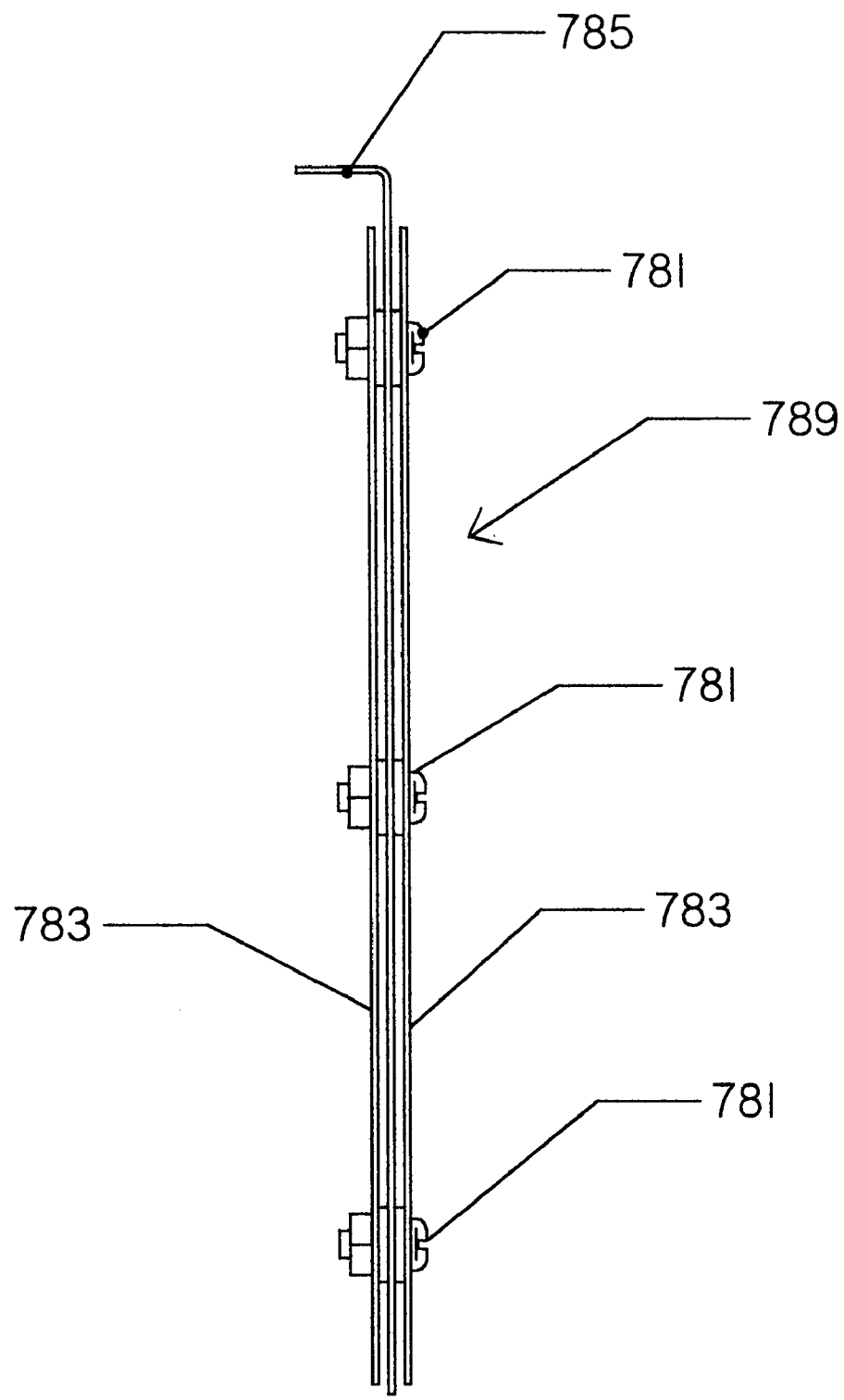
FIG. 7 depicts a side view of a liquid level sensor of one embodiment of the present invention.
Figure 8:
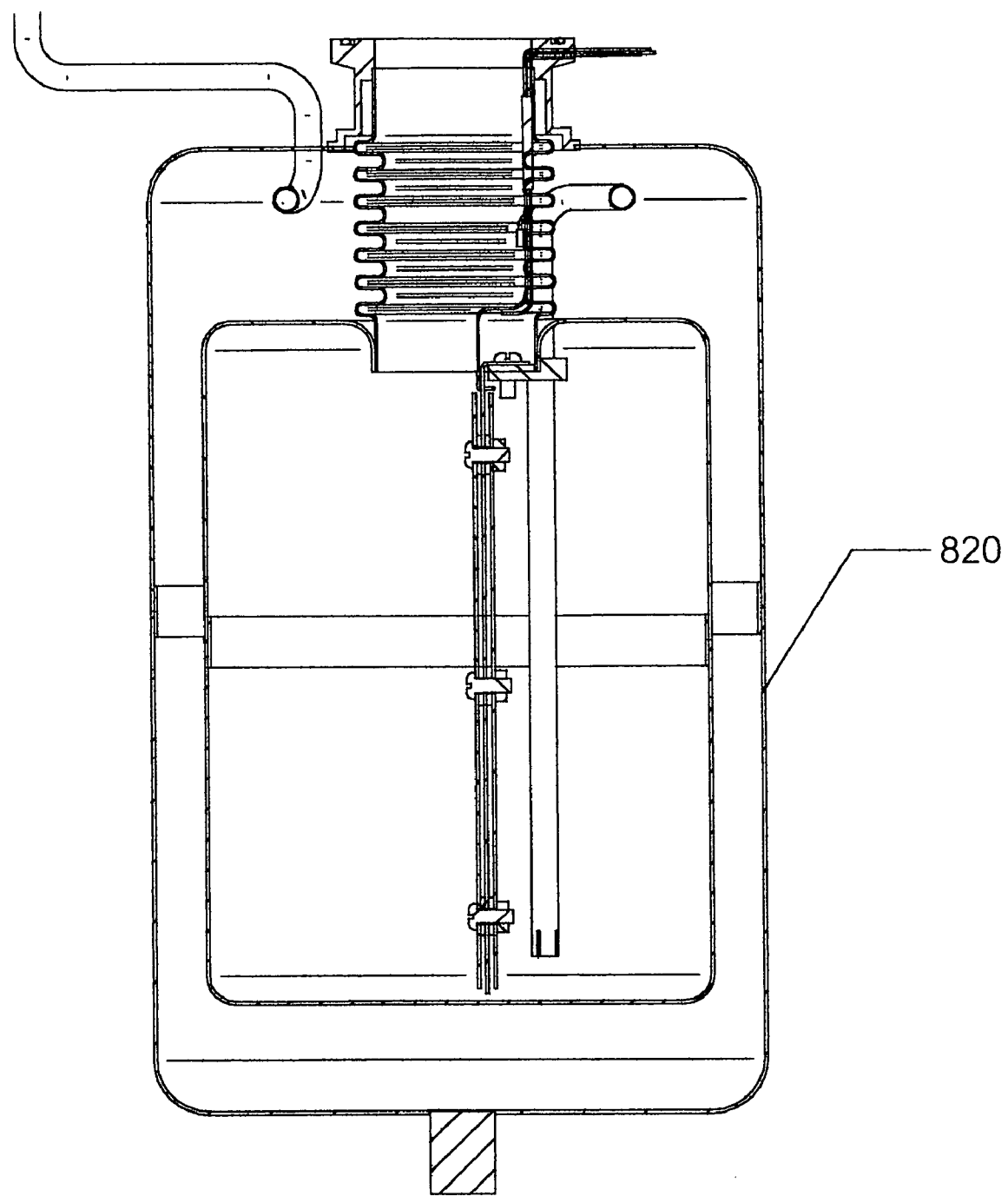
FIG. 8 depicts a cross-section, cut-away view of a dewar of one embodiment of the present invention, showing the placement therein of the liquid level sensor of FIG. 7.

Alternatively, a cryogenic liquid level sensor 789 may be used to trigger a system shutdown when the liquid level in the dewar exceeds a predetermined limit. FIG. 7 depicts a side view of a cryogenic liquid level sensor 789 of one embodiment of the present invention. Parallel plates 783 may be held together with non-conductive screws 781 on either side of a mounting plate 785; cryogenic liquid level sensor 789 may be coupled to top of dewar 820 and extend the length of the dewar 820, as according to one embodiment of the present invention depicted in FIG. 8. A capacitive method of measuring the level of liquid gas, such as liquid oxygen, in a dewar may be utilized. This method may use parallel plates 783 or parallel cylinders (not shown). As the liquid level in the dewar 820 rises, the gaseous oxygen between parallel plates 783 is gradually replaced with liquid oxygen. The dielectric-constant change between gaseous oxygen and liquid oxygen varies the capacitance measured between parallel plates 783. This capacitance change corresponds to the liquid level change in the dewar 820, and may be measured and converted to a usable form for display to a user. In one embodiment, the liquid level in the dewar is displayed in a bar-lamp format with a resolution of ¼ dewar (¼, ½, ¾, full). In one embodiment, liquid level in the dewar 820 is displayed in a digital readout.

A capacitor cryogenic liquid level sensor 789 may be constructed of two or more metal electrically conductive plates separated by a non-conductive material having a fixed dielectric constant, such as a dielectric constant greater than 1.0. Such a cryogenic liquid level sensor 789 may be used to measure the liquid level of liquid oxygen or nearly any other cryogenic liquid. Cryogenic oxygen liquid level sensor 789 may measure the difference of the change in the dielectric constant of oxygen between the gaseous phase and the liquid phase. This creates a variable capacitance directly related to liquid height. A number of different displays of liquid level may be possible with the use of cryogenic liquid level sensor 789.

Other types of cryogenic liquid level sensors may be used, according to alternative embodiments of the present invention. For example, a float may be used to measure cryogenic liquid level in a manner similar to the manner in which a float may be used as a common automotive fuel level sensor. In such cases, a float arm moves through a variable resistance as the float moves up or down on the surface of the desired liquid. This variable resistance produces a variable voltage from a known voltage source, and the variable voltage may be connected to a voltage meter or the like for display. According to other alternative embodiments of cryogenic liquid level sensors, a resistance method may be used. Such methods may, for example, utilize the thermal conductivity constant for copper (3.98 watts per centimeter—Kelvin), and the resistivity constant of copper, to sense the point between the gaseous phase and the liquid phase of the cryogenic liquid. Such a level point between the gaseous phase and the liquid phase has a differential temperature change, such as a differential temperature change of a few degrees, and thus a difference in the thermal conductivity because the gaseous phase conducts more power than the liquid phase. The liquid height may be calculated based on the level of the liquid phase as sensed by the amount of power conducted to the gaseous phase; a lower power conducted to the gaseous phase may correspond to a higher liquid level. According to yet other alternative embodiments of cryogenic liquid level sensors, semi-conductor methods may be used. Such methods may employ a special diode construction whose conduction properties change when exposed to cryogenic temperatures; in some instances, the special diode construction may be an individual point(s) monitoring device controlled via a microcontroller/processor. According to further alternative embodiments of cryogenic liquid level sensors, ultra-sonic methods may be used. Such methods may use a pulsed high or ultra-high frequency ultrasonic transducer to measure the "Doppler Effect" of the reflected signal from the surface of the measured liquid. A shorter "Doppler Effect" measurement corresponds to a higher cryogenic liquid level.

Figure 22:
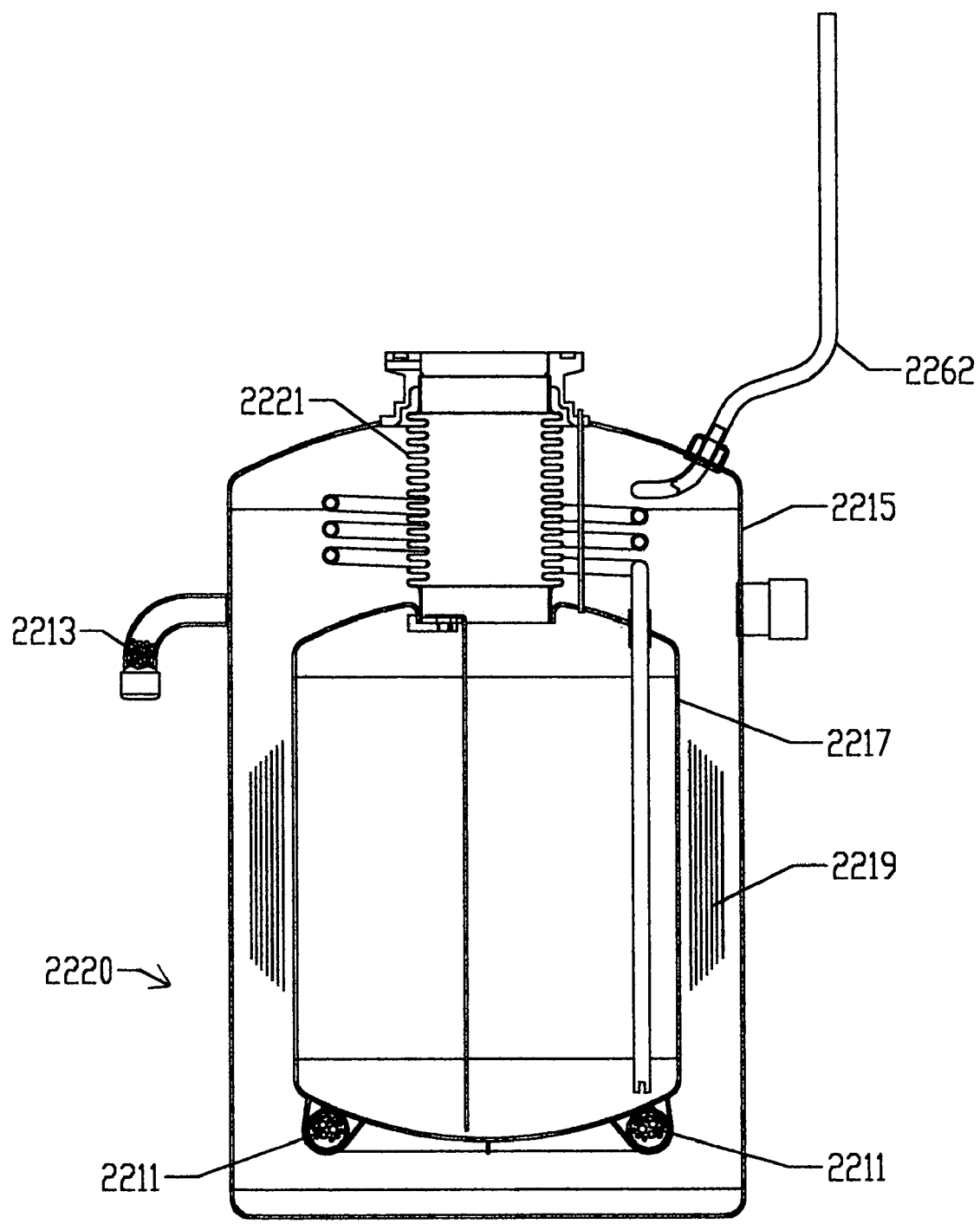
FIG. 22 depicts a side view of a dewar according to one embodiment of the present invention.

FIG. 22 depicts an efficient dewar 2220 design. Liquid oxygen may be stored in an inner vessel 2217. The inner vessel 2217 is contained by the outer vessel 2215. Between the inner vessel 2217 and outer vessel 2215 is a near-vacuum space to minimize convective heat transfer. A wrapping material 2219, such as SuperWrap, is wrapped around the inner vessel 2217 to slow radiant heat transfer. Cold getters 2211 capture errant moisture molecules from within the vacuum space. A warm surface getter 2213 captures hydrogen molecules from within the vacuum space. A transfill tube 2262 reaches through the inner vessel 2217, then wraps several times around the bellows neck 2221, then exits through the outer vessel 2215. By increasing the length of the transfill tube 2262 within the vacuum space, and by narrowing the cross-sectional area of the tube 2262, conductive heat losses are minimized. Conductive heat losses are also minimized by the bellows neck 2221. The inner vessel 2217 is coupled to the outer vessel 2215 by bellows neck 2221. Bellows neck 2221 may have an accordion shape, as depicted in FIG. 22, in order to increase the length of the path that heat must travel to escape. Other bellows neck 2221 designs may be employed to increase the length of the path that heat must travel to escape.

Figure 2:
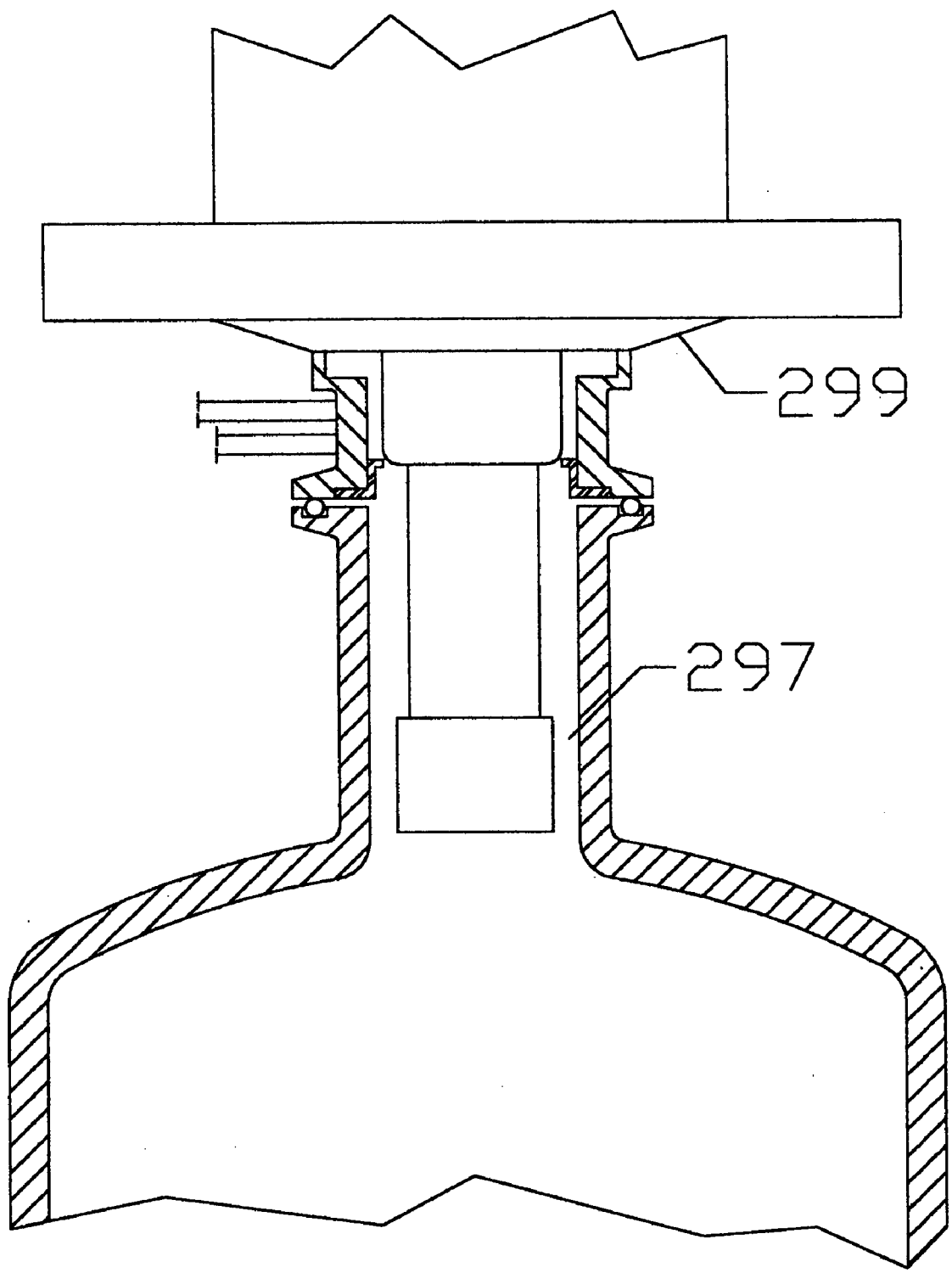
FIG. 2 depicts a cross-section, cut-away view of the cryocooler and dewar of one embodiment of the present invention, showing a possible placement of temperature sensors.

Referring now to FIG. 2, a fin temperature sensor 299 may be located in proximity to a cooling fin of a cryocooler. Additionally, a cold finger temperature sensor 297 may be located in proximity to a cold finger of a cryocooler. The fin temperature sensor 299 may detect potentially hazardous or damaging conditions; for instance, sensing a fin temperature that is too high may indicate that the cooling fan has failed and the cryocooler is overheating. The fin temperature sensor 299 may also detect whether the liquefaction apparatus has been placed in sunlight, an excessively warm room, or whether its cooling vents have been obstructed. Cold finger temperature sensor 297 may detect if a displacer in the cryocooler has seized, causing the cold finger to warm up rather than cool down. In embodiments that use alternative liquid oxygen barrier 2061 (see FIGS. 20–21), cold finger temperature sensor 297 may alternatively be located inside of flow director portion 2065. When either fin temperature sensor 299 or cold finger temperature sensor 297 senses a temperature that is too high, a circuit latches a "halt" signal to the cryocooler control and stops the motor. An indicator lamp for the user may be illuminated during this fault. The "halt" signal may be released by recycling power to the liquefaction apparatus, unless the excessive temperature condition is still present.

Figure 27:
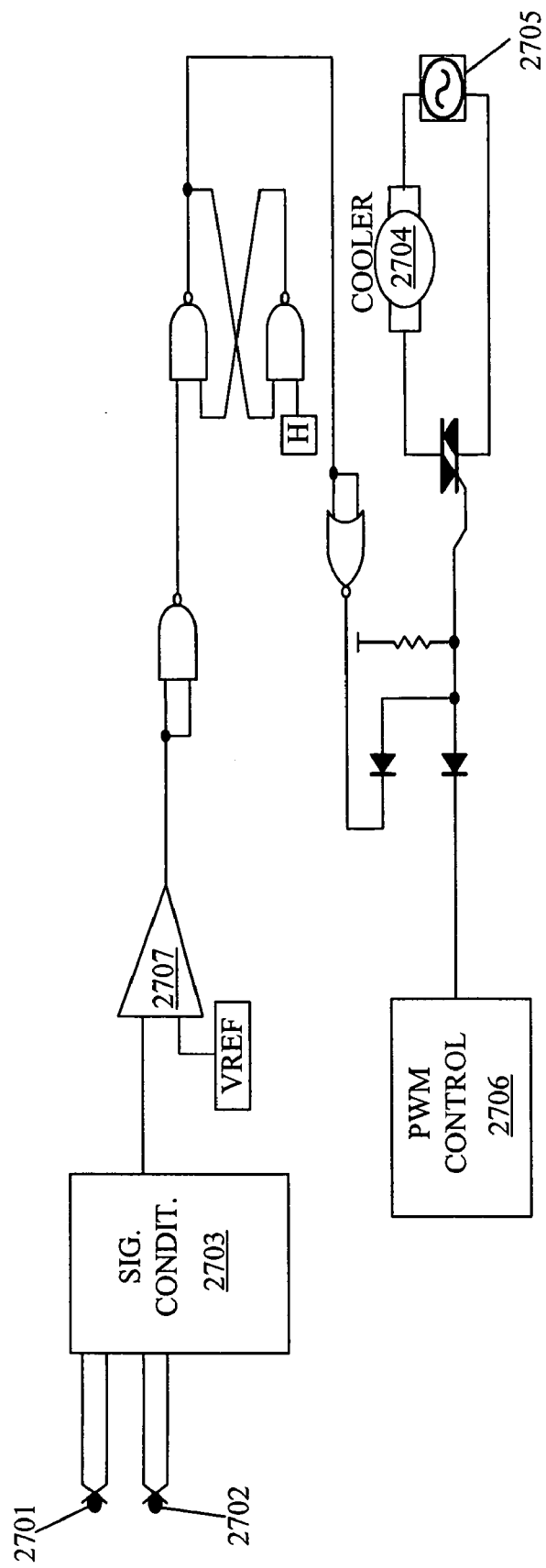
FIG. 27 depicts a conceptual wiring diagram for a temperature sensing circuit to turn off electrical components of a liquefaction system, according to various embodiments of the present invention.

FIG. 27 depicts a conceptual wiring diagram for a temperature sensing circuit to turn off electrical components of a liquefaction system, according to various embodiments of the present invention. A signal conditioner may be coupled with temperature sensors or thermocouples 2701, 2702. The signal conditioner outputs a temperature signal corresponding to one, both, or more of temperature sensors 2701, 2702. As one example, temperature sensor 2701 may be located and/or configured to measure the temperature near a cooling fin of a cryocooler 2704, also known as the reject temperature. As yet another example, temperature sensor 2702 may be located and/or configured to measure the temperature near a cold finger of a cryocooler 2704. The signal is compared to a reference voltage by a comparator 2707. When either temperature sensor 2701, 2702 senses a temperature that is too high, the depicted circuit latches a "halt" signal to the cryocooler PWM control 2706 and stops the motor of cryocooler 2704 by breaking the electrical power circuit supplying power from source 2705 to cryocooler 2704. Power may be removed from cryocooler 2704 when either temperature sensor 2701 or temperature sensor 2702 senses a temperature that is too high; for example, according to some embodiments of the present invention, temperature sensor 2701 may sense a cryocooler cooling fin temperature above sixty-five degrees Celsius, or temperature sensor 2702 may sense a cold finger temperature above fifty degrees Celsius. An indicator lamp for the user may be illuminated during this fault. The "halt" signal may be released by recycling power to the liquefaction apparatus, unless the excessive temperature condition is still present.

Figure 25:
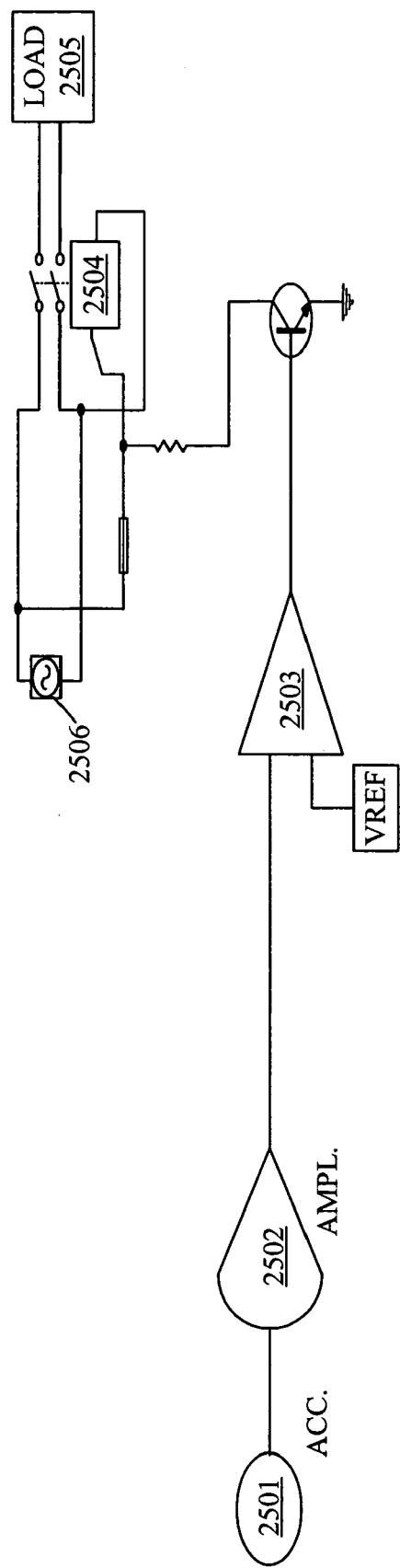
FIG. 25 depicts a conceptual wiring diagram for an impact-sensing mechanism to turn off electrical components of a liquefaction system, according to various embodiments of the present invention.

FIG. 25 depicts a conceptual wiring diagram for an impact-sensing mechanism to turn off electrical components of a liquefaction system, according to various embodiments of the present invention. Power supplied by source 2506 to a load 2505 is passed through an actuated contact assembly (i.e. circuit breaker or relay or semi-conductor circuit). As long as power is applied to the actuator mechanism 2504, power is allowed through the contact assembly. During a tip-over condition, the sensing output of an accelerometer 2501 or other impact sensing device 2501 is amplified into a desired range by amplifier 2502. This voltage range is input into an analog-to-bit converter and compared to a known voltage at comparator 2503. The "bit" output triggers a switching device. When the switching device is active, a circuit protector device removes the power to the actuator mechanism 2504 and removes power to the load 2505. Load 2505 may be, but is not limited to, the cryocooler, cryocooler driver, cooling fan, circuit boards, and/or any other element that operates via electrical power.

Figure 26:
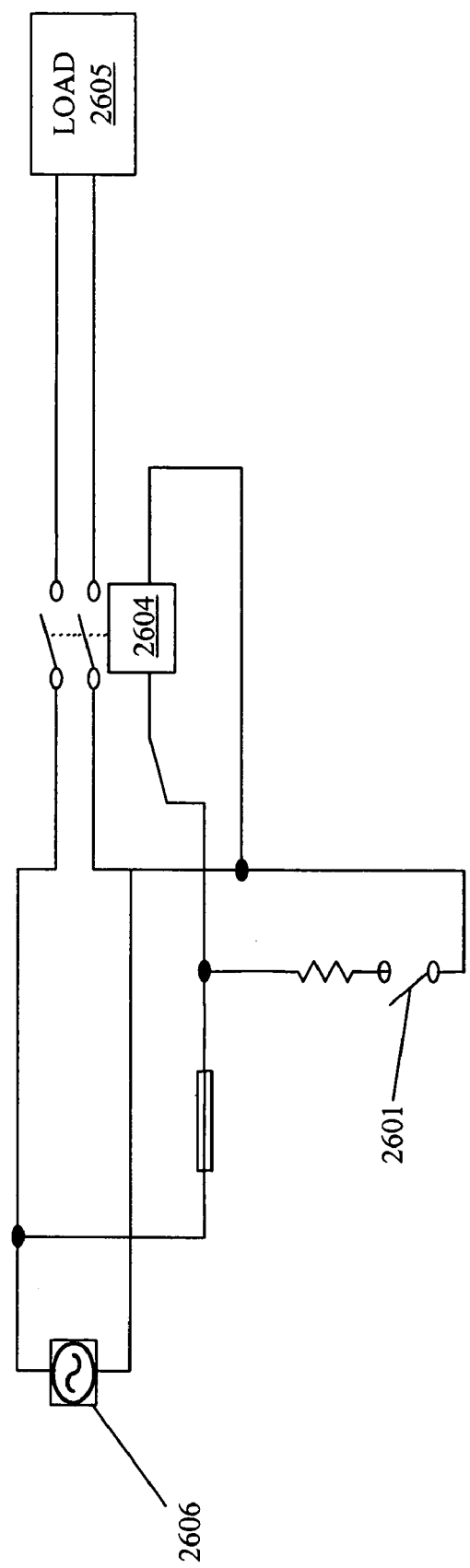
FIG. 26 depicts a conceptual wiring diagram for a tip-over switch to turn off electrical components of a liquefaction system, according to various embodiments of the present invention.

FIG. 26 depicts a conceptual wiring diagram for a tip-over or tilt switch to turn off electrical components of a liquefaction system, according to various embodiments of the present invention. Tip/tilt switch 2601 may be any switch capable of changing states, from "on" to "off" or from "off" to "on," when tip/tilt switch 2601 experiences a rotation in angle or inclination. Tip/tilt switch 2601 may be affixed to a dewar, cryocooler, and/or any other element of a gas liquefaction system to determine when the element to which it is attached has been tipped and/or tilted. For example, tip/tilt switch 2601 may be a mercury switch. Tip/tilt switch 2601 may be configured to change states upon tipping or tilting through a predetermined angle; for example, the predetermined angle may be forty-five degrees. Alternatively, the predetermined angle may be any angle indicative of a tipover or excessive tilting event; for example, the predetermined angle may be an angle in the range from thirty degrees to sixty degrees. Power from a source 2606 to a load 2605 is passed through an actuated contact assembly (i.e. circuit breaker or relay or semi-conductor circuit). As long as power is applied to the actuator mechanism 2604, power is allowed through the contact assembly. During a tip-over condition, tip/tilt switch 2601 triggers to remove power to the actuator mechanism 2604, thereby removing power to the load 2605. Load 2505 may be, but is not limited to, the cryocooler, cryocooler driver, cooling fan, circuit boards, and/or any other element that operates via electrical power.

Figure 28:
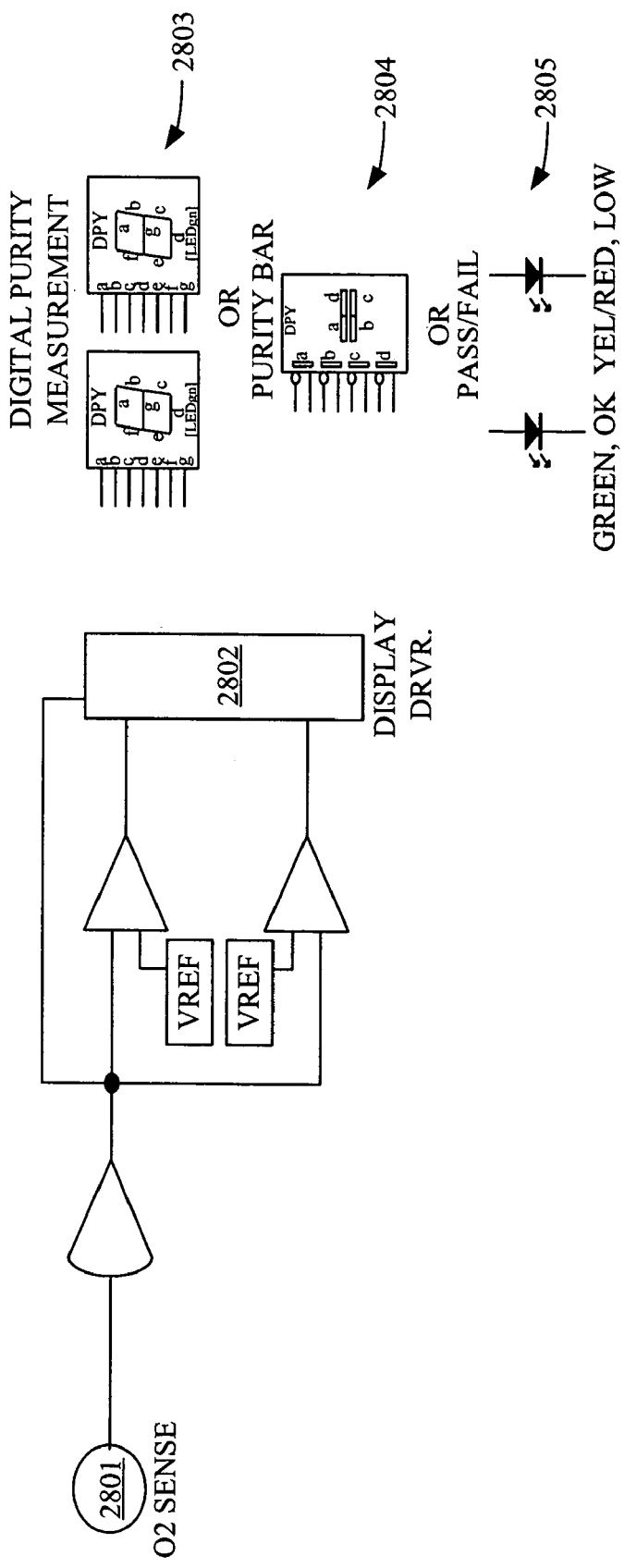
FIG. 28 depicts a conceptual wiring diagram for measurement of oxygen purity and display options for displaying oxygen purity, according to various embodiments of the present invention.

FIG. 28 depicts a conceptual wiring diagram for measurement of oxygen purity and display options for displaying oxygen purity, according to various embodiments of the present invention. Several methods of oxygen purity sensing exist; for example, oxygen purity may be measured with a Galvanic-type micro-"fuel-cell" method, or with a light refraction method. Each oxygen purity sensing element may provide a different usable output, and each may require its own conversion circuitry. Similarly, each possible method for displaying oxygen purity information may requires its own conversion circuitry and/or method. As illustrated in FIG. 6, oxygen purity sensor 568 may be located in feed flow line 512. For example, oxygen purity sensor 568 may be located in fluid communication with feed flow line 512 and/or inline with feed flow line 512 anywhere prior to liquefaction. If oxygen purity sensor 568 is sensitive to input pressure, oxygen purity sensor may be placed in feed flow line 512 downstream from pressure regulator 540 and/or orifice 542.

According to one embodiment of the present invention, a sensor 2801, such as a "fuel-cell" sensor, may be used to measure oxygen purity. A sensed oxygen purity may be displayed through various graphical representations, such as, for example, numerical LED indicators 2803, purity bar LED indicators 2804, and/or colored LEDs 2805. The usable sensing output of the "fuel-cell" may be, but is not limited to, a signal corresponding to millivolts per percent of oxygen. This signal may be amplified into a required voltage range. When using a simple pass/fail type of information display, the amplified signal may be input to a series of analog-to-bit converters. A display driver 2802 may then switch ON independent LED's or lamps to indicate a pass/fail condition of the gaseous oxygen purity level. For example, display driver 2802 may display a numerical purity measurement via numerical LED indicators 2803. According to some embodiments, display driver 2802 may display a graphical purity measurement via a purity bar LED indicator 2804. According to yet other embodiments, display driver 2802 may display a pass/fail purity measurement via green, yellow, and/or red LEDs 2805; in such cases, activation of a green LED may signal a satisfactory oxygen purity level, activation of a yellow LED may signal a potential though not necessarily serious problem with oxygen purity, and activation of a red LED may signal a serious or dangerously low oxygen purity level. According to some embodiments of the present invention, the satisfactory oxygen purity range a purity greater than 85% oxygen by volume.

Figure 31:
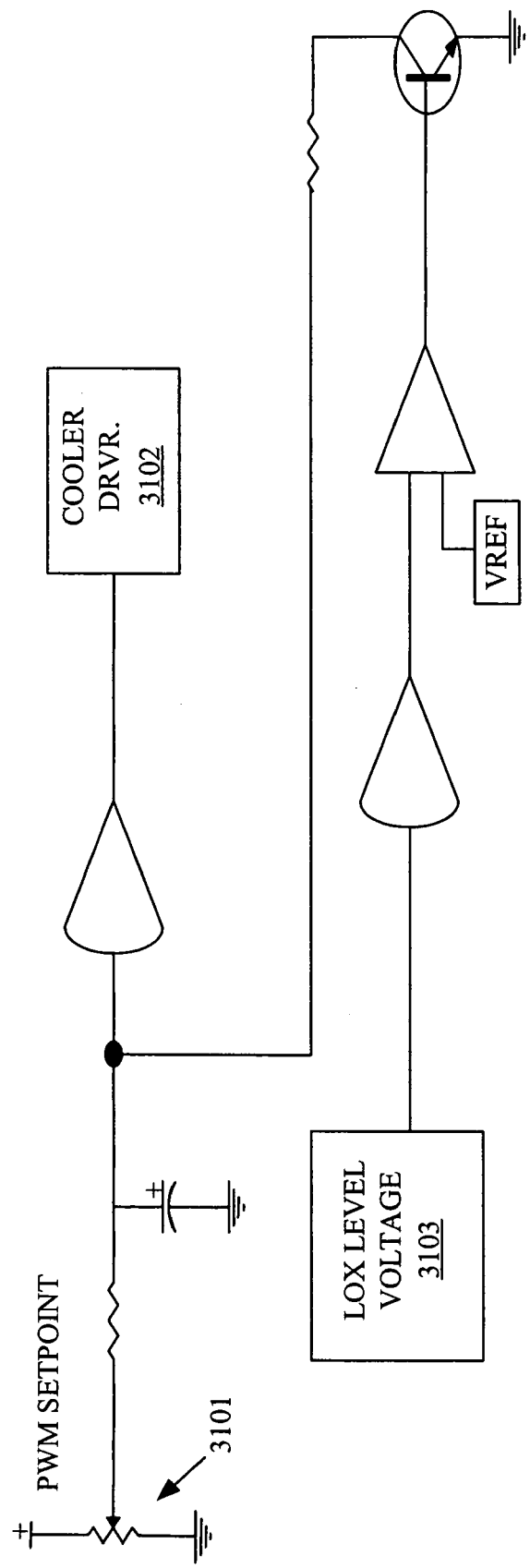
FIG. 31 depicts a conceptual wiring diagram illustrating a cryocooler low power mode, according to various embodiments of the present invention.

FIG. 31 depicts a conceptual wiring diagram illustrating a cryocooler low power mode, according to various embodiments of the present invention. When the dewar is full in a liquefaction apparatus of embodiments of the present invention, the cryocooler continues to run, but does not continue to liquefy oxygen. This is due to the liquid level rising to a point on the cold finger such that no exposed portion of the cryocooler's cold finger is colder than the liquefaction temperature of oxygen. Continuing to run the cryocooler at full power with a full dewar may result in an over-expenditure of energy. Although electrical power may be removed completely from the cryocooler when a full dewar is sensed, lowering power instead of removing power may reduce wear on cryocooler components and eliminate any potential noise associated with a cryocooler cold start. Potential advantages of implementing a low power mode of the cryocooler and/or cooling fan include, but are not limited to, a reduced noise level, a reduction in excess heat generation, reducing liquid boiloff rate for liquid gas within the dewar, and/or decreasing cryocooler wear. Implementing a low power mode of the cryocooler and/or cooling fan may reduce power consumption by over fifty percent while the dewar is full, and may reduce power consumption by thirty to thirty-five percent overall. According to some embodiments of the present invention, a low power or energy saving mode may be initiated when the cryogenic liquid level sensor sensed a full liquid level in the dewar, and may return to a normal mode when the cryogenic liquid level sensor sensed a predetermined liquid level in the dewar; for example, the low power mode may return to the normal mode when the cryogenic liquid level sensor senses a three-fourths full liquid level in the dewar.

According to some embodiments of the present invention, a low power mode may be entered by simply reducing the power supplied to the cryocooler and/or cooling fan to a predetermined power level. FIG. 31 shows one embodiment of a circuit operable to reduce power to the cryocooler driver 3102. In normal operation, the full PWM setpoint 3101 voltage may be applied to the cryocooler driver 3102. The cryogenic liquid level sensor supplies a liquid level voltage 3103 that may be amplified and compared with a reference voltage to determine when the liquid level is full and thus when the low power mode should be entered. When the low power operation is initiated, a switching device provides a ground path through an additional resistance, creating a voltage divider reducing the voltage applied to the cooler driver 3102 circuitry. The applied power may be set to a wide range of possible powers, depending on the energy consumption requirements of the cryocooler, and the fluid flow and/or thermodynamic characteristics of the given liquefaction system. According to some embodiments of the present invention, the applied power may be selected to keep the piston within the cryocooler centered but not displacing through its full range.

Figure 32:
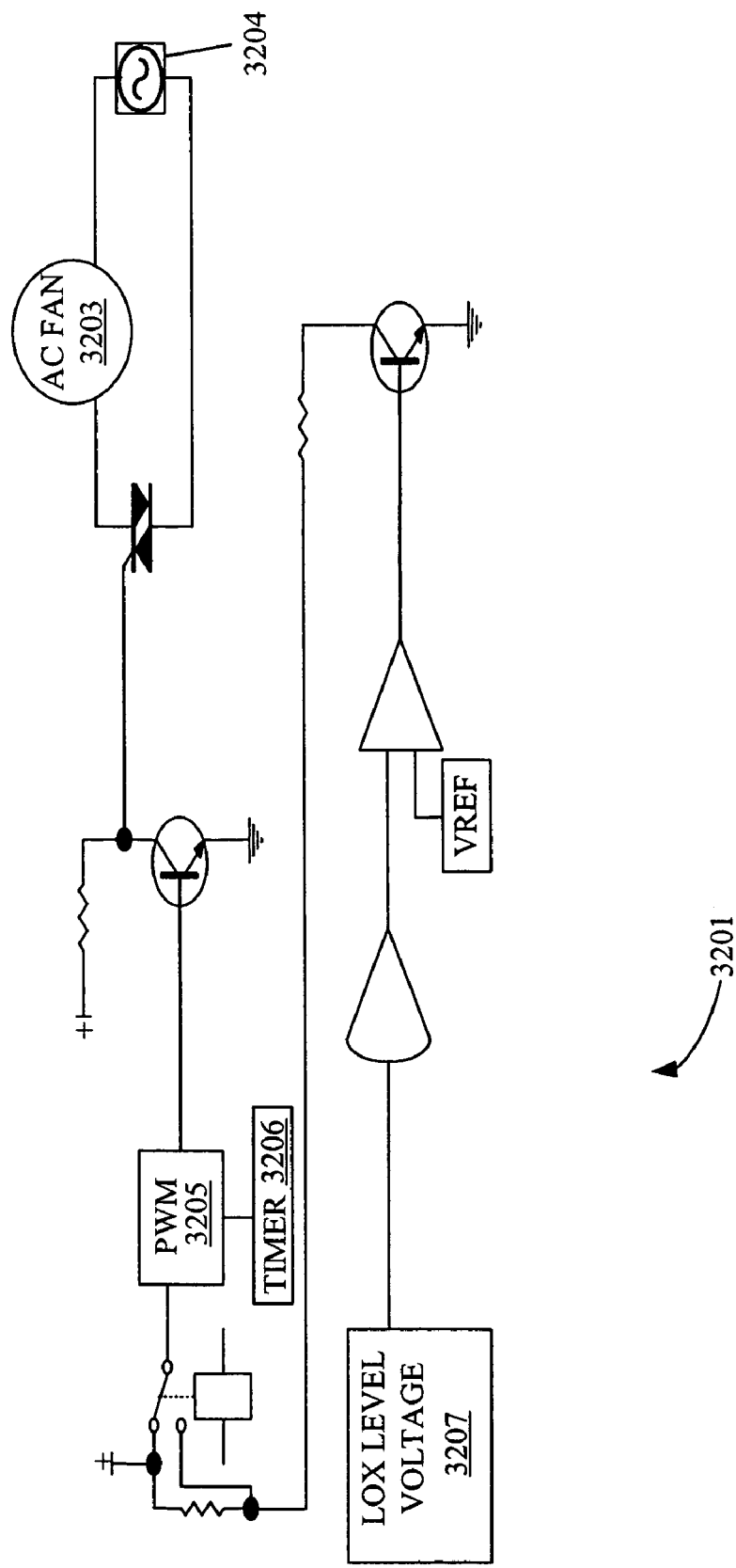
FIG. 32 depicts a conceptual wiring diagram illustrating a cooling fan low power mode, according to various embodiments of the present invention.

FIG. 32 depicts a conceptual wiring diagram illustrating an alternating current cooling fan low power mode, according to various embodiments of the present invention. A first circuit diagram 3201 illustrates a low power mode for an alternating current fan 3203 supplied with power by source 3204. During normal operation, a full setpoint voltage is applied to a PWM/Random phase controller 3205 having a timer 3206, and applies full voltage to the cooling fan 3203. When a lower fan speed is desired to reduce noise and when full LOX production is not required, a switching device may be activated creating a ground path through a second resistance. Such a switching device may be activated when a cryogenic liquid level sensor supplies a liquid level voltage 3207 signal that exceeds a reference voltage. This creates a voltage divider circuit and reduces the voltage setpoint for the PWM/random phase fan driver 3205 and slows the fan speed.

Figure 33:
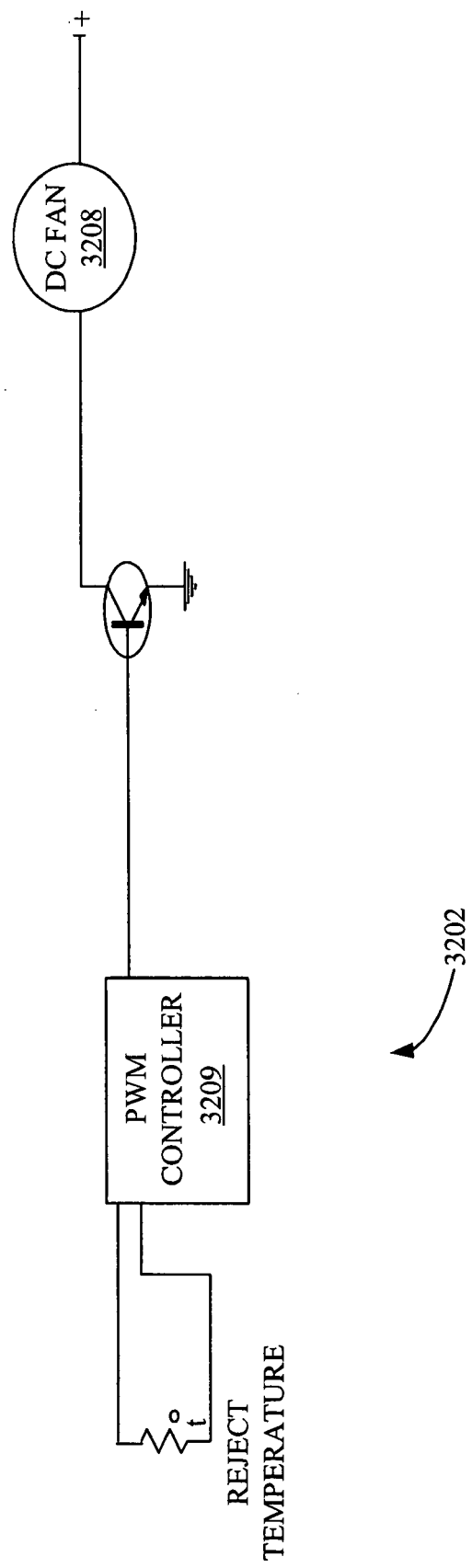
FIG. 33 depicts a conceptual wiring diagram illustrating a cooling fan low power mode, according to various embodiments of the present invention.

FIG. 33 depicts a conceptual wiring diagram illustrating a direct current cooling fan low power mode, according to various embodiments of the present invention. A second circuit diagram 3202 illustrates a low power mode for a direct current fan 3208. Rather than reducing power when the production of liquid gas is no longer required, fan speed may be automatically reduced or increased to maintain a constant cryocooler reject temperature (or cooling fin temperature) at a predefined temperature. The reject temperature may be monitored and compared to a setpoint. Based on this difference, a switching device may be pulsed at a higher or lower rate by the PWM controller 3209, controlling the fan 3208 air flow and set temperature of the cryocooler.

According to embodiments in which a low power mode is entered by simply reducing the power supplied to the cryocooler to a predetermined power, the system eventually arrives at equilibrium, at which the temperature of the cold finger tip may depend on a combination of factors, including, but not limited to the cooling efficiency of the cryocooler and the thermal load to which the cryocooler is subjected. The thermal load experienced by the cryocooler may depend on factors including, but not limited to, the flow rate of gas directed across the cold finger, the inlet temperature of the gas, and the thermal inefficiencies of the dewar and dewar seal flange. Because variations may exist in all of these parameters based on physical differences between separately manufactured components, an inlet power to the cryocooler should be set high enough to accommodate for the worst case variation. Such a cryocooler power setting may result in the cryocooler drawing a power greater than the power necessary to achieve an adequate liquefaction rate. Such extra power would generally further reduce the temperature of the cold finger during liquefaction. However, according to some alternative embodiments of the present invention, instead of simply reducing power supplied to the cryocooler to a predetermined level, a low power mode may be entered by monitoring the temperature of the cold end of the cold finger and adjusting power input to the cryocooler to maintain a predetermined cold end temperature during a low power mode. In such alternative embodiments, liquid may be produced until the dewar is filled, then the power supplied to the cryocooler may be reduced while monitoring the cold finger tip temperature. The predetermined cold end temperature may be found by experimentally varying the temperature until a temperature is found that maintains the liquid volume within the dewar measured by a scale. Such a method may, in some cases, permit a more cost-effective and energy-saving design of a liquefaction system, and may also compensate for potential decrease in cryocooler efficiency over time.

A liquefaction apparatus may also employ other electronic systems to improve safety, efficiency, and cost. For instance, when power is first applied to the system, all the user indicator lamps may be activated to allow a user to verify that all lamps work properly; after a short period of time, the lamps, except for the power lamp, may be deactivated and the system may enter normal operation.

Additionally, various electronic means may be employed to control the cryocooler. The cryocooler firing angle may be varied so that the proper RMS voltage is applied to the linear motor, maintaining the desired piston stroke, as external operating conditions change. A piston stroke control loop compares the stroke set-point to the piston amplitude from a re-construction circuit. This may be accomplished by controlling the firing angle to a random-phase, opto-isolation Triac-driver. The firing Triac device and the front-end re-construction circuit may be electrically isolated from the control and feed-back circuitry. Also, the stroke of the cryocooler piston may be estimated using an isolated back-EMF of the motor and an isolated monitoring of the motor current. Integration of the resultant motor velocity results in a real-time, sensor-less measurement of piston stroke. At the start of the cryocooler power-up sequence, the cryocooler piston is lifted to its maximum state by rectifying the AC voltage and controlling the resultant DC power to the cooler. This is accomplished by controlling the firing angle to a random-phase, opto-isolation Triac-driver and the use of a full-wave Diode-Bridge and a Triac combination.

Figure 34:
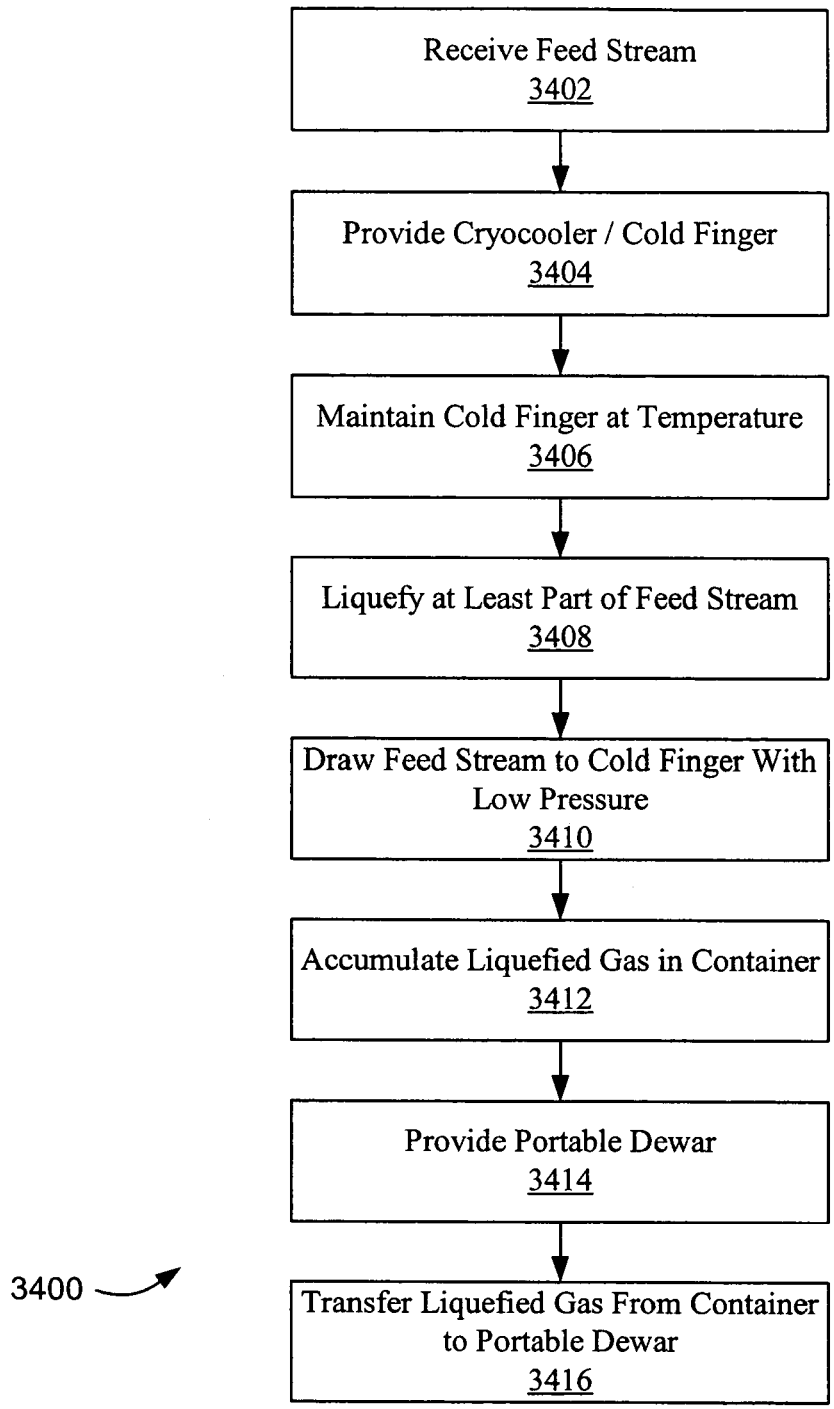
FIG. 34 depicts a flow diagram illustrating a method for maintaining oxygen purity in liquefaction of gas, according to various embodiments of the present invention.

FIG. 34 depicts a flow diagram 3400 illustrating a method for maintaining oxygen purity in liquefaction of gas for residential oxygen therapy, according to various embodiments of the present invention. A feed stream of gas is received from an oxygen concentrator (block 3402). A cryocooler is provided, the cryocooler including a cold finger, and the cold finger extending within a container and operable to liquefy the gas for containment in the container (block 3404). The cold finger may be maintained at a substantially constant temperature at or below the liquefaction temperature of oxygen (block 3406). At least part of the feed stream of gas is liquefied, the oxygen purity of liquefied gas being substantially at or greater than the oxygen purity of the feed stream of gas (block 3408). The feed stream of gas may be drawn to the cold finger at least in part with a low pressure created by liquefaction of the feed stream of gas at a surface of the cold finger (block 3410). Liquefied gas may be accumulated in the container (block 3412). According to some embodiments of the present invention, a portable dewar may be provided to store the liquefied gas for ambulatory medical gas therapy (block 3414), and the liquefied gas may be transferred from the container to the portable dewar (block 3416).

Figure 35:
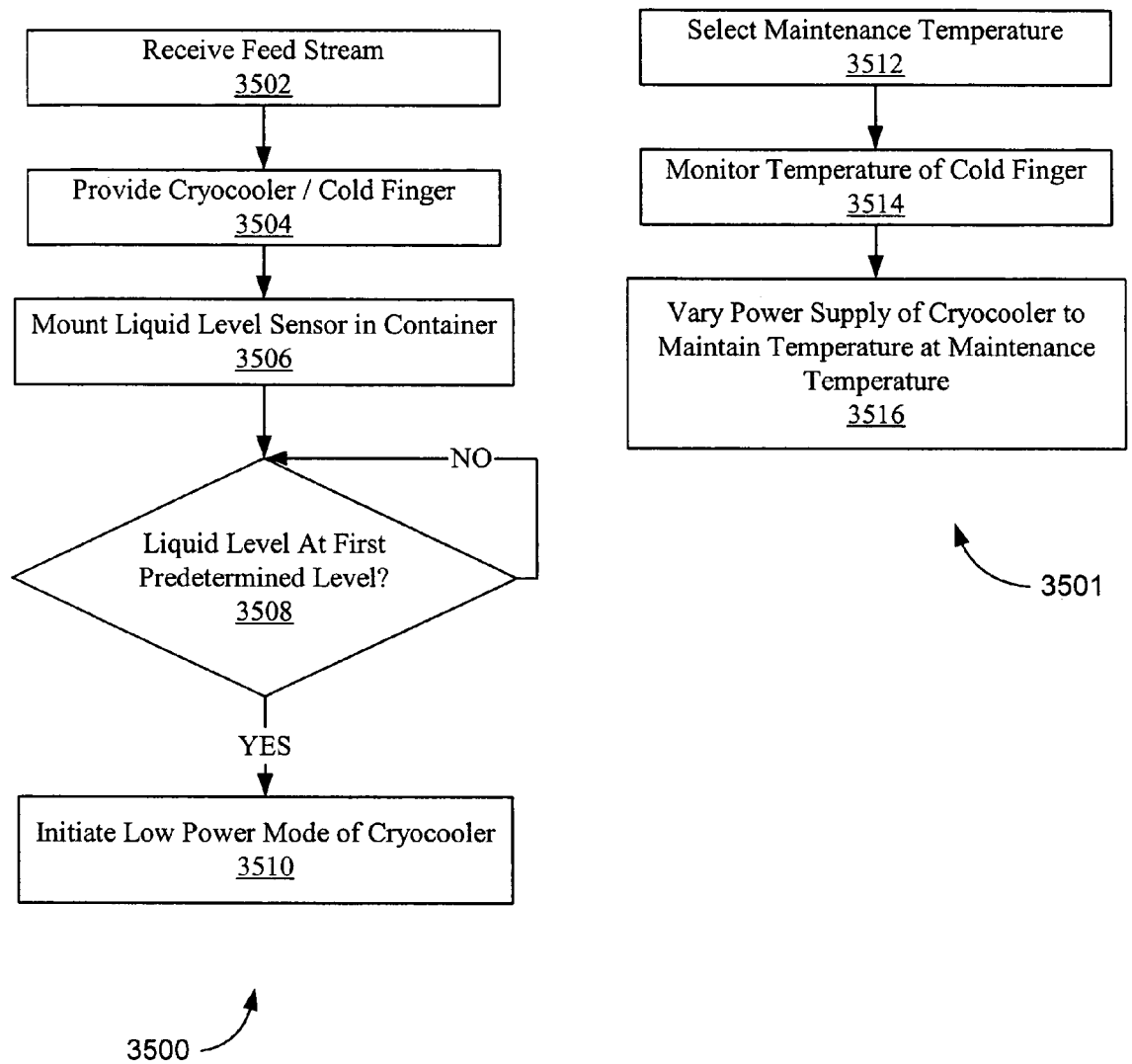
FIG. 35 depicts flow diagrams illustrating a method for reducing power consumption in residential medical gas liquefaction and storage and a method for initiating a low power mode of a cryocooler, according to various embodiments of the present invention.

FIG. 35 depicts flow diagrams illustrating a method for reducing power consumption in residential medical gas liquefaction and storage and a method for initiating a low power mode of a cryocooler, according to various embodiments of the present invention. Flow diagram 3500 illustrates a method for reducing power consumption in residential medical gas liquefaction and storage. A feed stream of gas may be received from an oxygen concentrator (block 3502). A cryocooler may be provided, the cryocooler including a cold finger, and the cold finger extending within a container and operable to liquefy at least part of the feed stream of gas for containment in the container (block 3504). A liquid level sensor may be mounted within the container, the liquid level sensor operable to detect a liquid level in the container (block 3506). A determination is made whether the detected liquid level is at or greater than the first predetermined liquid level (block 3508). If not, then the liquid level sensor continues to detect the liquid level (block 3508). If the detected liquid level is at or greater than the first predetermined liquid level, such as a full liquid level, then a low power mode of the cryocooler may be initiated (block 3510).

Flow diagram 3501 illustrates a method for initiating a low power mode of a cryocooler. A maintenance temperature may be selected (block 3512), and the temperature of the cold finger may be monitored (block 3514). The power supply to the cryocooler may be varied in order to maintain the temperature of the cold finger at the maintenance temperature (block 3516).

Figure 36:
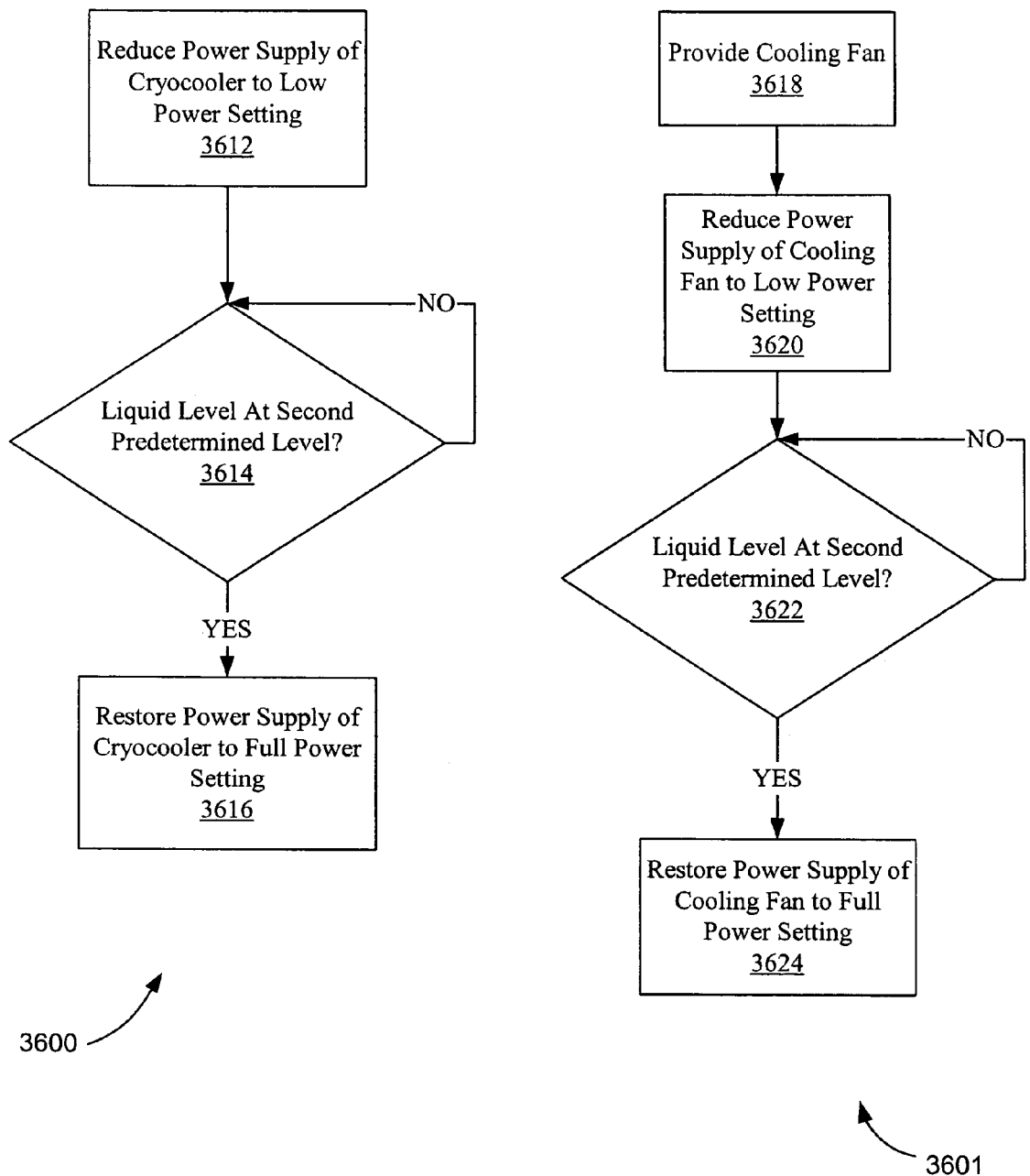
FIG. 36 depicts flow diagrams illustrating methods for initiating a low power mode of a cryocooler, according to various embodiments of the present invention.

FIG. 36 depicts flow diagrams 3600, 3601 illustrating methods for initiating a low power mode of a cryocooler, according to various embodiments of the present invention. Flow diagram 3600 illustrates a method for initiating the low power mode of the cryocooler. The power supply of the cryocooler may be reduced to a low power setting (block 3612). A determination may be made whether the liquid level in the dewar is at or below the second predetermined liquid level (block 3614). If not, then the liquid level detection may continue (block 3614). If the liquid level in the dewar is at or below the second predetermined liquid level, such as at a three-fourths full level, then the power supply to the cryocooler may be restored to a full power setting (block 3616). Flow diagram 3601 illustrates further elements of a method for initiating a low power mode. A cooling fan may be provided (block 3618). The power supply of the cooling fan may be reduced to a low power setting (block 3620). A determination may be made whether the liquid level in the dewar is at or below the second predetermined liquid level (block 3622). If not, then the liquid level detection may continue (block 3622). If the liquid level in the dewar is at or below the second predetermined liquid level, such as at a three-fourths full level, then the power supply to the cooling fan may be restored to a full power setting (block 3624).

While the preferred embodiments of the invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claims. For example, use of the term "oxygen" in this disclosure may generally be substituted with any liquefiable medically-useful gas, such as nitrogen, oxygen, argon, air, and/or a mixture thereof. In addition, although reference is made to medically-useful gas, embodiments of the present invention may be used to produce liquid gas useful for industrial or other purposes.

What is claimed is:

1. An apparatus for enhancing safety in gas liquefaction or liquid gas storage, the apparatus comprising:
   a container operable to contain liquid gas for portable medical gas therapy; and
   a boiloff vessel comprising a first opening and a second opening, the first opening in fluid communication with the container and configured to receive a rapidly expanding mixture of gas and the liquid gas upon a tipping or tilting of the container, the second opening in fluid communication with an outer space larger than the container, the boiloff vessel configured to permit the liquid gas within the rapidly expanding mixture to fall to a bottom of the boiloff vessel while permitting the gas within the rapidly expanding mixture to exit the boiloff vessel and vent into the outer space via the second opening.

2. The apparatus of claim 1, further comprising:
   a gas vent line, wherein the boiloff vessel is in fluid communication with the container via the gas vent line, and wherein the gas vent line is operable to vent gas from the container.

3. The apparatus of claim 1, wherein the boiloff vessel is further configured to contain the liquid gas fallen from the rapidly expanding mixture until the liquid gas has evaporated and exited the boiloff vessel via the second opening.

4. The apparatus of claim 1, wherein the boiloff vessel is a cylindrical vessel having a first end and a second end, wherein the first end comprises the first opening, and wherein the second end comprises the second opening.

5. The apparatus of claim 1, wherein the boiloff vessel is a cylindrical vessel having a first end and a second end, wherein the first end comprises the first opening, and wherein the second opening is located closer to the first end than to the second end.

6. The apparatus of claim 5, further comprising:
   a vent line in fluid communication with the first opening, wherein the vent line extends away from a cryocooler in a first direction, wherein the cryocooler is in communication with the container, wherein the second opening opens toward a second direction, and wherein the first direction is substantially opposite from the second direction.

7. The apparatus of claim 1, further comprising:
   a cryocooler comprising a condenser, the condenser operable to liquefy gas for containment in the container.

8. The apparatus of claim 7, further comprising:
   an accelerometer configured to break an electrical power circuit of the cryocooler when the container experiences an acceleration greater than a predetermined acceleration.

9. The apparatus of claim 7, further comprising a means for decreasing a rate at which the rapidly expanding mixture travels from the container to the boiloff vessel upon a tipping of the container.

10. The apparatus of claim 7, the apparatus further comprising:
    an oxygen concentrator operable to supply a feed stream of oxygen gas;
    a feed tube configured to carry the feed stream from the oxygen concentrator to the cryocooler; and
    a one-way check valve situated in the feed tube, the one-way check valve configured to permit the feed stream to flow from the oxygen concentrator to the cryocooler in one direction, and to prevent a back pressure from the cryocooler to the oxygen concentrator in an opposite direction.

11. The apparatus of claim 10, further comprising:
    a first pressure relief line having a first end and a second end, the first end of the first pressure relief line in fluid communication with the feed tube at a location between the one-way check valve and the cryocooler, the second end of the first pressure relief line in fluid communication with the boiloff vessel, the first pressure relief line comprising a first pressure relief valve configured to permit fluid flow through the first pressure relief line from the feed tube to the boiloff vessel when a first pressure within the feed tube exceeds a predetermined pressure;
    a vent tube having a first end and a second end, the first end of the vent tube in fluid communication with the container, the second end of the vent tube in fluid communication with the boiloff vessel, the vent tube configured to permit gases to exit the container; and
    a second pressure relief line in fluid communication with the vent tube, the second pressure relief line comprising a second pressure relief valve configured to permit fluid flow through the second pressure relief line from the vent tube when a second pressure within the vent tube exceeds the predetermined pressure.

12. The apparatus of claim 11, wherein the vent tube comprises a solenoid valve operable to stop flow through the vent tube, and wherein the second pressure relief line bypasses the solenoid valve.

13. An apparatus for enhancing safety in oxygen gas liquefaction or liquid oxygen gas storage, the apparatus comprising:
    a dewar operable to contain liquid oxygen gas;
    a cryocooler comprising a cold finger, the cold finger extending within the dewar and operable to liquefy oxygen gas for containment in the dewar; and
    a switch configured to break an electrical power circuit of the cryocooler when the dewar tips through a predetermined angle.

14. The apparatus of claim 13, wherein the switch is a mercury switch and wherein the predetermined angle is at least approximately forty-five degrees.

15. An apparatus for decreasing escape rate of liquid oxygen in a tipping event, the apparatus comprising:
    a container operable to contain liquid oxygen for oxygen therapy;
    a cryocooler comprising a cold finger, the cold finger extending within the container and operable to liquefy oxygen gas for containment in the container;
    an annular channel defined by the cryocooler and the container on an outer side and the cold finger on an inner side, the oxygen gas flowing through the annular channel; and a barrier situated in the annular channel and configured to reduce a cross-sectional area of the annular channel to decrease an escape rate of a rapidly expanding combination of the liquid oxygen and the oxygen gas upon a tipping of the container.

16. The apparatus of claim 15, further comprising:
a first flange formed on the cryocooler encircling the cold finger; and
a second flange formed on the container, the second flange releasably coupled to the first flange to form the annular channel, through which the oxygen gas flows between the cryocooler and the container without escaping between the first flange and the second flange.

17. The apparatus of claim 16, wherein the first flange has an outer diameter that increases as it approaches the second flange forming a first sloped surface, wherein the second flange has an outer diameter that increases as it approaches the first flange forming a second sloped surface, the apparatus further comprising:
a clamp configured to conform to the first sloped surface and the second sloped surface, the clamp further configured to apply a normal force to each of the first and second sloped surfaces to create a corresponding axial force that pushes the first flange and the second flange together.

18. The apparatus of claim 16, wherein the barrier is situated at least partially between the first flange and the second flange.

19. The apparatus of claim 18, wherein the barrier is interposed between the first flange and the second flange.

20. The apparatus of claim 15, further comprising:
a boiloff vessel comprising a first opening and a second opening, the first opening in fluid communication with the container and configured to receive the rapidly expanding combination of the liquid oxygen and the oxygen gas upon a tipping of the container, the boiloff vessel configured to permit the liquid oxygen within the rapidly expanding combination to fall to a bottom of the boiloff vessel while permitting the oxygen gas within the rapidly expanding combination to exit the boiloff vessel via the second opening.

21. The apparatus of claim 15, wherein the barrier is integral with the cryocooler.

22. The apparatus of claim 15, wherein the barrier reduces a cross-sectional width of the annular channel to approximately ten thousandths to fifteen thousandths of an inch.

23. The apparatus of claim 15, wherein the annular channel is a first annular channel, wherein the inner side is a first inner side, wherein the outer side is a first outer side, and wherein the barrier comprises:
a flow director portion configured to encircle at least a portion of the cold finger, the flow director portion separating at least a portion of the first annular channel into a second annular channel and a third annular channel, the second annular channel defined by the flow director portion on a second outer side and the cold finger on the first inner side, the third annular channel defined by the cryocooler and the container on the first outer side and the flow director portion on a second inner side;
wherein feed stream gas flows through the second annular channel and vent gas flows through the third annular channel.

24. An apparatus for enhancing safety in oxygen gas liquefaction, the apparatus comprising:
a container operable to contain liquid oxygen for portable oxygen therapy;
a cryocooler comprising a cold finger and a heat dissipator, the cold finger extending within the container and operable to liquefy oxygen gas for containment in the container; and
a temperature sensing circuit comprising a temperature sensor in proximity with the heat dissipator, the temperature sensing circuit operable to break an electrical power circuit of the cryocooler when a sensed temperature exceeds a predetermined temperature incompatible with proper cryocooler operation.

25. An apparatus for enhancing safety in oxygen gas liquefaction, the apparatus comprising:
a container operable to contain liquid oxygen for portable oxygen therapy;
a cryocooler comprising a cold finger, the cold finger extending within the container and operable to liquefy oxygen gas for containment in the container;
a temperature sensing circuit comprising a temperature sensor in proximity with the cold finger, the temperature sensing circuit operable to break an electrical power circuit of the cryocooler when a sensed temperature exceeds a predetermined temperature incompatible with proper cryocooler operation.

26. An apparatus for enhancing safety in gas liquefaction, the apparatus comprising:
a container operable to contain liquid oxygen for portable oxygen therapy;
a cryocooler comprising a cold finger, the cold finger extending within the container and operable to liquefy oxygen gas for containment in the container;
an oxygen concentrator operable to supply a feed stream of the oxygen gas;
a feed tube configured to carry the feed stream from the oxygen concentrator to the cryocooler;
an oxygen purity sensor in fluid communication with the feed tube, the oxygen purity sensor configured to observe oxygen purity of the feed stream and to transmit a signal indicating the oxygen purity; and
an oxygen purity indicator configured to receive the signal and to display a graphical representation of the oxygen purity.

27. The apparatus of claim 26, wherein the graphical representation is green if the oxygen purity exceeds a predetermined level for oxygen therapy use, and wherein the graphical representation is red if the oxygen purity is less than the predetermined level.

28. The apparatus of claim 27, wherein the predetermined level is ninety percent by volume.

29. The apparatus of claim 26, wherein the graphical representation is a digital numerical representation indicating a percentage of the oxygen gas by volume in the feed stream.

30. The apparatus of claim 1, wherein the outer space is an atmosphere surrounding the container.

31. An apparatus for enhancing safety in oxygen gas liquefaction or liquid oxygen gas storage, the apparatus comprising:
a dewar operable to contain liquid oxygen gas;
a cryocooler comprising a condenser, the condenser operable to liquefy oxygen gas for containment in the dewar; and
a switch configured to break an electrical power circuit of the cryocooler when the dewar tips through a predetermined angle.

32. The apparatus of claim 31, wherein the switch is a mercury switch and wherein the predetermined angle is at least approximately forty-five degrees.

33. An apparatus for enhancing safety in oxygen gas liquefaction, the apparatus comprising:
- a container operable to contain liquid oxygen for portable oxygen therapy;
- a cryocooler comprising a condenser and a heat dissipator, the condenser operable to liquefy oxygen gas for containment in the container; and
- a temperature sensing circuit comprising a temperature sensor in proximity with the heat dissipator, the temperature sensing circuit operable to break an electrical power circuit of the cryocooler when a sensed temperature exceeds a predetermined temperature incompatible with proper cryocooler operation.

34. An apparatus for enhancing safety in oxygen gas liquefaction, the apparatus comprising:
- a container operable to contain liquid oxygen for portable oxygen therapy;
- a cryocooler comprising a condenser, the condenser operable to liquefy oxygen gas for containment in the container;
- a temperature sensing circuit comprising a temperature sensor in proximity with the condenser, the temperature sensing circuit operable to break an electrical power circuit of the cryocooler when a sensed temperature exceeds a predetermined temperature incompatible with proper cryocooler operation.

35. An apparatus for enhancing safety in gas liquefaction, the apparatus comprising:
- a container operable to contain liquid oxygen for portable oxygen therapy;
- a cryocooler comprising a condenser, the condenser operable to liquefy oxygen gas for containment in the container;
- an oxygen concentrator operable to supply a feed stream of the oxygen gas;
- a feed tube configured to carry the feed stream from the oxygen concentrator to the cryocooler;
- an oxygen purity sensor in fluid communication with the feed tube, the oxygen purity sensor configured to observe oxygen purity of the feed stream and to transmit a signal indicating the oxygen purity; and
- an oxygen purity indicator configured to receive the signal and to display a graphical representation of the oxygen purity.

36. The apparatus of claim 35, wherein the graphical representation is green if the oxygen purity exceeds a predetermined level for oxygen therapy use, and wherein the graphical representation is red if the oxygen purity is less than the predetermined level.

37. The apparatus of claim 36, wherein the predetermined level is ninety percent by volume.

38. The apparatus of claim 35, wherein the graphical representation is a digital numerical representation indicating a percentage of the oxygen gas by volume in the feed stream.

* * * * *